US012714077B2

(12) United States Patent
Ayares et al.

(10) Patent No.: US 12,714,077 B2
(45) Date of Patent: Aug. 25, 2026

(54) MULTI-TRANSGENIC PIG FOR XENOTRANSPLANTATION

(71) Applicant: REVIVICOR, INC, Blacksburg, VA (US)

(72) Inventors: David L. Ayares, Blacksburg, VA (US); Carol Phelps, Floyd, VA (US)

(73) Assignee: Revivicor, Inc., Blacksburg, VA (US)

( * ) Notice: Subject to any disclaimer, the term of this patent is extended or adjusted under 35 U.S.C. 154(b) by 903 days.

(21) Appl. No.: 15/758,895

(22) PCT Filed: Sep. 9, 2016

(86) PCT No.: PCT/US2016/051126
§ 371 (c)(1),
(2) Date: Mar. 9, 2018

(87) PCT Pub. No.: WO2017/044864
PCT Pub. Date: Mar. 16, 2017

(65) Prior Publication Data

US 2018/0249688 A1 Sep. 6, 2018

Related U.S. Application Data

(60) Provisional application No. 62/216,225, filed on Sep. 9, 2015, provisional application No. 62/256,068, filed on Nov. 16, 2015.

(51) Int. Cl.

| | |
|---|---|
| ***A01K 67/0278*** | (2024.01) |
| ***A01K 67/0275*** | (2024.01) |
| ***C12N 15/85*** | (2006.01) |
| ***C12N 15/877*** | (2010.01) |
| ***C12N 15/90*** | (2006.01) |

(52) U.S. Cl.
CPC ...... *A01K 67/0278* (2013.01); *A01K 67/0275* (2013.01); *C12N 15/8509* (2013.01); *C12N 15/8778* (2013.01); *C12N 15/907* (2013.01); *A01K 2217/052* (2013.01); *A01K 2217/072* (2013.01); *A01K 2217/15* (2013.01); *A01K 2217/206* (2013.01); *A01K 2227/108* (2013.01); *A01K 2267/025* (2013.01); *C12N 2800/30* (2013.01); *C12N 2840/20* (2013.01)

(58) Field of Classification Search
CPC ............ A01K 67/0278; A01K 67/0275; A01K 2217/052; A01K 2217/072; A01K 2217/15; A01K 2217/206; A01K 2227/108; A01K 2267/025; C12N 15/8509; C12N 15/8778; C12N 15/907; C12N 2800/30; C12N 2840/20
USPC .......................... 800/17, 21; 435/320.1, 325
See application file for complete search history.

(56) References Cited

U.S. PATENT DOCUMENTS

| | | | |
|---|---|---|---|
| 4,736,866 | A | 4/1988 | Leder et al. |
| 4,873,191 | A | 10/1989 | Wagner et al. |
| 4,888,274 | A | 12/1989 | Radding et al. |
| 4,944,384 | A | 7/1990 | Herron |
| 5,057,420 | A | 10/1991 | Massey |
| 5,334,575 | A | 8/1994 | Noonan et al. |
| 5,453,457 | A | 9/1995 | Meltzer et al. |
| 5,496,720 | A | 3/1996 | Susko-Parrish et al. |
| 5,523,226 | A | 6/1996 | Wheeler |
| 5,730,403 | A | 3/1998 | Johnson |
| 5,747,340 | A | 5/1998 | Harats et al. |
| 5,821,117 | A | 10/1998 | Sandrin et al. |
| 5,859,307 | A | 1/1999 | Mombaerts et al. |
| 5,945,577 | A | 8/1999 | Stice et al. |
| 5,977,318 | A | 11/1999 | Linsley et al. |
| 6,066,725 | A | 5/2000 | Deboer et al. |
| 6,147,276 | A | 11/2000 | Campbell et al. |
| 6,153,428 | A | 11/2000 | Gustafsson et al. |
| 6,166,288 | A | 12/2000 | Diamond et al. |
| 6,215,041 | B1 | 4/2001 | Stice et al. |
| 6,235,969 | B1 | 5/2001 | Stice et al. |
| 6,252,133 | B1 | 6/2001 | Campbell et al. |
| 6,258,998 | B1 | 7/2001 | Damiani et al. |
| 6,376,743 | B1 | 4/2002 | Yanagimachi |
| 6,413,769 | B1 | 7/2002 | Gustafsson et al. |
| 6,423,316 | B1 | 7/2002 | Riesbeck et al. |
| 6,506,559 | B1 | 1/2003 | Fire et al. |
| 6,525,243 | B1 | 2/2003 | Stockman Campbell et al. |

(Continued)

FOREIGN PATENT DOCUMENTS

| | | |
|---|---|---|
| CN | 1582332 | 2/2005 |
| CN | 108949832 A | 12/2018 |

(Continued)

OTHER PUBLICATIONS

Deng et al. (2011) PLoS One, vol. 6(5), e19986, pp. 1-9.*
Hai et al. (2014) Cell Research, vol. 24, 372-375.*
Nottle et al. (2007) Xenotransplantation, vol. 14(4), 339-344; doi.org/10.1111/j.1399-3089.2007.00417.x.*
Deng et al. (2011) PLoS One, vol. 6(5):e19986. doi:10.1371/journal.pone.0011986, pp. 1-9.*
Harris et al. (2014) Xenotransplantation, vol. 21(6), 496-506, published online Jul. 5, 2014. Doi:10.1111/xen.12116, pp. 1-21.*
Kriz et al. (2010) Nat. Commun.1:120 doi: 10.1038/ncomms1120, pp. 1-6, and Supplemental Material, pp. 1-21.*

(Continued)

*Primary Examiner* — Anne Marie S Wehbe
(74) *Attorney, Agent, or Firm* — Foley & Lardner LLP

(57) ABSTRACT

The present invention is directed to transgenic animals (e.g., transgenic porcine animals) comprising multiple genetic modifications that advantageously render these animals suitable donors for xenotransplanation. The present invention extends to organs, organ fragments, tissues and cells derived from these animals and their therapeutic use. The present invention further extends to methods of making such animals. In certain embodiments, the transgenic animals (e.g., transgenic porcine animals) lack expression of alpha gal and incorporate and express at least four transgenes under the control of at least two promoters.

19 Claims, 19 Drawing Sheets

(56) References Cited

U.S. PATENT DOCUMENTS

| | | | | |
|---|---|---|---|---|
| 6,548,741 | B2 | 4/2003 | Desousa et al. | |
| 6,573,099 | B2 | 6/2003 | Graham | |
| 6,639,122 | B1 | 10/2003 | Tu et al. | |
| 6,872,868 | B1 | 3/2005 | Wagner et al. | |
| 7,304,033 | B2 | 12/2007 | Larsen et al. | |
| 7,368,284 | B2 | 5/2008 | Koike | |
| 7,378,569 | B2 | 5/2008 | Tu et al. | |
| 7,462,466 | B2 | 12/2008 | Morgan et al. | |
| 7,755,462 | B2 | 7/2010 | Fullerton et al. | |
| 11,179,496 | B2 | 11/2021 | Ayares | |
| 2001/0044937 | A1 | 11/2001 | Schatten et al. | |
| 2002/0062492 | A1 | 5/2002 | Lubon et al. | |
| 2002/0068713 | A1 | 6/2002 | Rade et al. | |
| 2002/0108132 | A1 | 8/2002 | Rapp | |
| 2003/0014770 | A1 | 1/2003 | Gustafsson et al. | |
| 2005/0155095 | A1 | 7/2005 | Koike | |
| 2005/0223418 | A1 | 10/2005 | Koike | |
| 2006/0068479 | A1 | 3/2006 | Koike | |
| 2007/0113297 | A1 | 5/2007 | Yang et al. | |
| 2007/0286845 | A1 | 12/2007 | Harats et al. | |
| 2009/0186097 | A1 | 7/2009 | Ayares | |
| 2011/0038841 | A1* | 2/2011 | Ayares ................ | C12N 9/1051 424/93.21 |
| 2013/0347134 | A1 | 12/2013 | Diacovo et al. | |
| 2014/0017215 | A1* | 1/2014 | Ayares ............... | A01K 67/0275 435/325 |
| 2015/0106962 | A1 | 4/2015 | Sachs et al. | |
| 2021/0392863 | A1 | 12/2021 | Kim et al. | |
| 2022/0072200 | A1 | 3/2022 | Ayares | |

FOREIGN PATENT DOCUMENTS

| | | | |
|---|---|---|---|
| WO | WO-90/03432 | A1 | 4/1990 |
| WO | WO-94/21799 | A1 | 9/1994 |
| WO | WO-94/24274 | A1 | 10/1994 |
| WO | WO-94/26884 | A1 | 11/1994 |
| WO | WO-95/20661 | A1 | 8/1995 |
| WO | WO-95/28412 | A1 | 10/1995 |
| WO | WO-97/07668 | A1 | 3/1997 |
| WO | WO-97/07669 | A1 | 3/1997 |
| WO | WO-98/07841 | A1 | 2/1998 |
| WO | WO-98/15626 | A2 | 4/1998 |
| WO | WO-98/30683 | A2 | 7/1998 |
| WO | WO-99/07829 | A1 | 2/1999 |
| WO | WO-99/49029 | A1 | 9/1999 |
| WO | WO-99/53042 | A2 | 10/1999 |
| WO | WO-99/57266 | A2 | 11/1999 |
| WO | WO-00/04217 | A1 | 1/2000 |
| WO | WO-00/22098 | A1 | 4/2000 |
| WO | WO-00/31126 | A2 | 6/2000 |
| WO | WO-00/51424 | A2 | 9/2000 |
| WO | WO-01/30966 | A2 | 5/2001 |
| WO | WO-03/005810 | A2 | 1/2003 |
| WO | WO-03/055302 | A1 | 7/2003 |
| WO | WO-03/059923 | A2 | 7/2003 |
| WO | WO-2004/016742 | A2 | 2/2004 |
| WO | WO-2004/028243 | A2 | 4/2004 |
| WO | WO-2007/035213 | A2 | 3/2007 |
| WO | WO 2009/069986 | | 6/2009 |
| WO | WO-2011/020120 | | 2/2011 |
| WO | WO 2012/112586 | | 8/2012 |
| WO | WO 2014/066505 | | 5/2014 |
| WO | WO 2016/065046 | | 4/2016 |
| WO | WO-2019/185936 | A2 | 10/2019 |
| WO | WO-2020/085788 | A1 | 4/2020 |

OTHER PUBLICATIONS

Tena et al. (2014) Am.J.Tranplant., vol. 14(12):2713-2722.doi:10.1111/ajt.12918.*

Yu et al. (2003) Mol. Ther., vol. 7(6), 827-838.*

Quadros et al. (Mar. 10, 2015) FEBS Open Bio, vol. 5, 191-197.*

Lee et al. (Oct. 2015) Proceedings of the Korean Veterinary Medical Association, p. 544, abstract P300.*

Estrada et al. (Mar. 2015) Xenotransplantation, vol. 22, 194-202.*

Aigner et al. (2010) Curr. Opin. Organ Transplant., vol. 15, 201-206.*

Olsson et al. (2006) Int. J. Biochem. & Cell Biol., vol. 38: 492-497.*

Ohtsuka et al. (2015) BMC Genomics, vol. 16:274, DOI 10.1186/s12864-015-1432-5, pp. 1-16.*

Definition of "permit" (2024) Dictionary.com, pp. 1-6.*

Ayares, David et al.: "Genetic Engineering of Source Pigs for Xenotransplantation: Progress and Pro-spects", Xenotransplanta-tion, Sep-Oct. 2013, vol. 20, No. 5, 408, Sep. 20, 2013 (Sep. 20, 2013), p. 361.

Hayato, Iwase et al.: "Pig Kidney Graft Survival in a Baboon for 136 Days: Longest Life-Supporting Organ Graft Survival to Date", Xenotransplantation, vol. 22, No. 4, Jun. 29, (Jun. 29, 2015), pp. 302-309.

Tang, Hai et al.: "One Step Generation of Knockout Pigs by Zgote Injectcion of CRISPR/Cas System", Cell Resesarch—Xibao Yanjiu, vol. 24, No. 3, Jan. 31, 2014 (Jan. 31, 2014), pp. 372-375.

Hilton, Gock, et al.: "Genetic Modification of Pigs for Solid Organ Xenotransplantation", Transplanta-tion Reviews, vol. 25, No. 1, Jan. 1, 2011 (Jan. 1, 2011), pp. 9-20.

Nella, Fisicaro et al.: "Versatile Co-Expression of Graft-Protective Proteins Using 2A-Linked Cassettes: Transgene Co-Expression Using 2A", Xenotransplantation, vol. 18, No. 2, Mar. 1, 2011 (Mar. 1, 2011), pp. 121-130.

Salvaris, Evelyn et al.: "IXA-0-7.1: Multi-Gene Constructs to Accelerate the Generation of Multi-Transgenic GalT Knockout Pigs", Xenotransplantation. Sep. 2009, vol. 16, No. 5, Sep. 2009 (Sep. 2009), p. 373.

Wei, Deng et al.: "Use of the 2A Peptide for Generation of Multi-Transgenic Pigs through a Single Round of Nuclear Trans-fer", Plos One, vol. 6, No. 5, May 13, 2011 (May 13, 2011), p. e19986.

David KC Cooper et al.: "Recent Advances in Understanding Xenotransplantation: Implications for the Clinic", Expert Review of Clinical Immunology, vol. 11, No. 12, Sep. 1, 2015 (Sep. 1, 2015), pp. 1379-1390.

Donald G. Harris et al.: "Meta-Analysis of 1-8, the Independent and Cumulative Effects of 11-27 Multi-ple Genetic Modifications on Pig Lung Xenograft Performance During Ex Vivo Perfusion with Human Blood", Xenotransplantation, vol. 22, No. 2, Dec. 2, 2014 (Dec. 2, 2014), pp. 102-111.

Hayato, Iwase et al.: "Immunological and Physiological Observa-tions in Baboons with Life-Supporting Genetically Engineered Pig Kidney Grafts", Xenotransplantation, vol. 24, No. 2, Mar. 17, 2017 (Mar. 17, 2017), p. e12293.

U.S. Appl. No. 17/531,416, filed Nov. 19, 2021, Rothblatt et al.

Aigner et al., "Transgenic pigs for xenotransplantation: Selection of promoter sequences for reliable transgene expression," Current Opinion in Organ Transplantation, 2010, 15:201-206.

Ayares, "Genetic Modification of Pigs for Regenerative Medicine", Presentation from UC Davis Transgenic Animal Research Conference VII, Aug. 20, 2009.

Ayares, David. "Genetic Modification of Pigs for Xenotransplantation," Transgenic Research, vol. 19, No. 143 (2010).

Bach et al., "Delayed xenograft rejection", Immunol Today, 1996, vol. 17(8), pp. 379-384.

Bronson et al., "Single-copy transgenic mice with chosen-site integration," Proc. Natl. Acad. Sci. USA, Aug. 1996, 93:9067-9072.

Byrne et al., "Increased Immunosuppression, Not Anticoagulation, Extends Cardiac Xenograft Survival," Transplantation, 2006, 82:1787-1791.

Byrne et al., "Transgenic Pigs Expressing Human CD59 and Decay-Accelerating Factor Produce an Intrinsic Barrier to Complement-Mediated Damage1," Transplantation, 1997, 63(1):149-155.

Chen et al., "Complete Inhibition-of Acute Humoral Rejection Using Regulated Expression of Membrane-tethered Anticoagulants on Xenograft Endothelium", American Journal of Transplantation, 2004, vol. 4, pp. 1958-1963.

Chen et al., "Inhibition of intravascular thrombosis in murine endotoxemia by targeted expression of hirudin and tissue factor pathway inhibitor analogs to activated endothelium", Blood, 2004, vol. 104(5), pp. 1344-1349.

(56) References Cited

OTHER PUBLICATIONS

Costa et al., "Expression of the human al ,2-fucosyltransferase in transgenic pigs modifies the cell surf ace carbohydrate phenotype and confers resistance to human serum-mediated cytolysis", Faseb J, 1999, vol. 13, pp. 1762-1773.
Cowan et al., "Coagulation and the xenograft endothelium", Xenotransplantation, 2007, vol. 14(1), pp. 7-12.
Cozzi et al., "Preliminary study in a life supporting pig to primate xenotransplantation model using GAL KO pigs transgenic for human CD39, CD55, CD59 and fucosyltransferase," (Abstract LB IXA O-4), Xenotransplantation, 2009, 16:544.
Dai et al., "Targeted disruption of the al ,3-galactosyltransferase gene in cloned pigs", Nature Biotechnology, 2002, vol. 20, pp. 251-255.
Dalmasso et al., "Reaction of Complement With Endothelial Cells in a Model of Xenotransplantation", Clin. Exp. Immunol., 1991, vol. 86, pp. 31-35.
Dalmasso et al., "Inhibition of Complement-Mediated Endothelial Cell Cytotoxicity By Decay-Accelerating Factor", Transplantation, 1991, vol. 52(3), pp. 530-533.
Denning et al., "Deletion of the a(1,3)galactosyl transferase (GGTA 1) gene and the prion protein (PrP) gene in sheep", Nature Biotechnology, 2001, vol. 19, pp. 559-562.
Diamond et al., "Human CD59 expressed in transgenic mouse hearts inhibits the activation of complement", Transplant Immunology, 1995, vol. 3, pp. 305-312.
Dwyer et al., "Thromboregulatory manifestations in human CD39 transgenic mice and the implications for thrombotic disease and transplantation", The Journal of Clinical Investigation, 2004, vol. 113(10), pp. 1440-1446.
Galili et al., "Man, Apes, and Old World Monkeys Differ from Other Mammals in the Expression of a-Galactosyl Epitopes on Nucleated Cells", The Journal of Biological Chemistry, 1988, vol. 263, pp. 17755-17762.
Genbank Accession No. NM_213888.1, 2 pages, downloaded from http://www.ncbi.nlm.nih.gov/nuccore/NM_213888.1 on Feb. 9, 2015.
Giraldo et al,. "Size matters: use of YACs, BACs and PACs in transgenic animals," Transgenic Research, 2001, 10:83-103.
Gock et al., "Genetic modification of pigs for solid organ xenotransplantation," Transplantation Reviews, Jan. 2011, 25:9-20.
Godwin et al., "Towards endothelial cell-specific transgene expression in pigs: characterization of the pig ICAM-2 promoter", Xenotransplantation, 2006, vol. 13(6), pp. 514-521.
Harrison et al., "Efficient generation of a.(1,3) galactosyltransferase knockout porcine fetal fibroblasts for nuclear transfer", Transgenic Research, 2002, vol. 11, pp. 143-150.
Houdebine, Louis-Marie, "Relations between animal transgenesis and reproduction," Reprod. Nutr. Dev., 2005, 45:363-376.
Koike et al., "Direct gene replacement of the mouse a(1,3)-galactosyltransferase gene with human a(1,2)-fucosyltransferase gene: Converting a-galactosyl epitopes into H anti.gens", Xenotransplantation, 1997, vol. 4, pp. 147-152.
Lai et al., ".Production of a-1,3-Galactosyltransferase Knockout Pigs by Nuclear Transfer Cloning", Science, 2002, vol. 295, pp. 1089-1092.
Larin et al., "A method for linking yeast artificial chromosomes," Nucleic Acids Research, 1996, 24(21):4192-4196.
Lee et al., "Characterization of Transgenic Pigs That Express Human Decay Accelerating Factor and Cell Membrane-tethered Human Tissue Factor Pathway Inhibitor", Reprod Dom Anim, 2010, pp. 1-8.
Lui et al., "Mammary gland-specific secretion of biologically active immunosuppressive agent cytotoxic-T lymphocyte antigen 4 human immunoglobulin fusion protein (CTLA4lg) in milk by transgenesis", Journal of Immunological Methods, 2003, vol. 277, pp. 171-183.
Martin et al., "Transgenic expression of CTLA4-lg by fetal pig neurons for xenotransplantation", Transgenic Research, 2005, vol. 14, pp. 373-384.
Mirenda et al., "Achieving Permanent Survival of Islet Xenografts by Independent Manipulation of Direct and Indirect T-Cell Responses", Diabetes, 2005, vol. 54, pp. 1048-1055.
Miyagawa et al., "Remodeling of the Major Pig Xenoantigen by N-Acetylglucosaminyltransferase III in Transgenic Pig", The Journal of Biological Chemistry, 2001, vol. 276(42), pp. 39310-39319.
Mohiuddin et al., "One-Year Heterotopic Cardiac Xenograph Survival in a Pig to Baboon Model," Am. J. Transplant, Feb. 2014, 14(2):488-489.
Niemann et al. "Production and characterization of multi-transgenic pigs for xenotransplantation," Transgenic Research, vol. 19 (2010) (pp. 143-144).
Niemann et al., "Production and Characterization of Multi-transgenic Pigs for Xeno Transplantation," Transgenic Research, 2010, 19:143-144.
Phelps et al., "Production of u 1,3-Galactosyltransferase Deficient Pigs", Science, 2003, vol. 299, pp. 411-414.
Piedrahita et al., "Cloning and transgenesis in mammals: Implications for xenotransplantation," American Journal of Transplantation, 2004, 4(Suppl.6):43-50.
Ramsoondar et al., "Production of al,3-Galactosyltransferase-Knockout Cloned Pigs Expressing Human al,2-Fucosylosyltransferase", Biology of Reproduction, 2003, vol. 69, pp. 437-445.
Sachs et al., "Genetic Manipulation in Pigs," Curr. Opin. Organ Transplant., Apr. 2009, 14(2):148-153.
Schlaeger et al., "Uniform vascular-endothelial-cell-specific gene expression in both embryonic and adult transgenic mice", 1997, vol. 94(7), pp. 3058-3063.
Shimizu et al., "Thrombotic Microangiopathic Glomerulopathy in Human Decay Accelerating Factor-Transgenic Swine-to-Baboon Kidney Xenografts," J. Am. Soc. Nephrol., 2005, 16:2732-2745.
Sprangers et al., "Xenotransplantation: Where are we in 2008?", Kidney International, Apr. 16, 2008, 74:14-21.
Squinto, "Xenogeneic organ transplantation", Current Opinion in Biotechnology, Dec. 1996, vol. 7(6), pp. 641-645.
Stone et al., "Porcine and Bovine Cartilage Transplants in Cynomolgus Monkey", Transplantation, 1997, vol. 63(5), pp. 640-645.
Strahan et al., "PIG alphal,3GALACTOSYLTRANSFERASE: A Major Target for Genetic Manipulation in Xenotransplantation", Frontiers in Bioscience, 1996, vol. 1, pp. 34-41.
Sutherland et al., "Protective Effect of CTLA4lg Secreted By Transgenic Fetal Pancreas Allografts", Transplantation, 2000, vol. 69(9), pp. 1806-1812.
Tai et al., "Progress in Xenotransplantation Following the Introduction of Gene-knockout Technology," Transplant International, 2007, 20:107-117.
Tanemura et al., "Reduction of the Major Swine Xenoantigen, the a-Galactosyl Epitope by Transfection of the a2,3-Sialyltransferase Gene", The Journal of Biological Chemistry, 1998, vol. 273(26), pp. 16421-16425.
Van de Wouwer et al., "Thrombomodulin-Protein C-EPCR System : Integrated to Regulate Coagulation and Inflammation", Arterioscler Thromb Vasc Biol, 2004, vol. 24, pp. 1374-1383.
van der Windt et al., "Rapid loss of intraportally transplanted islets: an overview of pathophysiology and preventive strategies", Xenotransplantation, Jul. 2007, vol. 14(4), pp. 288-297.
Vaughan et al., "Porcine CTLA4-lg Lacks a MYPPPY Motif, Binds Inefficiently to Human B7 and Specifically Suppresses Human CD4 T Cell Responses Costimulated by Pig But Not Human B7", The Journal of Immunology, 2000, pp. 3175-3181.
Ye et al., "Evidence That Intravenously Administered a-Galactosyl Carbohydrates Reduce Baboon Serum Cytotoxicity to Pig Kidney Cells (PK15) and Transplanted Pig Hearts", Transplantation, 1994, vol. 58, pp. 330-337.
Burdorf et al., "Day Xeno Lung Recipient Survival—Progress towards the Clinic," Journal of Heart and Lung Transplantation, Apr. 2019, 38(4):S39, 72.
Kemter et al., "Xeno-organ donor pigs with multiple genetic modifications—the more the better?", Current Opinion in Genetics & Development, Jun. 30, 2020, 64:60-65.
Niu et al., "Porcine genome engineering for xenotransplantation," Advanced Drug Delivery Reviews, 2021, 168:229-245.

(56) References Cited

OTHER PUBLICATIONS

Pierson et al., "Progress Toward Cardiac Xenotransplantation," Circulation, 142(14):1389-1398.

Beaton et al., "GGTA-1 targeting efficiency with a xenograft transgene", 2012, retrieved from https://mospace.umsystem.edu/xmlui/handle/10355/35385# on Aug. 31, 2022.

Kim et al., "Knock-in Somatic Cells of Human Decay Accelerating Factor and a1,2-Fucosyltransferase Gene on the a1,3-Galactosyltransferase Gene Locus of Miniature Pig", Reprod Dev Biol, 2015, 39(3):59-67.

Kim et al., "Porcine Knock-in Fibroblasts Expressing hDAF on a-1,3-Galactosyltransferase (GGTA1) Gene Locus", Asian-Aust. J. Anim. Sci., 2012, 25:1473-1480.

Cooper et al., "Clinical lung xenotransplantation—what donor genetic modifications may be necessary?", Xenotransplantation, 2012, 19:144-158.

Li et al., "Rosa26-targeted swine models for stable gene over-expression and Cre-mediated lineage tracing," Cell Research, 2014, 24:501-504.

Mohiuddin et al., "Chimeric 2C1OR4 anti-CD40 antibody therapy is critical for long-term survival of GTKO.ACD46.hTBM pig-to-primate cardiac xenograft," Nature Communications, vol. 7:11138, Apr. 5, 2016, pp. 1-10.

Cooper et al., "Experimental Pig Heart Xenotransplantation—Recent Progress and Remaining Problems," Ann. Thorac. Surg., Apr. 2019, 107(4):989-992.

d'Apice et al., "Xenotransplantation: The next generation of engineered animals," Transplant Immunology, 2009, 21:111-115.

Fischer et al., "Multi-transgenic pigs for xenotransplantation," Xenotransplantation, 2013, 20:64; Berlin Symposium on Xenotransplantation 2012—Abstracts.

Fisicaro et al., "Efficient co-expression of multiple graft-protective transgenes using the 2A system," Xenotransplantation, 2007, 14(4):383, Abstract 106.3.

Hinrichs et al., "Inactivation of the GHR gene—a strategy to overcome excess growth of orthotopic pig-to-baboon cardiac xenografts?", Xenotransplantation, 2017, 24(e12328):39-40, Abstract O.6.2, Abstracts of the 14th Congress of the International Xenotransplantation Association, Sep. 20-23, 2017, Baltimore, MD, https://doi.org/10.1111/xen.12328.

Hurh et al., "Expression Analysis of Combinatorial Genes Using a Bi-Cistronic T2A Expression System in Porcine Fibroblasts," PLoS One, Jul. 2013, 8(7):e70486, 1-11.

Phelps et al., "Production and characterization of transgenic pigs expressing porcine CTLA4-lg," Xenotransplantation, Nov-Dec. 2009, 16(6):477-485.

International Search Report and Written Opinion for PCT/US2016/051126 issued Feb. 7, 2017.

Deng, W et al. Use of a 2A Peptide for Generation of Multi-Transgenic Pigs through a Single Round of Nuclear Transfer. PLos One, May 13, 2011, vol. 5, No. 5; pp. 1-9; p. 1, col. 2, 2nd paragraph, p. 7, col. 2, 3rd paragraph; DOI.

Estrada, J.L. et al. Evaluation of Human and Non-Human Primate Antibody Binding to Pig Cells Lacking GGTA1/CMAH/b4GaINT2 genes; Xenotransplantation; Mar. 1, 2015; vol. 22, pp. 194-202; doi: 10.1111/xen.12161; Figure 4; abstract.

Hai, T. et al. One-Step Generation of Knockout Pigs by Zygote Injection of CRISPR/Cas System; Cell Research; Jan. 31, 2014; vol. 24, pp. 372-375; doi: 10.1038/cr.2014.1; p. 372, 1str column, 2nd-3rd paragraph.

Ulrichts, H. et al. Shielding of the Al Doman by the D D3 Domains of von Willebrand Factor Mod-ulates its Interaction with Platelet Glycoprotein Ib-IX-V*; The Journal of Biological Chemistry; Feb. 24, 2006; vol. 281, No. 8, pp. 4699-4707; DOI 10.1074/jbc.M513314200; p. 4701, col. 1, 5th paragraph.

* cited by examiner

Expression in Lung by IHC analysis

Wildtype Control pig

TBM,TFPI,EPCR,HO-1 pig

FIG. 7

Flow cytometric analysis of gene expression in a fetus with TBM.CD47.EPCR.HO-1 MCV targeted to the Gal locus (236C-1)

TBM

CD47

HO-1

EPCR

TBM quantitation in plasma by ELISA

CD55

CD

CD

CD201

G

CD141

0.2%

MULTI-TRANSGENIC PIG FOR XENOTRANSPLANTATION

CROSS REFERENCE TO RELATED APPLICATIONS

This application is a national stage application under 35 U.S.C. § 371 of International Application No. PCT/US2016/051126, filed Sep. 9, 2016, which claims the benefit of U.S. Provisional Patent Application 62/216,225, filed Sep. 9, 2015 and U.S. Provisional Patent Application 62/256,068, filed Nov. 16, 2015, the contents of which are herein incorporated by reference in their entirety.

BACKGROUND OF THE INVENTION

Pigs have been the focus of most research in xenotransplantation, as pigs share many anatomical and physiological characteristics in common with human. Pigs also have relatively short gestation periods, can be bred in pathogen-free environments and may not present the same ethical issues associated with animals not commonly used as food sources (e.g., primates). Scientific knowledge and expertise in the field of pig-to-primate xenotransplantation has grown rapidly over the last decade, resulting in the considerably prolonged survival of primate recipients of lifesaving porcine xenografts. (Cozzi et al., Xenotransplantation, 16:203-214. 2009). Recently, significant achievements have been reported in the field of organ xenotransplantation. (Ekser et al., 2009, Transplant Immunology Jun, 21(2):87-92).

Significant progress has been made to overcome the biologic barriers to use of pig organs in preclinical models, with sustained organ function and recipient survival reaching months to years in some heart and kidney series (Mohiuddin M M, et al. Am J Transplant 2014; 14:488-489; Iwase H, et al. Xenotransplantation 2015; 22:302-309. Higginbotham L et al. Xenotransplantation 2015; 22:221-230). However, the progress to date while significant for the heart and kidney has not yet reached the point to be translated to humans. In addition, other organs, such as lung, represent an even larger challenge. For example, life-supporting lung xenograft survival has been limited to days in primates (Laird et al. June 2016, www.cotransplantation.com, Vol 21. No. 3).

Lung transplantation is an accepted treatment for advanced stage lung disease. First performed in 1963, more than 32,000 lung transplants have since been carried out worldwide. The majority of procedures are cadaveric transplants, in which the donor lung is obtained patient that is brain-dead but still on life support. Limitations in the number of cadaveric donor lungs lead to the development of living donor lobar lung transplantation (LDLLT) in the 1990's, in which two or more living patients donate a segment (lobe) of their lung. However, the donor pool remains relatively scare and long-term outcomes of transplantation remain hampered by immunosuppressive regimens.

Xenotransplantation (transplant of organs, tissues and cells from a donor of a different species) could effectively address the shortage of human donor lungs. Advantageously, xenotransplants are (i) supplied on a predictable, non-emergency basis; (ii) produced in a controlled environment; and (iii) available for characterization and study prior to transplant. However, compared with other organs, the unique anatomic structure of the lung, with a large surface area of vascular endothelium intimately associated with alveolar epithelium and a robust immune surveillance and rapid response system, are primed to trigger inflammation and are extremely susceptible to its consequences (den Hengst W A et al Am J Physiol Heart Circ Physiol 2010; 299:H1283-H1289; Ranieri V M et al JAMA 1999; 282:54-61).

While advantageous in many ways, xenotransplantation creates a more complex immunological scenario than allotransplantation The most profound barrier to pig-to-primate xenotransplantation is the rejection of the grafted organ by a cascade of immune mechanisms, divided into three phases: hyperacute rejection (HAR), acute humoral xenograft rejection (AHXR), and T-cell mediated cellular rejection. HAR is a very rapid event that results in irreversible graft damage and loss within minutes to hours following graft reperfusion.

Considerable effort has been directed at addressing the immune barrier posed by xenotransplantation through genetic modification of the donor animal. Genetically modified pigs lacking alpha-1,3-Gal epitopes (the major xenoantigens triggering HAR of pig-to-primate xenografts) are considered to be the basis for further genetic modifications that can address other rejection mechanisms and incompatibilities between the porcine and primate blood coagulation systems. While multiple genetic modifications are likely necessary for successful xenotransplantation, they present challenge including production-related challenges. It is clear that the generation of transgenic pigs that stably express multiple immune-modulating transgenes is essential to overcoming xenograft rejection.

The generation of multitransgenic pigs by traditional breeding of pigs that contain single transgenes has been utilized thus far with much success (Ekser et al., 2009, Transplant Immunology Jun 21(2):87-92; Laird et al. June 2016, www.cotransplantation.com, Vol 21. No. 3). However, breeding is time-consuming, expensive and consistent expression levels of the transgenes can be an issue over time.

Recently, the use of polycistronic expression systems have been developed to insert multiple transgenes into various cell types and animals. The feasibility of generating multitransgenic pigs using these systems has been suggested.

Deng et al. (PLOS ONE, www.plosone.org, May 2011, Vol 6, Issue 5, e19986) produced transgenic pigs expressing four fluorescent proteins using the 2A peptide bicistronic system and nuclear transfer via random integration of the transgenes.

Jeong et al. (PLOS ONE, www.plosone.org, May 2013, Vol 8, Issue 5, e63241) reported the production of transgenic pigs expressing the complement regulatory factor CD59 and H-transferase genes using an IRES-mediated tricistronic vector system and nuclear transfer. Jeong et al, actually attempted to express three genes using this tricistronic system, however, despite being present in the IRES vector, the third gene, CD55, was not expressed in the pigs.

Hurh et al (PLOS ONE, www.plosone.org, July 2013, Vol 8, Issue 7, e70486) generated transgenic porcine fibroblasts using a bi-cistronic T2A expression system and analyzed expression of the transgenic proteins using this system. They reported that efficient expression of a downstream gene can be achieved if the expression of the upstream gene is efficient.

Multitransgenic pigs using polycistronic expression systems that result in stable, sufficient integration and expression of transgenes have not yet been produced. Thus, it remains to be established whether this strategy represents a viable alternative to the traditional breeding approaches typically employed to generate multitransgenic pigs.

There remains a need for improved donor animals for xenotransplantation therapies.

In particular, there remains a need for donor animals that can provide lung xenografts having improved functionality.

SUMMARY OF THE INVENTION

The present invention is directed to transgenic animals (e.g., transgenic porcine animals) comprising multiple genetic modifications that advantageously render these animals suitable donors for xenotransplanation. The present invention extends to organs, organ fragments, tissues and cells derived from these animals and their therapeutic use. The present invention further extends to methods of making such animals.

In a first aspect, the present invention provides a transgenic pig comprising at least four transgenes, wherein the at least four transgenes are incorporated and expressed at a single locus under the control of at least two promoters, and wherein the pig lacks expression of alpha 1, 3 galactosyltransferase.

The single locus may be any suitable locus. In one embodiment, the single locus is a native locus, unmodified. In an alternate embodiment, the single locus is a modified native locus. The locus may be modified by any suitable means including but not limited to insertions, deletions, or substitutions mediated by gene-editing tools. In certain embodiments, the modified native locus includes transgenic DNA. The transgenic DNA may be, for example, a selectable marker gene. In order embodiments, the transgenic DNA is a landing pad—as described further herein.

In particular embodiments, the single locus is AAVS1, ROSA26, CMAH, ß4GalNT2 or GGTA1. According to this embodiment, this locus may be native or modified.

In an exemplary embodiment, the single locus is native GGTA1 or modified native GGTA1. In certain embodiments, the modified native GGTA1 locus includes a selectable marker gene, for example neo. In other embodiments, the modified native GGTA1 locus includes insertions, deletions or substitutions mediated by gene-editing tools. In yet other embodiments, the modified native GGTA1 locus includes a landing pad to facilitate gene targeting.

The promoters may vary. In exemplary embodiments, the promoters are endogenous, exogenous or a combination thereof. In exemplary embodiments, the promoters are constitutive or regulatable or a combination thereof. In certain embodiments, at least one of the promoters is regulatable (e.g., a tissue-specific or inducible promoter).

In an exemplary embodiment, the transgenic pig comprises four transgenes, wherein the four transgenes are expressed as a first and second polycistron, and wherein a first promoter controls expression of the first polycistron and a second promoter controls expression of the second polycistron.

In an exemplary embodiment, the transgenic pig comprises four transgenes, wherein each of the at least four transgenes is controlled by a dedicated promoter.

In a particular embodiment, the transgenic pig comprises at least four transgenes, wherein the at least four transgenes are incorporated and expressed at a single locus under the control of at least two promoters, wherein at least one of the promoters is constitutive (e.g., CAM) and at least one of the promoters is tissue-specific (e.g., an endothelial-specific promoter, such as ICAM-2), and wherein the pig lacks expression of alpha 1, 3 galactosyltransferase.

In another particular embodiment, the transgenic pig comprises at least four transgenes, wherein the at least four transgenes are incorporated and expressed at a single locus under the control of at least two promoters, wherein at least two of the promoters are constitutive and wherein the pig lacks expression of alpha 1, 3 galactosyltransferase.

The transgenes may vary. In exemplary embodiments, the transgenes are anti-coagulants, compliment inhibitors, immunomodulators, cytoprotective transgenes or combinations thereof.

In certain embodiments, at least one of the transgenes is an anti-coagulant. In one embodiment, the anti-coagulant is TBM, TFPI, EPCR, or CD39. In a particular embodiment, at least two of the transgenes are anti-coagulants.

In certain embodiment, at least one of the transgenes is a compliment regulator, such as a compliment inhibitor. In one embodiment, the compliment inhibitor is CD46, CD55 or CD59.

In certain embodiments, at least one of the transgenes is an immunomodulator. The immunomodulator may be, for example, an immunosuppressant. In one embodiment, the immunosuppressant is porcine CLTA4-IG or CIITA-DN. In a particular embodiment, at least one of the transgenes is CD47.

In exemplary embodiment, the transgenic animal comprises at least one additional genetic modification, i.e., in addition to expression of multiple transgenes and lack of expression of alpha Gal.

The additional genetic modification may vary. In exemplary embodiments, the at least one genetic modification is a gene knock-out, gene knock-in, gene replacement, point mutations, deletions, insertions or substitutions of genes, gene fragments or nucleotides, large genomic insertions, or combinations thereof.

In certain embodiments, the single locus is not GGTA1 and the at least one additional genetic modification comprises knock-out of the alpha 1, 3 galactosyltransferase gene.

In other embodiments, the additional genetic modification involves incorporation and expression of at least one additional transgene. In one embodiment, the additional transgenes is a human CD46 gene, human HLA-3 and/or a humanized vWF or chimeric porcine-human vWF gene.

In certain embodiments, the at least one additional genetic modification is a modification of the porcine vWF locus to reduce or eliminate spontaneous aggregation of human platelets.

In certain embodiments, the at least one additional genetic modification is a knock-out of a porcine gene. The porcine gene may be, in certain embodiments, ß4GalNT2, CMAH, isoGloboside 3 synthase, Forrsman synthase or vWF.

In certain embodiments, the at least one additional genetic modification involves incorporation and expression of at least two or more additional transgenes. In one embodiment, the two or more additional transgenes are incorporated and expressed a single, second locus.

In an exemplary embodiment, the transgenic pig comprising at least six transgenes, wherein the (i) at least four transgenes are incorporated and expressed at a first single locus (e.g., GGTA1) under the control of at least two promoters and (ii) at least two transgenes are incorporated and expressed under the control of at least one promoter at a second single locus (e.g., ß4GalNT2 or CMAH), and wherein the pig lacks expression of alpha 1, 3 galactosyltransferase.

In a second aspect, the present invention is an organ or organ fragment derived from the transgenic pig of the first aspect of the invention.

In exemplary embodiments, the organ is a lung, liver, heart or pancreas.

In exemplary embodiments, the organ fragment is a lung fragment, liver fragment, heart fragment or pancreas fragment.

In a third aspect, the present invention is a tissue derived from the transgenic pig of the first aspect of the invention.

In exemplary embodiments, the tissue is an epithelial tissue or a connective tissue.

In a fourth aspect, the present invention is a cell derived from the transgenic pig disclosed herein.

In exemplary embodiments, the cell is an islet cell.

In a fifth aspect, the present invention is a method of making a transgenic pig expressing at least four transgenic genes but lacking expression of alpha 1, 3 galactosyltransferase, comprising (i) incorporating at least four transgenes under the control of at least two promoters at a single locus within a pig genome to provide a polygene pig genome; (ii) permitting a cell comprising the polygene pig genome to mature into a transgenic pig.

In an exemplary embodiment, the pig genome is a somatic cell pig genome and the cell is a pig zygote, and wherein the pig zygote is provided by somatic cell nuclear transfer (SCNT) and transferring the polygene pig genome by microinjection into a reconstructed SCNT zygote. Optionally, the somatic cell genome and/or the polygene pig genome may include one or more additional genetic modifications. In one embodiment, the at least one genetic modification is selected from a is a gene knock-out, gene knock-in, gene replacement, point mutations, deletions, insertions or substitutions of genes, gene fragments or nucleotides, large genomic insertions, or combinations thereof.

In an exemplary embodiment, the pig genome is a selected from the group consisting of a gamete pig genome, zygote pig genome, an embryo pig genome or a blastocyst pig genome. Optionally, the pig genome or the polygene pig genome comprises at least one additional genetic modification. In one embodiment, the at least one genetic modification is selected from a is a gene knock-out, gene knock-in, gene replacement, point mutations, deletions, insertions or substitutions of genes, gene fragments or nucleotides, large genomic insertions, or combinations thereof.

The method of incorporation may vary. In exemplary embodiment, incorporation involves biological transfection, chemical transfection, physical transfection, virus mediated transduction or transformation or combinations thereof. In a particular embodiment, incorporation involves cytoplasmic microinjection. In another particular embodiment, incorporation involves pronuclear microinjection.

The single locus may vary, consistent with the first aspect of the invention.

In exemplary embodiments, the single locus includes transgenic DNA. In a particular embodiment, the transgenic DNA is a landing pad that includes one or more recognition sites for at least one polynucleotide modification enzyme. The polynucleotide modification enzyme may vary. In certain embodiments, the polynucleotide modification enzyme is an engineered endonucleases, site specific recombinases, integrases or combinations thereof.

In one embodiment, the engineered endonuclease is a zinc finger nuclease, transcription activator-like effector nucleases or a, a clustered regularly interspaced short palindromic repeats/Cas9 nucleases.

In one embodiment, the site specific recombinase is a lambda integrase, Cre recombinase, FLP recombinase, gamma-delta resolvase, Tn3 resolvase, ΦC31 integrase, Bxb1-integrase, R4 integrase or combinations thereof.

In one embodiment, the single locus is a native or modified locus selected from GGTA1, CMAH, ß4GalNT2, AAVS1 locus and Rosa26.

In embodiments where the single locus is not a GGTA1 locus and the additional genetic modification comprises knocking-out the alpha 1, 3 galactosyltransferase gene. Other knock-outs contemplated by the present invention as additional genetic modifications include knock-outs of the porcine ß4GalNT2 gene, CMAH gene, ß4GalNT2 gene, vWF or combinations thereof.

In exemplary embodiments, the at least one additional genetic modification involves incorporation and expression of at least one additional transgene. In certain embodiments, the transgene is human CD46, human HLA-E, a humanized vWF, a chimeric porcine-human vWF, or a fully human vWF.

In a sixth aspect, the present invention is a transgenic pig or production herd produced by the method of the fifth aspect of the invention.

In a seventh aspect, the present invention is a method of breeding the transgenic pig of the present invention to a second transgenic pig, wherein the second transgenic pig is characterized by one or more genetic modifications.

In exemplary embodiments, the second transgenic pig is characterized by one or more genetic modifications such as gene knock-out, gene knock-in, gene replacement, point mutations, deletions, insertions or substitutions of genes, gene fragments or nucleotides, large genomic insertions, or combinations thereof.

In an eighth aspect, the present invention is a transgenic pig or production herd produced by the method of the seventh aspect of the invention.

In a ninth aspect, the present invention provides a method for treating a subject in need thereof, by implanting into the subject at least one organ, organ fragment, tissue or cell derived from the transgenic pig of the present invention.

In exemplary embodiments, the organ or organ fragment is a lung or lung fragment, a kidney or kidney fragment, a liver or liver fragment, a pancreas or pancreas fragment or combination thereof.

In a particular embodiment, the organ is a lung. In another particular embodiment, the organ fragment is a lung fragment. In an exemplary embodiment, the lung or lung fragment is implanted in a subject having advanced lung disease.

In an exemplary embodiment, the lung or lung fragment is implanted in a subject having advanced lung disease associated with chronic obstructive pulmonary disease (COPD), idiopathic pulmonary fibrosis (IPD), cystic fibrosis (CF), alpha1-antitrypsin disease, or primary pulmonary hypertension.

In certain embodiments, the method involves administering one or more additional therapeutic agents to the subject. The one or more therapeutic agents may vary. In one embodiment, the therapeutic agent is an anti-rejection agent, an anti-inflammatory agent, an immunosuppressive agent, an immunomodulatory agent, an anti-microbial agent, and anti-viral agent and combinations thereof.

In a tenth aspect, the present invention provides a transgenic pig having a genetic modification of the porcine vWF locus, and lacking expression of alpha 1, 3 galactosyltransferase. The transgenic pig may comprise one or more additional genetic modifications.

In an exemplary embodiment, the transgenic pig has a genetic modification of the porcine vWF locus and incorporates and expresses at least four transgenes, as well as lacks expression of alpha 1, 3 galactosyltransferase.

DESCRIPTION OF THE FIGURES

FIG. 1 B depicts a docking vector useful in the present invention, including globin insulators flanking and separating insertion sites for two bi-cistronic units driven by independent promoter/enhancers.

FIG. 7 depicts expression analysis of pREV967 transgenes in lung.

FIG. 11 B depicts flow cytometry expression of all transgenes in fetal MVEC cells from pREV971 targeted to the alpha Gal locus.

DETAILED DESCRIPTION

Figure 1:
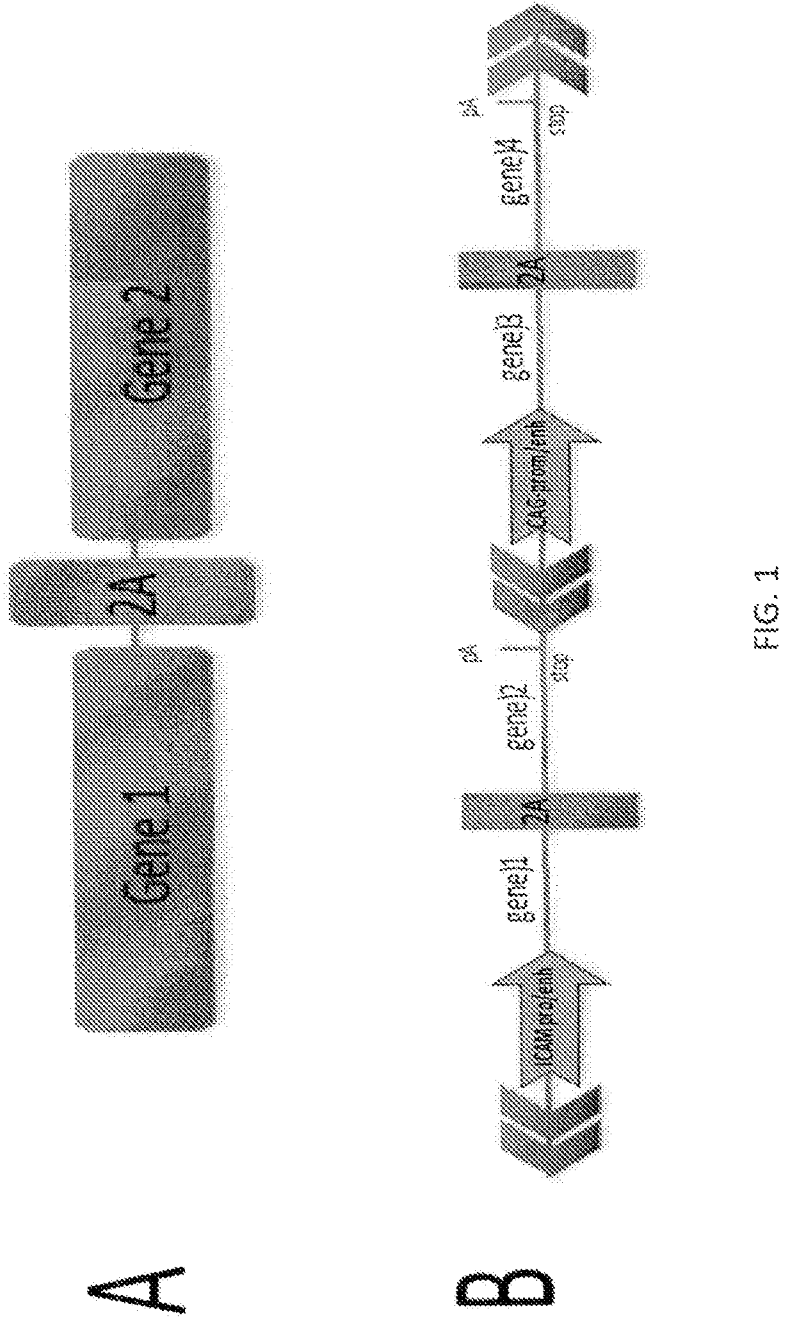
FIG. 1 A depicts a bicistronic unit of a vector useful in the present invention, consisting of two transgenes linked by a 2A peptide sequence.

The present invention is directed to transgenic animals that are particularly useful as a source of organs, organ fragments, tissues or cells for xenotransplantation. In particular, the invention is directed to transgenic ungulates, and more particularly, transgenic porcine animals (pigs), useful as a source of organs, organ fragments, tissues or cells for xenotransplantation. The invention also extends to the organs, organ fragments, tissues or cells derived from such donor animals, methods of producing such donor animals, as well as the use of organs, organ fragments, tissues or cells derived from such animal in the treatment of diseases and disorders.

Advantageously, the donor animals provide organs, organ fragments, tissues and cells that are functionally superior in a transplant (tx) context to organs, organ fragments, tissues and cells known in the art. Without wishing to be bound by any particular theory, it is believed that the organs, organ fragments, tissues and cells of the present invention have improved survival and/or functionality due to a noticeable reduction of consumptive coagulopathy (also known as disseminated intravascular coagulation (DIC)), and thrombotic microangiopathy currently observed following discordant xenotransplantation.

The organ or organ fragment may be any suitable organ, for example, a lung, heart, liver or pancreas. The tissue may be any suitable tissue, for example, epithelial or connective tissue. The cell may be any suitable cell. The cell may be any suitable cell, for example, an islet cell.

In exemplary embodiments, the present invention provides a transgenic animal (e.g., ungulate, porcine animal) particularly useful as a source of organs (i.e., lungs), organ fragments, tissues or cells for lung xenotransplantation, and extends to organs (i.e., lungs), organ fragments, tissues and cells derived therefrom, as well as methods of producing the transgenic animal and methods of using the organs, tissues and cells derived therefrom for lung xenotransplantation.

Advantageously, organs, organ fragments, tissues or cells derived from the transgenic animal, following xenotransplanation, produce low to no levels of one or more of the following: hyperacute rejection (HAR), acute humoral rejection (AHXR/DXR) and/or acute cellular xenograft rejection (ACXR).

In one embodiment, organs, organ fragments, tissues or cells derived from the transgenic animal produce low to no levels of HAR and AHXR following xenotransplantation. In another embodiment, organs, organ fragments, tissues or cells derived from the transgenic animal produce low to no levels of HAR, AHXR and ACXR following xenotransplantation.

In exemplary embodiments, the transgenic animal is a porcine animal which lacks any expression of functional alpha 1,3 galactosyltransferase (alpha Gal) (as the result of genetic modification or otherwise) and incorporates at least several additional genetic modifications (e.g., gene knockouts, gene knock-ins, gene replacements, point mutations, deletions, insertions, or substitutions (i.e., of genes, gene fragments or nucleotides), large genomic insertions or combinations thereof). The genetic modifications may be mediated by any suitable technique, including for example homologous recombination or gene editing methods.

In exemplary embodiments, the transgenic animal is a porcine animal which lacks any expression of functional alpha 1,3 galactosyltransferase (alpha Gal) (as the result of genetic modification or otherwise) and incorporates and expresses at least four transgenes, under control of at least two promoters, at a single locus. In certain embodiments, one promoter controls expression of one transgene, e.g., expression of each of the at least four transgenes is controlled by a single (dedicated) promoter. In alternative embodiments, one promoter controls expression of more than one transgene, e.g., one promoter controls expression of two transgenes. Advantageously, the four or more transgenes are co-integrated, co-expressed and co-segregate during breeding. The single locus may vary. In certain embodiments, the single locus is a native or modified native locus. The modified native locus may be modified by any suitable technique, including, but not limited to, CRISP-induced insertion or deletion (indel), introduction of a selectable marker gene (e.g., neo) or introduction of a large genomic insert (e.g., a landing pad) intended to facilitate incorporation of one or more transgenes. In a particular embodiment, the single locus is a native or modified GGTA1 locus. The GGTA1 locus is inactivated by incorporation and expression of the at least four transgenes, for example by homologous recombination, application of gene editing or recombinase technology. The single locus may also be, for example, AAVS1, ROSA26, CMAH, or ß4GalNT2 Optionally, the transgenic animal may have one or more additional genetic modifications and/or the expression of one or more additional porcine genes may be modified by a mechanism other than genetic modification In exemplary embodiments, the transgenic animal is a porcine animal which lacks any expression of functional alpha 1,3 galactosyltransferase (alpha Gal) (as the result of genetic modification or otherwise) and incorporates and expresses at least three, at least four, at least five, at least six, at least seven, at least eight, at least nine, or at least ten transgenes or more at a single locus. In certain embodiments, expression of the at least three, at least four, at least five, at least six, at least seven, at least eight, at least nine, or at least ten transgenes or more is controlled by at least two, at least three, at least four, at least five, at least six, at least seven, at least eight, at least nine, or at least ten promoters or more. In certain embodiments, the promoter is dedicated to the transgene, i.e., one promoter controls expression of one transgene, while in alternative embodiments, one promoter controls expressions of more than one transgene, e.g., one promoter controls expression of two transgenes. Advantageously, the two or more additional transgenes are co-integrated, co-expressed and co-segregate during breeding. The single locus may vary. In certain embodiments, the single locus is a native or modified native locus. The modified native locus may be modified by any suitable technique, including, but not limited to, CRISP-induced insertion or deletion (indel), introduction of a selectable marker gene (e.g., neo) or introduction of a large genomic insert (e.g., a landing pad) intended to facilitate incorporation of one or more transgenes. In a particular embodiment, the single locus is a native or modified GGTA1 locus. The GGTA1 locus is inactivated by incorporation and expression of the at least four transgenes, for example by homologous recombination, application of gene editing or recombinase technology. The single locus may also be, for example, AAVS1, ROSA26, CMAH, or ß4GalNT2. Optionally, the donor animal may have additional genetic modifications and/or the expression of one or more additional porcine genes may be modified by a mechanism other than genetic modification In exemplary embodiments, the transgenic animal is a porcine animal which lacks any expression of functional alpha 1,3 galactosyltransferase (alpha Gal) (as the result of genetic modification or otherwise) and incorporates and expresses at least four transgenes at a single locus (i.e., locus 1) also incorporates and expresses one or more additional transgenes at a second single locus (i.e., locus 2). In certain embodiments, one promoter controls expression of one transgene, e.g., expression of each of the at least four transgenes at locus 1 or locus 2 is controlled by a single (dedicated) promoter. In alternative embodiments, one promoter controls expression of more than one transgene, e.g., one promoter controls expression of two transgenes at locus 1. The particular loci may vary. In a particular embodiment, the first single locus is GGTA1 and the second single locus is, for example, CMAH, B4GalNT2 or vWF. In a particular embodiment, at least four transgenes are incorporated and expressed at each single locus, i.e., locus 1 and locus 2, to produce an animal with eight or more transgenes expressed at two distinct and independent loci. In certain embodiments, the single locus is a native or modified native locus. The modified native locus may be modified by any suitable technique, including, but not limited to, CRISP-induced insertion or deletion (indel), introduction of a selectable marker gene (e.g., neo) or introduction of a large genomic insert (e.g., a landing pad) intended to facilitate incorporation of one or more transgenes. Optionally, the donor animal may have additional genetic modifications and/or the expression of one or more additional porcine genes may be modified by a mechanism other than genetic modification. Advantageously, the two or more additional transgenes are co-integrated, co-expressed and co-segregate during breeding.

The at least two promoters may vary. The promoter may be exogenous or native. In exemplary embodiments, the promoters are constitutive or regulatable (e.g., tissue-specific, inducible). In one embodiment both promoters could be constitutively or ubiquitously expressed in the donor animal (e.g. from a CAG or similar promoter). In another embodiment with two promoters, one promoter would permit expression of transgenes in a tissue specific manner (e.g. endothelial specific expression), while the second promoter would permit expression of one or more transgenes (at the same integration site) in a constitutive or ubiquitous manner (e.g. from a CAG or similar promoter).

In certain embodiments, the additional genetic modification (i.e. apart from the incorporation and expression of the multiple transgenes described above) may result in inactivation of a particular porcine gene, including, but not limited to, the porcine von Willebrand Factor (vWF) gene, or replacement of some or all of the porcine vWF gene with equivalent counterparts from the human vWF gene. Other genes that may be inactivated in connection with the additional genetic modifications include, for example, CMP-NeuAc hydroxylase (CMAH), the isoGloboside 3 synthase, ß4Gal,NT2 Forrsman synthase or combinations thereof. In certain embodiments, there the single locus for transgene incorporation is not GGTA1, the additional genetic modifications encompass inactivation of GGTA1.

In certain embodiments, the additional genetic modification is, for example, a gene editing-induced deletions/insertions or gene substitutions (INDELs).

In certain embodiments, the additional genetic modification (i.e. apart from the incorporation and expression of the multiple transgenes described above) may result in incorporation and expression of one or more transgenes at a second locus.

In one embodiment, the present invention is a porcine animal which lacks any expression of functional alpha 1,3 galactosyltransferase (alpha Gal) (as the result of genetic modification or otherwise) and further comprises inactivation of the porcine von Willebrand Factor (vWF) gene, or replacement of some or all of the porcine vWF gene with equivalent counterparts from the human vWF gene. Optionally, the porcine animal comprises one or more additional genetic modifications. In certain embodiments, this animal may be bred with a second animal containing one or more genetic modifications.

The present invention also extends to methods of making and using such transgenic animals (or organs, tissues or cells derived therefrom).

In exemplary embodiments, the present invention provides a method of making a transgenic pig expressing at least four transgenic genes but lacking expression of alpha 1, 3 galactosyltransferase, comprising (i) incorporating at least four transgenes under the control of at least two promoters at a single locus within a pig genome to provide a polygene pig genome; (ii) permitting a cell comprising the polygene pig genome to mature into a transgenic pig.

In certain embodiments, the pig genome is a somatic cell pig genome and the cell is a pig zygote.

In certain embodiments, the pig genome is a selected from the group consisting of a gamete pig genome, zygote pig genome, an embryo pig genome or a blastocyst pig genome.

In exemplary embodiments, incorporating comprises a method selected from the group consisting of biological transfection, chemical transfection, physical transfection, virus mediated transduction or transformation or combinations thereof.

In certain embodiments, incorporating comprises cytoplasmic microinjection and pronuclear microinjection.

In exemplary embodiments, the methods involve use of bi- or multi-cistronic vectors that permit the transgenes to be co-integrated and co-expressed, with functional and/or production advantages, including multicistronic vectors utilizing 2A technology. In a preferred embodiment each bicistron, within a multicistronic vector containing at least four transgenes, is under control of its own promoter, and one or both promoters might result in constitutive expression of two or more genes, and the second promoter might result in tissue specific expression of two or more genes. These vectors are utilized in combination with genetic editing tools, including editing nucleases and/or site-specific integrases.

The present invention also extends to method of treating a subject in need thereof with one or more organs, organ fragments, tissues or cells derived from a transgenic animal of the present invention. In exemplary embodiments, the organ is a liver, lung, heart, pancreas or other solid organs. Examples of tissues contemplated by the present invention include, without limitation, epithelial and connective tissues.

Transplants involving more than one organ or organ fragment are also contemplated by the invention. For example transplants involving a lung (or lung fragment) and heart (or fragment thereof) are contemplated by the present invention.

Definitions

As used herein, the term “adverse event” refers to any unfavorable or unintended sign (including an abnormal laboratory finding, for example), symptom, or disease temporarily associated with the use of a medicinal product (e.g., a xenotransplant), whether or not considered related to the medical product.

As used herein, the term “animal” refers to a mammal. In specific embodiments, the animals are at least six months old. In certain embodiments, the animals is past weaning age. In certain embodiments, the animal survives to reach breeding age. The animals of the invention are “genetically modified” or “transgenic,” which means that they have a transgene, or other foreign DNA, added or incorporated, or an endogenous gene modified, including, targeted, recombined, interrupted, deleted, disrupted, replaced, suppressed, enhanced, or otherwise altered, to mediate a genotypic or phenotypic effect in at least one cell of the animal and typically into at least one germ line cell of the animal. In some embodiments, the animal may have the transgene integrated on one allele of its genome (heterozygous transgenic). In other embodiments, animal may have the transgene on two alleles (homozygous transgenic).

As used herein, the term “breeding” or “bred” or derivatives thereof refers to any means of reproduction, including both natural and artificial means.

As used herein, the term “breeding herd” or “production herd” refers to a group of transgenic animals generated by the methods of the present invention. In some embodiments, genetic modifications may be identified in animals that are then bred together to form a herd of animals with a desired set of genetic modifications (or a single genetic modification). See WO 2012/112586; PCT/US2012/025097 These progeny may be further bred to produce different or the same set of genetic modifications (or single genetic modification) in their progeny. This cycle of breeding for animals with desired genetic modification(s) may continue for as long as one desires. "Herd" in this context may comprise multiple generations of animals produced over time with the same or different genetic modification(s). "Herd" may also refer to a single generation of animals with the same or different genetic modification(s).

As used herein, the term "CRISPR" or "Clustered Regularly Interspaced Short Palindromic Repeats" or "SPIDRs" or "SPacer Interspersed Direct Repeats" refers to a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. CRISPR/Cas molecules are components of a prokaryotic adaptive immune system that is functionally analogous to eukaryotic RNA interference, using RNA base pairing to direct DNA or RNA cleavage. Directing DNA DSBs requires two components: the Cas9 protein, which functions as an endonuclease, and CRISPR RNA (crRNA) and tracer RNA (tracrRNA) sequences that aid in directing the Cas9/RNA complex to target DNA sequence (Makarova et al., Nat Rev Microbiol, 9(6):467-477, 2011). The modification of a single targeting RNA can be sufficient to alter the nucleotide target of a Cas protein. In some cases, crRNA and tracrRNA can be engineered as a single cr/tracrRNA hybrid to direct Cas9 cleavage activity (Jinek et al., Science, 337(6096):816-821, 2012). The CRISPR/Cas system can be used in bacteria, yeast, humans, and zebrafish, as described elsewhere (see, e.g., Jiang et al., Nat Biotechnol, 31(3):233-239, 2013; Dicarlo et al., Nucleic Acids Res, doi:10.1093/nar/gkt135, 2013; Cong et al., Science, 339(6121):819-823, 2013; Mali et al., Science, 339 (6121):823-826, 2013; Cho et al., Nat Biotechnol, 31(3): 230-232, 2013; and Hwang et al., Nat Biotechnol, 31(3): 227-229, 2013).

As used herein, the term "clinically relevant immunosuppressive regimen" refers to a clinically acceptable regimen of immunosuppressant drugs provided to a patient following organ, tissue or cell transplantation of a genetically modified pig as disclosed herein. Determining clinical relevance requires a judgment call generally by the FDA balancing acceptable risk versus potential benefit such that human safety is preserved while the efficacy of the drug or treatment is maintained.

As used herein, the term "constitutive" promoter refers to a nucleotide sequence which, when operably linked with a polynucleotide which encodes or specifies a gene product, causes the gene product to be produced in a cell under most or all physiological conditions of the cell.

As used herein, the term "donor" is meant to include any non-human animal that may serve as a source of donor organs, tissue or cells for xenotransplantation. The donor may be in any stage of development, including, but not limited to fetal, neonatal, young and adult.

As used herein, the term "endogenous" as used herein in reference to nucleic acid sequences and an animal refers to any nucleic acid sequence that is naturally present in the genome of that animal. An endogenous nucleic acid sequence can comprise one or more gene sequences, intergenic sequences, portions of gene sequences or intergenic sequences, or combinations thereof.

As used herein, the terms "endothelial-specific", "specific transgene expression in endothelial tissue", "specifically expresses at least one transgene in endothelial tissue" and the like, it is understood that these terms refer to a transgene under control of an endothelial-specific regulatory element that allows for the restricted expression of a transgene in endothelial tissue and/or cells. The transgene function and expression is restricted to endothelial tissue and/or cells.

As used herein, the term "endothelium" is an epithelium of mesoblastic origin composed of a single layer of thin flattened cells that lines internal body cavities. For example, the serous cavities or the interior of the heart contain an endothelial cells lining and the "vascular endothelium" is the endothelium that lines blood vessel.

As used herein, the term "endothelial-specific regulatory element" and the like refer to a promoter, enhancer or a combination thereof wherein the promoter, enhancer or a combination thereof drives restricted expression of a transgene in endothelial tissue and/or cells. The regulatory element provides transgene function and expression restricted to endothelial tissue and/or cells.

As used herein, the term "enhancer" is refers to an element in a nucleic acid construct intended to facilitate increased expression of a transgene in a tissue-specific manner. Enhancers are outside elements that drastically alter the efficiency of gene transcription (Molecular Biology of the Gene, Fourth Edition, pp. 708-7 1 0, Benjamin Cummings Publishing Company, Menlo Park, CA © 1987). In certain embodiments, the animal expresses a transgene under the control of a promoter in combination with an enhancer element. In some embodiments, the promoter is used in combination with an enhancer element which is a non-coding or intronic region of DNA intrinsically associated or co-localized with the promoter.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The term "gene" is used herein broadly to refer to any segment of DNA associated with a biological function. Thus, genes include coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "gene editing" refers a type of genetic engineering in which DNA is inserted, replaced, or removed from a genome using gene editing tools. Examples of gene editing tools include, without limitation, zinc finger nucleases, TALEN and CRISPR.

As used herein, the term "gene-editing mediated" or similar terms refers to a modification of the gene (e.g., a deletion, substitution, re-arrangement) that involves the use of gene-editing/gene-editing tools.

As used herein, the term "gene knock-out" refers to a genetic modification resulting from the disruption of the genetic information encoded in a chromosomal locus.

As used herein, the term "gene knock-in" is a genetic modification resulting from the replacement of the genetic information encoded in a chromosomal locus with a different DNA sequence.

The term "genetic modification" as used herein refers to one or more alterations of a nucleic acid, e.g., the nucleic acid within an organism's genome. For example, genetic modification can refer to alterations, additions (e., gene knock-ins), and/or deletion of genes (e.g., gene knock-outs).

As used herein, the term "high" with reference to levels of expression refers to a level of expressed considered sufficient to provide a phenotype (detectable expression or therapeutic benefit). Typically a 'high' level of expression is sufficient to be capable of reducing graft rejection including hyperacute rejection (HAR), acute humoral xenograft rejection (AHXR), T cell-mediated cellular rejection and immediate blood-mediated inflammatory response (IBMIR).

As used herein, the term "homology driven recombination" or "homology direct repair" or "HDR" is used to refer to a homologous recombination event that is initiated by the presence of double strand breaks (DSBs) in DNA (Liang et al. 1998); and the specificity of HDR can be controlled when combined with any genome editing technique known to create highly efficient and targeted double strand breaks and allows for precise editing of the genome of the targeted cell; e.g. the CRISPR/Cas9 system (Findlay et al. 2014; Mali et al. February 2014; and Ran et al. 2013).

As used herein, the term "enhanced homology driven insertion or knock-in" is described as the insertion of a DNA construct, more specifically a large DNA fragment or construct flanked with homology arms or segments of DNA homologous to the double strand breaks, utilizing homology driven recombination combined with any genome editing technique known to create highly efficient and targeted double strand breaks and allows for precise editing of the genome of the targeted cell; e.g. the CRISPR/Cas9 system. (Mali et al. February 2013).

As used herein, the term "humanized" refers to nucleic acids or proteins whose structures (i.e., nucleotide or amino acid sequences) include portions that correspond substantially or identically with structures of a particular gene or protein found in nature in a non-human animal, and also include portions that differ from that found in the relevant particular non-human gene or protein and instead correspond more closely with comparable structures found in a corresponding human gene or protein. In some embodiments, a "humanized" gene is one that encodes a polypeptide having substantially the amino acid sequence as that of a human polypeptide (e.g., a human protein or portion thereof—e.g., characteristic portion thereof). The term "hyperacute rejection" refers to rejection of a transplanted material or tissue occurring or beginning within the first 24 hours after transplantation.

The term "implant" or "transplant" or "graft" as used herein shall be understood to refer to the act of inserting tissue or an organ into a subject under conditions that allow the tissue or organ to become vascularized; and shall also refer to the so-inserted (i.e. "implanted" or "transplanted" or "grafted") tissue or organ. Conditions favoring vascularization of a graft in a mammal comprise a localized tissue bed at the site of the graft having an extensive blood supply network.

As used herein, the term "immunomodulator" refers to a transgene with the ability to modulate the immune responses. In exemplary embodiments, an immunomodulator according to the present invention can be a complement inhibitor or an immunosuppressant. In specific embodiments, the immunomodulator is a complement inhibitor. The complement inhibitor can be CD46 (or MCP), CD55 CD59 and/or CRI. In a specific embodiment, at least two complement inhibitors can be expressed. In one embodiment, the complement inhibitors can be CD55 and CD59. In another embodiment, the immunomodulator can be a class II transactivator or mutants thereof. In certain embodiments, the immunomodulator can be a class II transactivator dominant negative mutant (CIITA-DN). In another specific embodiment, the immunomodulator is an immunosuppressant. The immunosuppressor can be CTLA4-Ig. Other immunomodulators can be selected from the group but not limited to CIITA-DN, PDL I, PDL2, or tumor necrosis factor-α related-inducing ligand (TRAIL), Fas ligand (FasL, CD95L) CD47, known as integrin-associated protein (CD47), HLA-E, HLA-DP, HLA-DQ, and/or HLA-DR.

As used herein, an "inducible" promoter is a promoter which is under environmental or developmental regulation.

As used herein, the term "landing pad" or "engineered landing pad" refers to a nucleotide sequence containing at least one recognition sequence that is selectively bound and modified by a specific polynucleotide modification enzyme such as a site-specific recombinase and/or a targeting endonuclease. In general, the recognition sequence(s) in the landing pad sequence does not exist endogenously in the genome of the cell to be modified. The rate of targeted integration may be improved by selecting a recognition sequence for a high efficiency nucleotide modifying enzyme that does not exist endogenously within the genome of the targeted cell. Selection of a recognition sequence that does not exist endogenously also reduces potential off-target integration. In other aspects, use of a recognition sequence that is native in the cell to be modified may be desirable. For example, where multiple recognition sequences are employed in the landing pad sequence, one or more may be exogenous, and one or more may be native. Multiple recognition sequences may be present in a single landing pad, allowing the landing pad to be targeted sequentially by two or more polynucleotide modification enzymes such that two or more unique sequences can be inserted. Alternatively, the presence of multiple recognition sequences in the landing pad, allows multiple copies of the same sequence to be inserted into the landing pad. A landing pad may comprise at least one recognition sequence. For example, an exogenous nucleic acid may comprise at least one, at least two, at least three, at least four, at least five, at least six, at least seven, at least eight, at least nine, or at least ten or more recognition sequences. In embodiments comprising more than one recognition sequence, the recognition sequences may be unique from one another (i.e. recognized by different polynucleotide modification enzymes), the same repeated sequence, or a combination of repeated and unique sequences. Optionally, the landing pad may include one or more sequences encoding selectable markers such as antibiotic resistance genes, metabolic selection markers, or fluorescence proteins. Other sequences, such as transcription regulatory and control elements (i.e., promoters, partial promoters, promoter traps, start codons, enhancers, introns, insulators and other expression elements) can also be present.

As used herein, the term "large targeting vector" or "LTVEC" includes large targeting vectors for eukaryotic cells that are derived from fragments of cloned genomic DNA larger than those typically used by other approaches intended to perform homologous gene targeting in eukaryotic cells. Examples of LTVEC, include, but are not limited to, bacterial artificial chromosome (BAC), a human artificial chromosome (HAC), and yeast artificial chromosome (YAC).

As used herein, the term "genomic locus" or "locus" (plural loci) is the specific location of a gene or DNA sequence on a chromosome, and can include both intron or exon sequences of a particular gene. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, introns, exons, promoter sequences, terminators, translational regulatory sequences such as ribosome binding sites and internal ribosome entry sites, enhancers, silencers, insulators, boundary elements, 5' or 3' regulatory sequences, replication origins, matrix attachment sites and locus control regions.

As used herein, the term "lung transplantation" refers to a surgical procedure in which a patient's diseased lungs are partially or totally replaced by lungs which come from a donor. Lung transplantation may be "single", in which just one of the two lungs is removed in the recipient and replaced with a single lung from the donor or "bilateral" which involves removing both lungs, one on each side and replacing both the lungs from the donor. In certain embodiments, the lung is transplanted together with a heart.

As used herein the term "lung preservation" refers to the process of maintaining and protecting a donor lung from the time of lung procurement up until implantation in the recipient has occurred.

As used herein, the phrase "loss of transplant function", as used herein, refers to any physiological disruption or dysfunction of the normal processes the organ or tissue exhibits in the donor animal.

As used herein, the term "mammal" refers to any non-human mammal, including but not limited to pigs, sheep, goats, cattle (bovine), deer, mules, horses, monkeys, dogs, cats, rats, and mice. In certain embodiments, the animal is a porcine animal of at least 300 pounds. In specific embodiments, the mammal is a porcine sow and has given birth at least one time. In certain embodiments, the mammal is a non-human primate, e.g., a monkey or baboon.

As used herein, a "marker" or a "selectable marker" is a selection marker that allows for the isolation of rare transfected cells expressing the marker from the majority of treated cells in the population. Such marker's gene's include, but are not limited to, neomycin phosphotransferase and hygromycin B phosphotransferase, or fluorescing proteins such as GFP.

As used herein, the term "nucleotide", "polynucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, the phrase "operably linked" comprises a relationship wherein the components operably linked function in their intended manner. In one instance, a nucleic acid sequence encoding a protein may be operably linked to regulatory sequences (e.g., promoter, enhancer, silencer sequence, etc.) so as to retain proper transcriptional regulation The term "organ" as used herein refers to is a collection of tissues joined in a structural unit to serve a common function. The organ may be a solid organ. Solid organs are internal organs that has a firm tissue consistency and is neither hollow (such as the organs of the gastrointestinal tract) nor liquid (such as blood). Examples of solid organs include the heart, kidney, liver, lungs, pancreas, spleen and adrenal glands.

As used herein, the term "primate" refers to of various mammals of the order Primates, which consists of the lemurs, lorises, tarsiers, New World monkeys, Old World monkeys, and apes including humans, and is characterized by nails on the hands and feet, a short snout, and a large brain. In certain embodiments, the primate is a non-human primate. In other embodiments, the primate is a human.

As used herein, the term "promoter" refers to a region of DNA, generally upstream (5') of a coding region, which controls at least in part the initiation and level of transcription. Reference herein to a "promoter" is to be taken in its broadest context and includes the transcriptional regulatory sequences of a classical genomic gene, including a TATA box or a non-TATA box promoter, as well as additional regulatory elements (i.e., activating sequences, enhancers and silencers) that alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene, although they may also be many kb away. Promoters may contain additional specific regulatory elements, located more distal to the start site to further enhance expression in a cell, and/or to alter the timing or inducibility of expression of a structural gene to which it is operably connected.

As used herein, the terms "porcine", "porcine animal", "pig" and "swine" are generic terms referring to the same type of animal without regard to gender, size, or breed.

As used herein, the term "recognition site" or "recognition sequence" refers to a specific DNA sequence recognized by a nuclease or other enzyme to bind and direct site-specific cleavage of the DNA backbone.

As used herein, the term "recombination site" refers to a nucleotide sequence that is recognized by a site-specific recombinase and that can serve as a substrate for a recombination event.

As used herein, the terms "regulatory element" and "expression control element" are used interchangeably and refer to nucleic acid molecules that can influence the transcription and/or translation of an operably linked coding sequence in a particular environment. These terms are used broadly and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells may include, without limitation, promoters, enhancers, splicing signals and polyadenylation signals.

As used herein, the term "regulatable promoter" refers to a promoter that can be used to regulate whether the peptide is expressed in the animal, tissue or organ. The regulatable promoter could be tissue specific and only expressed in a specific tissue, or temporally regulatable (turned on at a specific time (driven by developmental stage), or inducible such that is only turned on or off (expressed or not) as controlled by inducible elements. (can also be inducible promoters such as immune inducible promoter and cytokine response promoters. eg. induced by interferon gamma, TNF-alpha, IL-1, IL-6 or TGF-beta) For example, expression can be prevented while the organ or tissue is part of the pig, but expression induced once the pig has been transplanted to the human for a period of time to overcome the cellular immune response. In addition, the level of expression can be controlled by a regulatable promoter system to ensure that immunosuppression of the recipient's immune system does not occur.

As used herein, the terms "regulatory sequences," "regulatory elements," and "control elements" are interchangeable and refer to polynucleotide sequences that are upstream (5' non-coding sequences), within, or downstream (3' non-translated sequences) of a polynucleotide target to be expressed. Regulatory sequences influence, for example, the timing of transcription, amount or level of transcription, RNA processing or stability, and/or translation of the related structural nucleotide sequence. Regulatory sequences may include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like.

The term "safe harbor" locus as used herein refers to a site in the genome where transgenic DNA (e.g., a construct) can be added without harm and produce a consistent level expression. In certain embodiments, the present invention involves incorporation and expression of transgenic DNA includes transgenes within a safe harbor locus.

As used herein, the term "site-specific recombinase" refers to group of enzymes that can facilitate recombination between "recombination sites" where the two recombination sites are physically separated within a single nucleic acid molecule or on separate nucleic acid molecules. Examples of "site-specific recombinase" include, but are not limited to, phiC31, att, Bxb1, R4 (integrases) and or, Cre, Flp, and Dre recombinases.

As used herein, the term "subject" refers to any animal (e.g., a mammal), including, but not limited to, humans, non-human primates, rodents, and the like (e.g., that is to be the recipient of a particular treatment (e.g., transplant graft) or that is a donor of a graft. The terms "subject" and "patient" are used interchangeably in reference to a human subject, unless indicated otherwise herein (e.g., wherein a subject is a graft donor).

As used herein, the term "targeting vector" refers to a recombinant DNA construct typically comprising tailored DNA arms homologous to genomic DNA that flanks critical elements of a target gene or target sequence. When introduced into a cell, the targeting vector integrates into the cell genome via homologous recombination. A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

As used herein, the term "tissue" refers to cellular organizational level intermediate between cells and a complete organ. A tissue is an ensemble of similar cells from the same origin that together carry out a specific function. Organs are then formed by the functional grouping together of multiple tissues. Examples of tissues contemplated by the present invention include, without limitation, connective tissue, muscle tissue, nervous tissue, epithelial tissue and mineralized tissue. Blood, bone, tendon, ligament, adipose and areolar tissues are examples of connective tissues—which may also be classified as fibrous connective tissue, skeletal connective tissue, and fluid connective tissue. Muscle tissue is separated into three distinct categories: visceral or smooth muscle, found in the inner linings of organs; skeletal muscle, typically attached to bones and which generates gross movement; and cardiac muscle, found in the heart where it contracts to pump blood throughout an organism. Cells comprising the central nervous system and peripheral nervous system are classified as nervous (or neural) tissue. In the central nervous system, neural tissues form the brain and spinal cord. In the peripheral nervous system, neural tissues forms the cranial nerves and spinal nerves, inclusive of the motor neurons.

The term transcription activator-like effector nucleases or "TALEN" as used herein refers to artificial restriction enzymes generated by fusing the TAL effector DNA binding domain to a DNA cleavage domain. These reagents enable efficient, programmable, and specific DNA cleavage and represent powerful tools for genome editing in situ. Transcription activator-like effectors (TALEs) can be quickly engineered to bind practically any DNA sequence. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA. See U.S. Ser. No. 12/965,590; U.S. Ser. No. 13/426,991 (U.S. Pat. No. 8,450,471); U.S. Ser. No. 13/427,040 (U.S. Pat. No. 8,440,431); U.S. Ser. No. 13/427,137 (U.S. Pat. No. 8,440,432); and U.S. Ser. No. 13/738,381, all of which are incorporated by reference herein in their entirety.

As used herein, the term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "transgene" is a gene or genetic material that has been transferred from one organism to another. When a transgene is transferred into an organism, the organism can then be referred to as a transgenic organism Typically, the term describes a segment of DNA containing a gene sequence that has been isolated from one organism and is introduced into a different organism. This non-native segment of DNA may retain the ability to produce RNA or protein in the transgenic organism, or it may alter the normal function of the transgenic organism's genetic code. In general, the DNA is incorporated into the organisms germ line. For example, in higher vertebrates this can be accomplished by injecting the foreign DNA into the nucleus of a fertilized ovum or via somatic cell nuclear transfer where a somatic cell, with the desired transgene(s) is incorporated into the host genome, is transferred to an enucleated oocyte and results in live offspring after transplantation into a surrogate mother. When inserted into a cell, a transgene can be either a cDNA (complementary DNA) segment, which is a copy of mRNA (messenger RNA), or the gene itself residing in its original region of genomic DNA. The transgene can be a genome sequence, in particular when introduced as large clones in BACs (bacterial artificial chromosomes) or cosmid, or could be a form of "minigene" often characterized by a combination of both genomic DNA (including intron regions, e.g. intron 1), 5' or 3' regulatory regions, along with cDNA regions. Transgene "expression" in the context of the present specification, unless otherwise specified, means that a peptide sequence from a non-native nucleic acid is expressed in at least one cell in a host. The peptide can be expressed from a transgene that is incorporated in the host genome. A transgene can comprise a polynucleotide encoding a protein or a fragment (e.g., a functional fragment) thereof. A fragment (e.g., a functional fragment) of a protein can comprise at least or at least about 5%, 10%, 20%, 30%, 40%, 50%, 60%, 70%, 80%, 90%, 95%, or 99% of the amino acid sequence of the protein. A fragment of a protein can be a functional fragment of the protein. A functional fragment of a protein can retain part or all of the function of the protein.

As used herein the term "transplant tolerance" is defined as a state of donor-specific unresponsiveness without a need for ongoing pharmacologic immunosuppression. Transplantation tolerance could eliminate many of the adverse events associated with immunosuppressive agents. As such, induction of tolerance may result in improved receipt of a xenograft. In an embodiment, induction of tolerance may be identified by a decrease in clinical symptoms of xenograft rejection. In another embodiment, induction of tolerance may ameliorate or prevent the metabolic, inflammatory and proliferative pathological conditions or diseases associated with xenograft transplantation. In still another embodiment, induction of tolerance may ameliorate or decrease or prevent the adverse clinical conditions or diseases associated with the administration of immunosuppressive therapy used to prevent xenograft rejection. In still yet another embodiment, induction of tolerance may promote xenograft survival. In a different embodiment, induction of tolerance may prevent relapses in patients exhibiting these diseases or conditions.

The term "ungulate" refers to hoofed mammals. Artiodactyls are even-toed (cloven-hooved) ungulates, including antelopes, camels, cows, deer, goats, pigs, and sheep. Perissodactyls are odd toes ungulates, which include horses, zebras, rhinoceroses, and tapirs. The term ungulate as used herein refers to an adult, embryonic or fetal ungulate animal.

The term "vector" as used herein refers to moiety which is capable of transferring a polynucleotide to a host cell. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, the contents of which are herein incorporated by reference in their entirety. Preferably the vector is a DNA vector and, more preferably, is capable of expressing RNA encoding a protein according to the invention. Numerous suitable vectors are documented in the art; examples may be found in Molecular Cloning: a Laboratory Manual: 2nd edition, Sambrook et al., 1989, Cold Spring Harbor Laboratory Press or DNA cloning: a practical approach, Volume II: Expression systems, edited by D. M. Glover (IRL Press, 1995).

As used herein, the term "zinc finger nuclease" or "ZFN" refers to an artificial (engineered) DNA binding protein comprising a zinc finger DNA-binding domain and aDNA-cleavage domain. Zinc finger domains can be engineered to target specific desired DNA sequences and this enables zinc-finger nucleases to target unique sequences within complex genomes. They facilitate targeted editing of the genome by creating double-strand breaks in DNA at user-specified locations. Each ZFN contains two functional domains: a.) A DNA-binding domain comprised of a chain of two-finger modules, each recognizing a unique hexamer (6 bp) sequence of DNA. Two-finger modules are stitched together to form a Zinc Finger Protein, each with specificity of ≥24 bp. b.) A DNA-cleaving domain comprised of the nuclease domain of Fok I. When the DNA-binding and DNA-cleaving domains are fused together, a highly-specific pair of 'genomic scissors' are created. ZFN are gene editing tools.

A. Transgenic Animals

The present invention provides a transgenic animal (e.g., a transgenic porcine animal) that serves as a source for organs, organ fragments, tissues or cells for use in xeno-transplantation. The present invention extends to the organs, tissues and cells derived from the transgenic animal, as well as groups of such animals, e.g., production herds.

The animal may be any suitable animal. In exemplary embodiments, the animal is an ungulate and more particularly, a porcine animal or pig.

The transgenic donor animal (e.g., ungulate, porcine animal or pig) is genetically modified and more particularly, comprises multiple transgenes, for example, multiple transgenes in a single locus. In certain embodiments, the transgenic donor animal is genetically modified to express multiple transgenes divided between a first locus (i.e., locus 1) and a second locus (i.e., locus 2).

The loci may be a native or modified native locus. Various strategies for modifying a native locus to facilitate targeting are described herein.

In exemplary embodiments, the present invention provides a transgenic animal (e.g., a transgenic porcine animal) comprising incorporation and expression of at least four transgenes at a single locus under the control of at least two promoters (e.g., exogenous promoters, or a combination of exogenous and native promoters), and wherein the pig lacks expression of alpha 1, 3 galactosyltransferase. Optionally, the transgenic animal comprises one or more additional genetic modifications, including, without limitation, additions and/or deletions of genes, including knock-outs and knock-ins, as well as gene substitutions and re-arrangements.

In a particular embodiment, the present invention provides a transgenic porcine animal comprising at least four transgenes incorporated and expressed at a single locus, wherein expression of the at least four transgenes is controlled by dedicated promoters, i.e., a promoter drives the expression of each individual transgene. For example, where the transgenic animal incorporates and expresses four transgenes in a single locus, the expression of those transgenes is drive by four promoters, where each promoter is specific to a particular transgene. In an alternative embodiment, a given promoter controls expression of more than one transgene (e.g., two transgenes, three transgenes). For example, where the transgenic animal incorporates and expresses four transgenes, two of the four transgenes are expressed as a polycistron controlled by a first promoter and two of the four transgenes are expressed as a polycistron controlled by the second promoter.

In exemplary embodiments, the at least four transgenes are selected from the group consisting of immunomodulators (e.g., immunosuppressants), anticoagulants, compliment inhibitors and cryoprotective transgenes.

In exemplary embodiments, the single locus is a native locus. In other embodiments, the single locus is a modified native locus, such as transgenic locus. The transgenic locus may be, for example, a locus containing a selectable marker gene or a locus containing a landing pad.

In exemplary embodiments, the at least four transgenes are provided in a multi-cistronic vector (MCV) and incorporated either by random integration, or by utilizing a gene editing tool. Optionally, the transgenic animal may have one or more additional genetic modifications. The additional genetic modification may be, for example, a gene knock-out or gene knock-in. In particular embodiments, the additional genetic modification comprises a chimeric porcine-human vWF.

In another embodiment, the present invention provides a transgenic animal (e.g., a pig) that includes at least five genetic modifications, resulting in (i) lack of expression of alpha 1, galactosyltransferase (i.e., is alpha Gal null) and (ii) incorporation and expression of at least four, at least five, at least six, at least seven, at least eight, at least nine or at least ten transgenes in a single locus. The expression of the transgenes is driven by a promoter, either a dedicated promoter or a promoter which controls expression of two or more transgenes. The promoters may be exogenous or a combination of exogenous and native promoters.

In certain embodiments, if greater than four added transgenes might involve incorporation of transgenes at more than one locus in order to better modulate expression of the transgene combination (eg. integration of at least four transgenes under control of at least two promoters integrated at GGTA1, and a second multicistronic integration at a second locus (eg. CMAH or B4GalNT2 or AAVS1 or Rosa26). In certain embodiments where a second locus is genetically modified such second locus could be modified to inactivate expression of another porcine gene (eg. through application of gene editing and/or homologous recombination technology). In exemplary embodiments, the multiple transgenes incorporated and expressed as the second locus are selected from the group consisting of immunomodulators, compliment inhibitors, anticoagulants and cryoprotective transgenes. In exemplary embodiments, the second locus is a native locus, a modified native locus or a transgenic locus (e.g., landing pad). In exemplary embodiments, the at least two transgenes at the second locus are provided in a MCV and incorporated utilizing a gene editing tool. Optionally, the transgenic animal may have one or more additional genetic modifications.

In one embodiment, the present invention provides a transgenic animal (e.g., a pig) that includes at least four genetic modifications, resulting in (i) reduced expression of alpha 1, galactosyltransferase and (ii) incorporation and expression of at least four transgenes in a single locus, where such four transgenes are expressed under control of at least two promoters (e.g., exogenous promoters or a combination of exogenous and native promoters). In exemplary embodiments, the transgene is selected from the group consisting of immunomodulators, anticoagulants, compliment inhibitors and cryoprotective transgenes. In exemplary embodiments, the single locus is a native locus, a modified native locus or a transgenic locus (e.g., landing pad). In exemplary embodiments, the at least two transgenes are provided in a MCV and incorporated utilizing a gene editing tool (ie. CRISPR/cas9, TALEN, or ZFN) to enhance the efficiency of homologous recombination or homology dependent repair. Optionally, the transgenic animal may have one or more additional genetic modifications.

In another embodiment, the present invention provides a transgenic animal (e.g., a pig) that includes at least five genetic modifications, resulting in (i) reduced expression of alpha 1, galactosyltransferase and (ii) incorporation and expression of at least four, at least five, at least six, at least seven, at least eight, at least nine or at least ten transgenes in a single locus, or divided between two loci. In exemplary embodiments, the transgene is selected from the group consisting of immunomodulators, compliment inhibitors, anticoagulants and cryoprotective transgenes. In exemplary embodiments, the single locus is a native locus, a modified native locus or a transgenic locus (e.g., landing pad). In exemplary embodiments, the at least two transgenes are provided in a MCV and incorporated utilizing a gene editing tool (ie. CRISPR/cas9, TALEN, or ZFN) to enhance the efficiency of homologous recombination or homology dependent repair. Optionally, the transgenic animal may have one or more additional genetic modifications.

In exemplary embodiments, the transgenic animal lacks expression of alpha 1, galactosyltransferase (i.e., is alpha Gal null) and comprises at least one, at least two, at least three, at least four, at least five, at least six or at least seven or more genetic modifications. Optionally, in addition to transgene integrations, additional knockouts include knockout of beta4GalNT2 gene or CMAH gene (both genes that have been implicated in cause of innate immunity and rejection of xenografts.

In exemplary embodiments, the transgenic animal has reduced expression of alpha 1, galactosyltransferase and comprises at least one, at least two, at least three, at least four, at least five, at least six or at least seven additional genetic modifications.

In certain embodiment, expression of alpha 1, galactosyltransferase is reduced by about 10%, about 20%, about 30%, about 40%, about 50%, about 60%, about 70%, about 80%, about 90% or about 95%.

In exemplary embodiments, the transgenic animal comprises (i) a genetic modification that results in lack of expression of alpha 1,3 galactosyltransferase and (ii) at least four additional genetic modifications, or more particularly four additional genetic modifications. These additional genetic modifications may be any suitable genetic modification, including but not limited to CRISPR-induced deletions/insertions or gene substitutions (INDELs) including knockout or knockin at other loci (e.g., B4GalNT2, CMAH, vWF).

In exemplary embodiments, the transgenic animal comprises (i) a genetic modification that results in reduced expression of alpha 1,3 galactosyltransferase and (ii) at least four additional genetic modifications, or more particularly four additional genetic modifications.

In exemplary embodiments, the transgenic animal comprises (i) a genetic modification that results in lack of expression of alpha 1,3 galactosyltransferase and (ii) at least five additional genetic modifications, or more particularly five additional genetic modifications.

In exemplary embodiments, the transgenic animal comprises (i) a genetic modification that results in reduced expression of alpha 1,3 galactosyltransferase and (ii) at least five additional genetic modifications, or more particularly, at least five additional genetic modifications.

In exemplary embodiments, the transgenic animal comprises (i) a genetic modification that results in lack of expression of alpha 1,3 galactosyltransferase and (ii) at least six additional genetic modifications, or more particularly six additional genetic modifications.

In exemplary embodiments, the transgenic animal comprises (i) a genetic modification that results in reduced expression of alpha 1,3 galactosyltransferase and (ii) at least six additional genetic modifications, or more particularly six additional genetic modifications.

In a particular embodiment, the donor animal (e.g., ungulate, porcine animal or pig) comprises genetic modifications that result in (i) lack of expression of alpha 1,3 galactosyltransferase and (ii) incorporation and expression of at least one, at least two, at least three, at least four, at least five, or at least six or more transgenes.

In exemplary embodiments, the present invention provides a porcine animal that comprises genetic modifications that result in (i) lack of expression of alpha 1,3 galactosyltransferase and (ii) incorporation and expression of at least four additional transgenes.

In exemplary embodiments, the present invention provides a porcine animal that comprises genetic modifications that result in (i) lack of expression of alpha 1,3 galactosyltransferase and (ii) incorporation and expression of at least five additional transgenes, or more particularly five additional genetic modifications.

In exemplary embodiments, the present invention provides a porcine animal that comprises genetic modifications that result in (i) lack of expression of alpha 1,3 galactosyltransferase and (ii) incorporation and expression of at least six additional transgenes, or more particularly six additional genetic modifications.

In a particular embodiment, the donor animal (e.g., ungulate, porcine animal or pig) comprises genetic modifications that result in (i) reduced expression of alpha 1,3 galactosyltransferase and (ii) incorporation and expression of at least four, at least five, or at least six or more transgenes, or more particularly four, five, or at least six additional transgenes In an exemplary embodiment, the donor animal (e.g., ungulate, porcine animal or pig) comprises genetic modifications that result in (i) reduced expression of alpha 1,3 galactosyltransferase and (ii) incorporation and expression of five additional transgenes. Optionally, the donor animal may contain or more additional genetic modifications.

In an exemplary embodiment, the donor animal (e.g., ungulate, porcine animal or pig) comprises genetic modifications that result in (i) reduced expression of alpha 1,3 galactosyltransferase and (ii) incorporation and expression of six additional transgenes. Optionally, the donor animal may contain one or more additional genetic modifications (knockouts, knockins, INDELs, modification of porcine vWF).

B. Transgene Expression

Expression of the transgene can be at any level, but in specific embodiments, the expression is at high levels.

A variety of promoter/enhancer elements may be used depending on the level and tissue-specific expression desired. The promoter/enhancer may be constitutive or inducible, depending on the pattern of expression desired. The promoters may be exogenous or native, or a combination of exogenous and native promoters.

In certain embodiments, the transgene is expressed from a constitutive or ubiquitous promoter. In certain other embodiments, the transgene is expressed from a tissue-specific or cell type specific promoter, or inducible promoter, and may include additional regulatory elements such as enhancers, insulators, matrix attachment regions (MAR) and the like.

In exemplary embodiments, the four or more transgenes are co-expressed. In exemplary embodiments, the four or more transgenes are expressed in approximately molar equivalents.

In exemplary embodiments, the transgene is expressed by a promoter primarily active in endothelial cells. In certain embodiments, expression of the transgene is controlled by a porcine Icam-2 enhancer/promoter.

In certain embodiments, expression of the transgene is controlled by a constitutive CAG promoter.

In certain embodiments, the transgenic animal is genetically modified to result in incorporation and expression of two or more transgenes, where at least one transgene is controlled by a constitutive promoter and at least one transgene is controlled by a tissue-specific promoter, or more particularly, a promoter primarily active in endothelial cells.

In exemplary embodiments, the transgenic animal is genetically modified to result in incorporation and expression of four or more transgenes in a single locus, where at least one transgene is controlled by a constitutive promoter and at least one transgene is controlled by a tissue-specific promoter, or more particularly, a promoter primarily active in endothelial cells.

The transgene can be any transgene suitable for use in modifying a donor animal (e.g., a porcine animal) for use in xenotransplantation. In exemplary embodiments, the transgene is selected from an immunomodulator (e.g., compliment regulator, compliment inhibitor, immunosuppressant), an anticoagulant, a cryoprotective gene or combinations thereof. In certain embodiments, the sequence of the transgene in human.

In certain embodiments, the transgene is an immunomodulator.

In certain embodiments, the transgene is a compliment regulator or more specifically, a compliment inhibitor. The compliment inhibitor may include, without limitation, CD46 (MCP), CD59 or CR1. The sequence of the compliment inhibitor may be human.

In certain embodiments, the transgene is a compliment pathway inhibitor (i.e., a compliment inhibitor) inhibitor. The compliment inhibitor may include, without limitation, CD55, CD59, CR1 and CD46 (MCP). The sequence of the compliment inhibitor may be human.

In certain embodiments, the transgene is an immunosuppressant.

The complement inhibitor can be human CD46 (hCD46) wherein expression is through a mini-gene construct (See Loveland et al., Xenotransplantation, 11(2):171-183. 2004).

In certain embodiments, the transgene is an immunosuppressor gene that has a T-cell modulating effect—such as CTLA4-Ig, or a dominant negative inhibitor of class II MEW (CIITA), or other genes that modulate the expression of B-cell or T cell mediated immune function. In further embodiments, such animals can be further modified to eliminate the expression of genes which affect immune function. In certain embodiments, the immunosuppressor is CD47.

In certain embodiments, the transgene is an anticoagulant. The anticoagulant may include, without limitation, tissue factor pathway inhibitor (TFPI), hirudin, thrombomodulin (TBM), endothelial protein C receptor (EPCR), and CD39. The sequence of the anticoagulant may be human.

The transgenic animal may contain one or more additional genetic modification, as well.

In one embodiment, the animal may be genetically modified to inhibit the expression of the CMP-Neu5Ac hydroxylase gene (CMAH) (see, for example, U.S. Patent Publication. 2005-0223418), the iGb3 synthase gene (see, for example, U.S. Patent Publication 2005-0155095), and/or the Forssman synthase gene (see, for example, U.S. Patent Publication 2006-0068479). In addition, the animals can be genetically modified to reduce expression of a pro-coagulant. In particular, in one embodiment, the animals are genetically modified to reduce or eliminate expression of a procoagulant gene such as the FGL2 (fibrinogen-like protein 2) (see, for example, Marsden, et al. (2003) J din Invest. 112:58-66; Ghanekar, et al. (2004) J. Immunol. 172:5693-701; Mendicino, et al. (2005) Circulation. 112:248-56; Mu, et al. (2007) Physiol Genomics. 31(1):53-62).

In another embodiment, the animal may be genetically modified to inhibit the expression of beta-1,4 N-acetylgalactosaminyltransferase 2 (ß4GalNT2).

C. Specific Genetics

1. Alpha 1,3 Galactosyltransferase (alpha.Gal)

In one embodiment, the present invention provides a transgenic animal suitable for use as a source of organs, tissues and cells for xenotransplantation, wherein the donor animal lacks expression of alpha Gal or expression has been reduced. The transgenic animal that lacks expression of alpha Gal (i.e., is alpha Gal null) has one or more additional genetic modifications, and in certain embodiments, at least four additional genetic modifications, at least five additional genetic modifications or at least six additional genetic modifications. These genetic modifications may be, for example, incorporation or expression of transgenes. In a particular embodiment, the transgenic animal has at least three genetic modifications, resulting in (i) lack of expression of alpha Gal; and (ii) incorporation and expression of at least two transgenes in a single locus. In certain embodiments, the single locus is modified alpha Gal.

A variety of strategies have been implemented to eliminate or modulate the anti-Gal humoral response caused by xenotransplantation, including enzymatic removal of the epitope with alpha-galactosidases (Stone et al., Transplantation 63: 640-645, 1997), specific anti-gal antibody removal (Ye et al., Transplantation 58: 330-337, 1994), capping of the epitope with other carbohydrate moieties, which failed to eliminate .alpha.GT expression (Tanemura et al., J. Biol. Chem. 27321: 16421-16425, 1998 and Koike et al., Xenotransplantation 4: 147-153, 1997) and the introduction of complement inhibitory proteins (Dalmasso et al., Clin. Exp. Immunol. 86:31-35, 1991, Dalmasso et al. Transplantation 52:530-533 (1991)). C. Costa et al. (FASEB J 13, 1762 (1999)) reported that competitive inhibition of .alpha.GT in transgenic pigs results in only partial reduction in epitope numbers. Similarly, S. Miyagawa et al. (J. Biol. Chem. 276, 39310 (2000)) reported that attempts to block expression of gal epitopes in N-acetylglucosaminyltransferase III transgenic pigs also resulted in only partial reduction of gal epitopes numbers and failed to significantly extend graft survival in primate recipients.

Single allele knockouts of the alpha Gal locus in porcine cells and live animals have been reported. Denning et al. (Nature Biotechnology 19: 559-562, 2001) reported the targeted gene deletion of one allele of the .alpha.GT gene in sheep. Harrison et al. (Transgenics Research 11: 143-150, 2002) reported the production of heterozygous .alpha.GT knock out somatic porcine fetal fibroblasts cells. In 2002, Lai et al. (Science 295: 1089-1092, 2002) and Dai et al. (Nature Biotechnology 20: 251-255, 2002) reported the production of pigs, in which one allele of the .alpha.GT gene was successfully rendered inactive, and where inactivation of alpha Gal was through targeted insertion of the marker gene, neomycin phosphotransferase (Neo), that interrupted the coding region of the alpha Gal gene (Ramsoondar et al. (Biol of Reproduc 69, 437-445 (2003)) reported the generation of heterozygous .alpha.GT knockout pigs that also express human alpha-1,2-fucosyltransferase (HT), which expressed both the HT and alpha Gal epitopes. PCT publication No. WO 03/055302 to The Curators of the University of Missouri confirms the production of heterozygous alpha Gal knockout miniature swine for use in xenotransplantation in which expression of functional .alpha.GT in the knockout swine is decreased as compared to the wildtype.

PCT publication No. WO 94/21799 and U.S. Pat. No. 5,821,117 to the Austin Research Institute; PCT publication No. WO 95/20661 to Bresatec; and PCT publication No. WO 95/28412, U.S. Pat. Nos. 6,153,428, 6,413,769 and US publication No. 2003/0014770 to BioTransplant, Inc. and The General Hospital Corporation provide a discussion of the production of .alpha.GT negative porcine cells based on the cDNA of the .alpha.GT gene. A major breakthrough in the field of xenotransplantation was the production of the first live pigs lacking any functional expression of alpha Gal (Phelps et al. Science 299:411-414 (2003); see also PCT publication No. WO 04/028243 by Revivicor, Inc. and PCT Publication No. WO 04/016742 by Immerge Biotherapeutics, Inc.).

In one embodiment, animals (and organs, tissues and cells derived therefrom) are provided from a transgenic animal (e.g., a transgenic pig) comprising at least four transgenes, wherein the four transgenes are incorporated and expressed at a single locus under the control of at least two promoters, and wherein the pig lacks expression of alpha 1, 3 galactosyltransferase. In an exemplary embodiments, the transgenes are incorporated and expressed at a modified alpha Gal locus. In certain embodiments, the at least two promoters are exogenous, native or a combination of exogenous and native.

In one embodiment, animals (and organs, tissues and cells derived therefrom) are provided that (i) lack any expression of functional alpha Gal and (ii) incorporate and express at least four, at least five, at least six, at least seven, at least eight, at least nine or at least ten or more transgenes at a single locus. In an exemplary embodiments, the transgenes are incorporated and expressed at a modified alpha Gal locus.

In certain embodiments, the animal may include one or more additional genetic modifications. These genetic modifications may result in incorporation and expression of one or more additional transgenes at the same locus or a different locus.

In one embodiment, animals (and organs, tissues and cells derived therefrom) are provided that lack any expression of functional alpha Gal and incorporate and express at least one, at least two, at least three, at least four, at least five, or at least six additional transgenes.

In another embodiment, animals, organs, tissue and cells are provided that have a reduced level of expression of functional alpha Gal and incorporate and express at least one, at least two, at least three, at least four, at least five, or at least six additional transgenes. The expression of functional alpha Gal may be reduced by, for example, by at least about 5%, about 10%, about 20%, about 30%, about 40%, about 50%, about 60%, about 70%, about 80%, about 90% or about 95%.

The lack or reduced level of expression of functional alpha.GT may be achieved by any suitable means. In embodiment, animals (e.g., ungulates, porcine animals) are provided in which one allele of the alpha Gal gene is inactivated via a genetic targeting event. In another embodiment, porcine animals are provided in which both alleles of the alpha Gal gene are inactivated via a genetic targeting event. In one embodiment, the gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knock-out") or insertion ("knock-in") techniques, including targeted insertion of a selectable marker gene (e.g., neo) that interrupts the coding region of the alpha Gal gene. Additional genes for a desired protein or regulatory sequence that modulate transcription of an existing sequence can be inserted.

In certain embodiments, the alleles of the alpha Gal gene are rendered inactive, such that the resultant alpha Gal enzyme can no longer generate Gal on the cell surface. In one embodiment, the alpha Gal gene can be transcribed into RNA, but not translated into protein. In another embodiment, the alpha Gal gene can be transcribed in a truncated form. Such a truncated RNA can either not be translated or can be translated into a nonfunctional protein. In an alternative embodiment, the alpha Gal gene can be inactivated in such a way that no transcription of the gene occurs. In a further embodiment, the alpha Gal gene can be transcribed and then translated into a nonfunctional protein.

In some embodiments, the expression of active alpha Gal gene can be reduced by use of alternative methods, such as those targeting transcription or translation of the gene. For example, the expression can be reduced by use of antisense RNA or siRNA targeting the native .alpha.GT gene or an mRNA thereof. In other embodiments, site specific recombinases are used to target a region of the genome for recombination. Examples of such systems are the CRE-lox system and the Flp-Frt systems.

Pigs that possess two inactive alleles of the alpha Gal gene are not naturally occurring. It was previously discovered that while attempting to knockout the second allele of the alpha Gal gene through a genetic targeting event, a point mutation was identified, which prevented the second allele from producing functional alpha Gal enzyme.

Thus, in another aspect of the present invention, the alpha Gal can be rendered inactive through at least one point mutation In one embodiment, one allele of the alpha Gal gene can be rendered inactive through at least one point mutation. In another embodiment, both alleles of the alpha Gal gene can be rendered inactive through at least one point mutation. In one embodiment, this point mutation can occur via a genetic targeting event. In another embodiment, this point mutation can be naturally occurring. In a further embodiment, mutations can be induced in the alpha Gal gene via a mutagenic agent.

2. ß4GalNT2

In one embodiment, the present invention provides a transgenic animal suitable for use as a source of organs, tissues and cells for xenotransplantation, wherein the donor animal lacks expression of β1,4 N-acetyl-galactosaminyl transferase 2 (ß4GALNT2) or expression has been reduced. The transgenic animal that lacks expression of ß4GALNT2 (i.e., is ß4GALNT2 null) has one or more additional genetic modifications. These genetic modifications may be, for example, incorporation or expression of transgenes. In a particular embodiment, the transgenic animal which lacks expression of β1,4 N-acetyl-galactosaminyl transferase 2 (ß4GALNT2) or expression has been reduced is also characterized by (i) lack of expression of alpha Gal; and (ii) incorporation and expression of at least four transgenes in a single locus under the control of at least two promoters.

Glycans produced by ß4Gal-NT2 are xenoantigens for many humans. Estrada J L et al, Xenotransplantation 2015: 22: 194-202. In humans and mice, ß4GALNT2 catalyzes the addition of N-acetylgalactosamine to a sialic acid modified lactosamine to produce GalNAc b1-4(Neu5Ac a2-3) Gal b1-4GlcNAc b1-3Gal, the Sda blood group antigen. This gene is functional in transplantable organs (kidney, heart, liver, lung, and pancreas) and endothelial cells in the pig.

Approximately 5% of humans possess inactive ß4GalNT2 and consequently develop antibodies against the SDa and CAD carbohydrates produced by this gene. See Byrne G W et al. Transplantation 2011; 91: 287-292; Byrne G W, et al., Xenotransplantation 2014; 21: 543-554.

Any suitable method can be used to generate pigs whose genomes which lack or have reduced expression of endogenous ß4GALNT2. A disruption can be positioned at many sites in the endogenous porcine ß4GALNT2 nucleic acid sequence. Examples of disruptions include, but are not limited to, deletions in the native gene sequence and insertions of heterologous nucleic acid sequences into the native gene sequence. Examples of insertions can include, but are not limited to, artificial splice acceptors coupled to stop codons or splice donors coupled to fusion partners such as GFP. A knock-out construct can contain sequences that are homologous to the endogenous ß4GALNT2 nucleic add sequence or to sequences that are adjacent to the endogenous ß4GALNT2 nucleic acid sequence. In some cases, a knock-out construct can contain a nucleic acid sequence encoding a selection marker (e.g., antibiotic resistance, a fluorescent reporter (e.g., GFP or YIP), or an enzyme (e.g., β-galactosidase)) operatively linked to a regulatory sequence (e.g., a promoter). A knock-out construct can include other nucleic acid sequences such as recombination sequences (e.g., loxP sequences, see Sendai, et al, Transplantation, 81(5):760-766 (2006)), splice acceptor sequences, splice donor sequences, transcription start sequences, and transcription stop sequences. Disruptions in the endogenous ß4GALNT2 nucleic acid sequence can result in reduced expression of the gene or non-functional truncations or fusions of the encoded polypeptide.

In one embodiment, the present invention provides a transgenic animal (e.g., a porcine animal) expressing reduced or no of ß4GALNT2. Optionally, the animal comprises one or more additional genetic modifications.

In an exemplary embodiment, the present invention provides a transgenic animal (e.g., a porcine animal) incorporating and expression at least four transgenes under the control of at least two promoters, wherein the animal lacks or has reduced expression of ß4GALNT2. Optionally, the animal comprises one or more additional genetic modifications.

In one embodiment, the present invention provides a transgenic animal (e.g., a porcine animal) expressing reduced or no Sda or SDa-like glycans produced by porcine ß4GALNT2. Optionally, the animal comprises one or more additional genetic modifications.

In an exemplary embodiment, the present invention provides a transgenic animal (e.g., a porcine animal) incorporating and expression at least four transgenes under the control of at least two promoters, wherein the animal lacks or has reduced expression of no Sda or SDa-like glycans produced from a porcine ß4GALNT2. Optionally, the animal comprises one or more additional genetic modifications.

3. CMAH

In one embodiment, the present invention provides a transgenic animal suitable for use as a source of organs, tissues and cells for xenotransplantation, wherein the donor animal lacks expression of cytidine monophosphate-N-acetylneuraminic acid hydroxylase (CMAH), or expression has been reduced. The transgenic animal that lacks expression of CMAH is CMAH null) has one or more additional genetic modifications. These genetic modifications may be, for example, incorporation or expression of transgenes. In a particular embodiment, the transgenic animal has at least four additional genetic modifications, resulting in (i) lack of expression of alpha Gal; and (ii) incorporation and expression of at least four transgenes in a single locus.

Porcine cells express cytidine monophosphate-N-acetylneuraminic acid hydroxylase (CMAH), which are not found in human cells. CMAH converts the sialic acid N-acetylneuraminic acid (Neu5Ac) to N-glycolylneuraminic acid (Neu5Gc). As such, when porcine tissue is transplanted into a human, this epitopes elicit an antibody-mediated rejection from the human patient immediately following implantation. See Varki A. Am J Phys Anthropol 2001; (Suppl. 33):54-69; Zhu A. Xenotransplantation, 2002; 9: 376-381; Miwa Y. Xenotransplantation 2004; 11: 247-253; Tahara H. J Immunol 2010; 184: 3269-3275.

Any suitable method can be used to generate pigs whose genomes contain lack or have reduced expression of endogenous CMAH. A disruption can be positioned at many sites in the endogenous porcine CMAH nucleic acid sequence. Examples of disruptions include, but are not limited to, deletions in the native gene sequence and insertions of heterologous nucleic acid sequences into the native gene sequence. Examples of insertions can include, but are not limited to, artificial splice acceptors coupled to stop codons or splice donors coupled to fusion partners such as GFP. A knock-out construct can contain sequences that are homologous to the endogenous CMAH nucleic acid sequence or to sequences that are adjacent to the endogenous CMAH nucleic acid sequence. In some cases, a knock-out construct can contain a nucleic acid sequence encoding a selection marker (e.g., antibiotic resistance, a fluorescent reporter (e.g., GFP or YFP), or an enzyme (e.g., ß-galactosidase)) operatively linked to a regulatory sequence (e.g., a promoter). A knock-out construct can include other nucleic acid sequences such as recombination sequences (e.g., loxP sequences, see Sendai, et al, Transplantation, 81(5):760-766 (2006)), splice acceptor sequences, splice donor sequences, transcription start sequences, and transcription stop sequences. Disruptions in the endogenous CMAH nucleic acid sequence can result in reduced expression of the gene or non-functional truncations or fusions of the encoded polypeptide.

In one embodiment, the present invention provides a transgenic animal (e.g., a porcine animal) expressing reduced or no expression of CMAH glycosyltransferase. Optionally, the animal comprises one or more additional genetic modifications.

In an exemplary embodiment, the present invention provides a transgenic animal (e.g., a porcine animal) incorporating and expression at least four transgenes under the control of at least two promoters, wherein the animal lacks or has reduced expression of CMAH. Optionally, the animal comprises one or more additional genetic modifications.

4. vWF

The von Willebrand factor (vWF) gene is large and complex gene, with multiple domains, and that encodes a multimeric glycoprotein. (Ulrichts, H, Udvardy M, Lenting P J, Pareyn I et al. Shielding of the A1 domain by the D'D3 domains of von Willebrand Factor Modulates Its interaction with Platelet Glycoprotein 1b-IX-V. (2006) JBC 281, 4699-4707; Zhou Y-F, Eng E T, Zhu J, Lu C et all. Sequence and structure relationships within von Willebrand factor. (2012) Blood 120, 449-458). The main functions of the multimeric glycoprotein, von Willebrand factor (vWF), are platelet adhesion to connective tissues and sub-endothelium, as well as platelet aggregation as a function of the vWF binding to the platelet glycoprotein Ib (GPIb). However this phenomenon is less favorable during xenotransplantation when the aggregation of the recipient's platelets having a damaging effect on the survival of the donated organ. Per example, the transplantation of the porcine lungs (and other organs) to humans or non-human primates result in spontaneous aggregation and sequestration of human platelets. This can be avoided by "humanization" of the porcine VWF gene in an effort to eliminate this spontaneous binding of porcine vWF to human platelets.

In general, the humanization or modification to the porcine vWF gene requires the deletion of the gene sequence(s) associated with the spontaneous aggregation of human platelets and replacement with the human genetic counterpart that does not generate spontaneous aggregation. This could include deletion of all or part of the porcine vWF gene with replacement with all or part of the human vWF gene.

Modifications of porcine vWF aimed at elimination of the spontaneous platelet aggregation response could include regions within the D3 (partial), A1, A2, A3 (partial) domains that are known to be associated with folding and sequestration of the GPIb binding site in hvWF (D3 domain), as well as regions associated with the GPIb receptor (A1 domain) and the ADAMTS13 cleavage site (A2 domain). Exons 22-28 encompass these regions. Human platelets spontaneously aggregate in the presence of pig blood under normal stress forces. To avoid this potential threat to successful xenotransplantation, and since human vWF does NOT induce spontaneous platelet aggregation under conditions of normal shear stress in the blood, a region of the human vWF gene associated with folding of the vWF protein as well as regions associated with GPib binding, collagen binding (one of 2 regions), and ADAMTS13 cleavage could be utilized for replacement of the genomic homologs in the pig vWF gene (and resulting chimeric human/pig protein). In this way, alternate folding that could hide or mask the GPlb binding site on vWF, as well as a humanized receptor sites within the A domains could be provided with a single cDNA or genomic fragment from the human vWF gene. This could be achieved through homologous recombination or gene targeting, including where such mechanisms are enhanced utilizing gene editing methods (eg.,) CRISPR-assisted homologous recombination can be used to integrate a human vWF fragment into the porcine vWF locus. This human fragment replaces regions that are implicated in the spontaneous platelet aggregation mentioned above, and could be in the form of a cDNA or genomic fragment from the human vWF gene)

In exemplary embodiments, the insertion of the relevant human vWF gene sequences can be done by any current method used for genome editing, for example, but not limited to, CRISPR/CAS9, TALEN nucleases. The modification of the porcine vWF can be done by replacing only the relevant regions of the porcine vWF gene or alternatively, by replacing the entire pvWF gene with hvWF.

In one embodiment, a region of the porcine vWF gene may be replaced with the human counterpart (E22-E28 region). Alternatively, the transgenic animal may have a complete knockout of the vWF gene and full replacement of the gene synthetic sequence of the human vWVF gene using a site-specific recombination system (i.e. the CRE-LOX recombination system and/or by specific nucleic acid base pair changes to replace nucleotides in the porcine vWF genomic sequence with human counterparts.

In one embodiment, the present invention is a transgenic animal (e.g. a porcine transgenic animal) that lacks expression of alpha Gal, as well as a genetic modification to the porcine vWF gene. The modification may be, for example, a knock-out of the porcine vWF gene and replacement with a humanized or chimeric vWF gene. The transgenic animal may contain one more additional genetic modifications. In one embodiment, the transgenic animal further comprises incorporation and expression of CD46.

The transgenic animal may be bread to a second transgenic animal containing one or more genetic modifications, as well. For example, an invention is a transgenic animal (e.g. a porcine transgenic animal) that lacks expression of alpha Gal, as well as a genetic modification to the porcine vWF gene may be bread to a second transgenic animal containing at least four transgenes at a single locus or at least four transgenes at a single locus and at least two transgenes at a second locus, thereby providing an animal containing multiple genetic modifications.

In one embodiment, the present invention is a transgenic animal (e.g. a porcine transgenic animal) that lacks expression of alpha Gal, as well as a genetic modification to the porcine vWF gene (e.g., a chimeric human-porcine vWF) and at least four genetic modifications at a single locus under the control of at least two promoters. The locus may vary. In exemplary embodiments, the locus is a native locus or a modified native locus. The locus may be, for example, AAVS1, ROSA26, CMAH, ß4GalNT2 and GGTA1. The at least four transgenes may be incorporated by homologous recombination or a gene editing tools.

5. Transgenes

The transgene introduced into the genome of the transgenic animal of the present invention may be any suitable transgene.

(i) Immunodulators

In one embodiment, the transgene is an immunomodulator. In exemplary embodiments, the donor animal has been genetically modified with the result that (i) expression of alpha Gal is lacking or reduced and (ii) at least four transgenes are incorporated and expressed at a single locus, wherein at least one of the at least two transgenes is an immunomodulator.

The immunomodulator may be any suitable immunomodulator. In exemplary embodiments, the immunomodulator is a compliment regulator (e.g., a compliment inhibitor) or a immunosuppressant.

A. Compliment Regulators

In one embodiment, the present invention provides a transgenic animal (e.g., porcine animal) suitable for use as a source of organs, tissues and cells for xenotransplantation, wherein the donor animal has been genetically modified to incorporate and express at least one compliment regulator, e.g., a compliment inhibitor. In exemplary embodiments, the donor animal has been genetically modified with the result that (i) expression of alpha Gal is lacking or reduced and (ii) at least four transgenes are incorporated and expressed at a single locus, wherein at least one of the transgenes is a compliment regulator or more specifically, a compliment inhibitor.

Complement is the collective term for a series of blood proteins and is a major effector mechanism of the immune system. Complement activation and its deposition on target structures can lead to direct complement-mediated cell lysis or can lead indirectly to cell or tissue destruction due to the generation of powerful modulators of inflammation and the recruitment and activation of immune effector cells. Complement activation products that mediate tissue injury are generated at various points in the complement pathway. Inappropriate complement activation on host tissue plays an important role in the pathology of many autoimmune and inflammatory diseases, and is also responsible for many disease states associated with bio incompatibility, e.g. post-cardiopulmonary inflammation and transplant rejection. Complement deposition on host cell membranes is prevented by complement inhibitory proteins expressed at the cell surface.

The complement system comprises a collection of about 30 proteins and is one of the major effector mechanisms of the immune system. The complement cascade is activated principally via either the classical (usually antibody-dependent) or alternative (usually antibody-independent) pathways. Activation via either pathway leads to the generation of C3 convertase, which is the central enzymatic complex of the cascade. C3 convertase cleaves serum C3 into C3a and C3b, the latter of which binds covalently to the site of activation and leads to the further generation of C3 convertase (amplification loop). The activation product C3b (and also C4b generated only via the classical pathway) and its breakdown products are important opsonins and are involved in promoting cell-mediated lysis of target cells (by phagocytes and NK cells) as well as immune complex transport and solubilization. C3/C4 activation products and their receptors on various cells of the immune system are also important in modulating the cellular immune response. C3 convertases participate in the formation of C5 convertase, a complex that cleaves C5 to yield C5a and C5b. C5a has powerful proinflammatory and chemotactic properties and can recruit and activate immune effector cells. Formation of C5b initiates the terminal complement pathway resulting in the sequential assembly of complement proteins C6, C7, C8 and (C9)n to form the membrane attack complex (MAC or C5b-9). Formation of MAC in a target cell membrane can result in direct cell lysis, but can also cause cell activation and the expression/release of various inflammatory modulators.

There are two broad classes of membrane complement inhibitor: inhibitors of the complement activation pathway (inhibit C3 convertase formation), and inhibitors of the terminal complement pathway (inhibit MAC formation). Membrane inhibitors of complement activation include complement receptor 1 (CR1), decay-accelerating factor (DAF or CD55) and membrane cofactor protein (MCP or CD46). They all have a protein structure that consists of varying numbers of repeating units of about 60-70 amino acids termed short consensus repeats (SCR) that are a common feature of C3/C4 binding proteins. Rodent homologues of human complement activation inhibitors have been identified. The rodent protein Cr1 is a widely distributed inhibitor of complement activation that functions similar to both DAF and MCP. Rodents also express DAF and MCP, although Cr1 appears to be functionally the most important regulator of complement activation in rodents. Although there is no homolog of Cr1 found in humans, the study of Cr1 and its use in animal models is clinically relevant.

Control of the terminal complement pathway and MAC formation in host cell membranes occurs principally through the activity of CD59, a widely distributed 20 kD glycoprotein attached to plasma membranes by a glucosylphosphatidylinositol (GPI) anchor. CD59 binds to C8 and C9 in the assembling MAC and prevents membrane insertion.

Host cells are protected from their own complement by membrane-bound complement regulatory proteins like DAF, MCP and CD59. When an organ is transplanted into another species, natural antibodies in the recipient bind the endothelium of the donor organ and activate complement, thereby initiating rapid rejection. It has previously been suggested that, in contrast to human cells, those of the pig are very susceptible to human complement, and it was thought that this was because pig cell-surface complement regulatory proteins are ineffective against human complement. When an organ is transplanted into another species, natural antibodies in the recipient bind the endothelium of the donor organ and activate complement, thereby initiating rapid rejection. Several strategies have been shown to prevent or delay rejection, including removal of IgM natural antibodies and systemic decomplementation or inhibition of complement using sCR1, heparin or C1 inhibitor.

An alternative approach to the problem of rejection is to express human, membrane-bound, complement-regulatory molecules in transgenic pigs. Transgenic pigs expressing decay acceleration factor DAF (CD55), membrane co-factor protein MCP (CD46) and membrane inhibitor of reactive lysis, MIRL (CD59) have been generated. (see Klymium et al. Mol Reprod Dev (2010) 77:209-221). These human inhibitors have been shown to be abundantly expressed on porcine vascular endothelium. Ex vivo perfusion of hearts from control animals with human blood caused complement-mediated destruction of the organ within minutes, whereas hearts obtained from transgenic animals were refractory to complement and survived for hours.

The rationale for expressing human complement regulatory proteins in pig organs to "humanize" them as outlined above is based on the assumption that endogenous pig regulatory proteins are inefficient at inhibiting human complement and thus will contribute little to organ survival in the context of xenotransplantation. (Cantarovich et al., Xenotransplantation 9:25, 2002; Kirchhof et al., Xenotransplantation 11(5), 396, 2004; Tjernberg, et al., Transplantation. 2008 Apr. 27; 85(8): 1193-9). In addition, soluble complement inhibitors can prevent complement-mediated lysis of islets in vitro (Bennet, et al., Transplantation 69(5): 711, 2000).

U.S. Pat. No. 7,462,466 to Morgan et al. describes the isolation and characterization of porcine analogues of several of the human complement regulatory proteins (CRP). The studies illustrated that pig organs expressing human complement regulatory protein molecules were resistant to complement damage not because they expressed human CRP molecules, but because they expressed greatly increased amounts of functional CRP molecules. Morgan et al. found that increased expression of porcine CRP could be equally effective in protecting the donor organ from complement damage leading to hyperacute rejection as donor organs expressing human complement regulatory proteins.

CD46 has been characterized as a protein with regulatory properties able to protect the host cell against complement mediated attacks activated via both classical and alternative pathways (Barilla-LaBarca, M. L. et al., J. Immunol. 168, 6298-6304 (2002)). Human CD46 (hCD46) may offer protection against complement lysis during inflammation and humoral rejection mediated by low levels of natural or induced anti-Gal or anti-nonGal antibodies. As a result, more islets are able to engraft and be subsequently better protected against rejection, thus reducing immunosuppression needs.

In one embodiment of the present invention, animals (and organs, tissues and cells derived therefrom) are provided that lack expression of functional alpha Gal (or have reduced expression of alpha Gal) and have been genetically modified to incorporate and express at least one, at least two, at least three, or at least four or more compliment inhibitors. Expression of the compliment inhibitor may be ubiquitous or under the control of a tissue-specific promoter.

In exemplary embodiments, the compliment inhibitor is a membrane compliment inhibitor. The membrane complement inhibitor may be either an inhibitor of the complement activation pathway (inhibit C3 convertase formation) or an inhibitor of the terminal complement pathway (inhibit MAC formation). Membrane inhibitors of complement activation include complement receptor 1 (CR1), decay-accelerating factor (DAF or CD55), membrane cofactor protein (MCP or CD46) and the like. Membrane inhibitors of the terminal complement pathway may include CD59 and the like.

In exemplary embodiments, the present invention provides a transgenic animal (e.g., ungulate, porcine animal) comprising genetic modifications that result in (i) lack of expression of alpha Gal and (ii) incorporation and expression of at least four transgenes at a single locus under the control of at least two promoters, wherein at least one of the at least two transgenes is a compliment regulator and more specifically, a compliment inhibitor and even more specifically, a membrane compliment inhibitor. The single locus may be selected from a native locus, a modified native locus or a transgenic locus. In exemplary embodiments, the at least four transgenes are provided as a MCV and integration may be random integration or is facilitated by a genetic targeting tool. Optionally, the transgenic animal includes one or more additional genetic modifications, including but not limited to, modification of native porcine vWF, B4GalNT2, CMAH, or Forsmann genes.

In an exemplary embodiment, animals (and organs, tissues and cells derived therefrom) are provided comprising at least four transgenes, wherein the four transgenes are incorporated and expressed at a single locus under the control of at least two promoters, and wherein the pig lacks expression of alpha 1, 3 galactosyltransferase, wherein the at least four transgenes include at least one compliment regulator, and more specifically, at least one compliment inhibitor. The additional transgenes may be, for example, an immunosuppressant, cytoprotective gene or combinations thereof. The single locus may be selected from a native locus, a modified native locus or a transgenic locus. In exemplary embodiments, the at least four transgenes are provided as a MCV and integration is random or is facilitated by a genetic targeting tool. Optionally, the transgenic animal includes one or more additional genetic modifications.

In an exemplary embodiment, animals (and organs, tissues and cells derived therefrom) are provided that lack expression of functional alpha Gal (or expression is reduced) and have been genetically modified to incorporate and express at least four additional transgenes, wherein at least one of the at least two of the at least four additional transgenes are compliment inhibitors, and more particularly, at least two membrane compliment inhibitors.

In an exemplary embodiment, animals (and organs, tissues and cells derived therefrom) are provided that lack expression of functional alpha Gal (or expression is reduced) and have been genetically modified to (i) incorporate and express at least two compliment inhibitors, and more particularly, at least two membrane compliment inhibitors, and (ii) incorporate and express at least two additional transgenes selected from an anticoagulant, an immunosuppressant, cytoprotective gene or combinations thereof.

In one embodiment, animals (and organs, tissues and cells derived therefrom) are provided that lack expression of functional alpha Gal (or expression is reduced) and have been genetically modified to (i) incorporate and express CD46 and CD55 and (i) incorporate and express at least two additional transgenes. In a certain embodiment, the additional transgenes are selected from an anticoagulant, an immunosuppressant, cytoprotective gene or combination thereof.

In a particular embodiment, the animals (and organs, tissues and cells derived therefrom) are provided that lack expression of functional alpha Gal (or expression is reduced) and have been genetically modified to incorporate and express at least four transgenes under the control of at least two promoters, wherein at least one of the transgenes is CD46 and expression is controlled by a endogenous promoter.

In another embodiment, animals (and organs, tissues and cells derived therefrom are provided that lack expression of functional alpha Gal (or wherein expression is reduced) and have been genetically modified to (i) incorporate and express CD46 and CD55 and (i) incorporate and express at least three additional transgenes. In a certain embodiment, the additional transgenes are selected from an anticoagulant, an immunosuppressant cytoprotective gene or combination thereof. In an exemplary embodiment, the at least three additional transgenes include at least two anticoagulants. In an exemplary embodiment, the at least three additional transgenes include at least two anticoagulants and immunosuppressant.

In another embodiment, animals (and organs, tissues and cells derived therefrom) are provided that lack expression of functional alpha Gal (or expression is reduced) and have been genetically modified to (i) incorporate and express CD46 and CD55 and (i) incorporate and express at least four additional transgenes. In a certain embodiment, the additional transgenes are selected from an anticoagulant, an immunosuppressant, cytoprotective gene or combination thereof. In an exemplary embodiment, the at least four additional transgenes include at least two anticoagulants. In an exemplary embodiment, the at least four additional transgenes include at least two anticoagulants and an immunosuppressant. In an exemplary embodiment, the at least four additional transgenes include at least three anticoagulants.

In another embodiment, animals (and organs, tissues and cells derived therefrom) are provided that lack expression of functional alpha Gal (or expression is reduced) and have been genetically modified to (i) incorporate and express CD46 and CD55 and (i) incorporate and express at least five additional transgenes. In a certain embodiment, the additional transgenes are selected from an anticoagulant, an immunosuppressant, a cytoprotective gene or combination thereof. In an exemplary embodiment, the at least five additional transgenes include at least two anticoagulants and at least one immunosuppressant. In an exemplary embodiment, the at least five additional transgenes include at least three anticoagulants and at least one immunosuppressant. In an exemplary embodiment, the at least five additional transgenes include at least two anticoagulants and at least two immunosuppressants. In one embodiment, the animals can be modified to express a complement regulator peptide, a biologically active fragment or derivative thereof. In one embodiment, the complement regulator peptide is the full length complement regulator. In a further embodiment, the complement regulator peptide can contain less than the full length complement regulator protein.

Any human or porcine complement regulator sequences or biologically active portion or fragment thereof known to one skilled in the art can be according to the compositions and methods of the present invention. In additional embodiments, any consensus complement regulator peptide can be used according to the present invention. In another embodiment, nucleic acid and/or peptide sequences at least 80%, 85%, 90% or 95% homologous to the complement regulator peptides and nucleotide sequences described herein. In further embodiments, any fragment or homologous sequence that exhibits similar activity as complement regulator can be used.

Optionally, the animal expressing at least one compliment regulator (e.g., compliment inhibitor) among the at least four transgenes and lacking expression of alpha 1, 3 gal has at least one additional genetic modification.

B. Immunosuppressants

In one embodiment, the present invention provides a transgenic animal suitable for use as a source of organs, tissues and cells for xenotransplantation, wherein the donor animal has been genetically modified to incorporate and express at least one immunosuppressant. The transgenic animal typically has one or more additional genetic modifications, and more particularly, five or more additional genetic modifications and even more particularly, six or more additional genetic modifications.

An "immunosuppressant" transgene is capable of downregulating an immune response. For any type of transplantation procedure, a balance between efficacy and toxicity is a key factor for its clinical acceptance. With respect to islet transplantation, a further concern is that many of the current immunosuppressive agents in particular glucocortecoids or a calcineurin inhibitor, such as Tarcolimus, damage beta cells or induce peripheral insulin resistance (Zeng et al. Surgery (1993) 113: 98-102). A steroid-free immunosuppressive protocol ("Edmonton protocol") that includes sirolimus, low dose Tarcolimus, and a monoclonal antibody (mAb) against IL-2 receptor has been used in a trial of islet transplantation alone for patients with type-1 diabetes (Shapiro, A. M. J. et al, (2000), N. Eng. J. Med., 343: 230-238). The recent success using the "Edmonton protocol" has renewed enthusiasm for the use of islet transplantation to treat diabetes. However, concerns regarding toxicity of the Tacrolimus may limit the application of this therapy in humans.

Biological agents that block key T cell costimulatory signals, in particular the CD28 pathway, are potential alternatives to protect islets. Examples of agents that block the CD28 pathway include but are not limited to soluble CTLA4 including mutant CTLA4 molecules.

T-cell activation is involved in the pathogenesis of transplant rejection. Activation of T-cells requires at least two sets of signaling events. The first is initiated by the specific recognition through the T-cell receptor of an antigenic peptide combined with major histocampatibility complex (MHC) molecules on antigen presenting cells (APC5). The second set of signals is antigen nonspecific and is delivered by T-cell costimulatory receptors interacting with their ligands on APCs. In the absence of costimulation, T-cell activation is impaired or aborted, which may result in an antigen specific unresponsive state of clonal anergy, or in deletion by apoptotic death. Hence, the blockade of T-cell costimulation may provide an approach for suppressing unwanted immune responses in an antigen specific manner while preserving normal immune functions. (Dumont, F. J. 2004 Therapy 1, 289-304).

Of several T cell costimulatory pathways identified to date, the most prominent is the CD28 pathway. CD28, a cell surface molecule expressed on T-cells, and its counter receptors, the B7.1 (CD8O) and B7.2 (CD86) molecules, present on dendritic cells, macrophages, and B-cells, have been characterized and identified as attractive targets for interrupting T-cell costimulatory signals. A second T-cell surface molecule homologous to CD28 is known as cytoxic T-lymphocyte associated protein (CTLA4). CTLA4 is a cell surface signaling molecule, but contrary to the actions of CD28, CTLA4 negatively regulates T cell function. CTLA4 has 20-fold higher affinity for the B7 ligands than CD28. The gene for human CTLA4 was cloned in 1988 and chromosomally mapped in 1990 (Dariavach et al., Eur. J. Immunol. 18:1901-1905 (1988); Lafage-Pochitaloff et al., Immunogenetics 31:198-201 (1990); U.S. Pat. No. 5,977,318).

The CD28/B7 pathway has become an attractive target for interrupting T cell costimulatory signals. The design of a CD28/B7 inhibitor has exploited the endogenous negative regulator of this system, CTLA4. A CTLA4-immunoglobulin (CTLA4-Ig) fusion protein has been studied extensively as a means to inhibit T cell costimulation. A difficult balance must be reached with any immunosuppressive therapy; one must provide enough suppression to overcome the disease or rejection, but excessive immunosuppression will inhibit the entire immune system. The immunosuppressive activity of CTLA4-Ig has been demonstrated in preclinical studies of animal models of organ transplantation and autoimmune disease. Soluble CTLA4 has recently been tested in human patients with kidney failure, psoriasis and rheumatoid arthritis and has been formulated as a drug developed by Bristol-Myers Squibb (Abatacept, soluble CTLA4-Ig) that has been approved for the treatment of rheumatoid arthritis. This drug is the first in the new class of selective T cell costimulation modulators. Bristol-Myers Squibb is also conducting Phase II clinical trials with Belatacept (LEA29Y) for allograft kidney transplants. LEA29Y is a mutated form of CTLA4, which has been engineered to have a higher affinity for the B7 receptors than wild-type CTLA4, fused to immunoglobulin. Repligen Corporation is also conducting clinical trials with its CTLA4-Ig for idiopathic thrombocytopenic purpura. U.S. Pat. No. 5,730,403 entitled "Methods for protecting allogeneic islet transplant using soluble CTLA4 mutant molecules", describes the use of soluble CTLA4-Ig and CTLA4 mutant molecules to protect allogeneic islet transplants.

Although CTLA-4 from one organism is able to bind to B7 from another organism, the highest avidity is found for allogeneic B7. Thus, while soluble CTLA-4 from the donor organism can thus bind to both recipient B7 (on normal cells) and donor B7 (on xenotransplanted cells), it preferentially binds B7 on the xenograft. Thus in the embodiments of the invention comprising porcine animals or cells for xenotransplantation, porcine CTLA4 is typical. PCT Publication No. WO 99/5 7266 by Imperial College describes a porcine CTLA4 sequence and the administration of soluble CTLA4-Ig for xenotransplantation therapy. Vaughn A. et al., J Immunol (2000) 3175-3181, describes binding and function of soluble porcine CTLA4-Ig. Porcine CTLA4-Ig binds porcine (but not human) B7, blocking CD28 on recipient T cells and rendering these local T cells anergic without causing global T cell immunosuppression (see Mirenda et. al., Diabetes 54:1048-1055, 2005).

Much of the research on CTLA4-Ig as an immunosuppressive agent has focused on administering soluble forms of CTLA4-Ig to the patient. Transgenic mice engineered to express CTLA4-Ig have been created and subject to several lines of experimentation. Ronchese et al. examined immune system function generally after expression of CTLA4 in mice (Ronchese et al. J Exp Med (1994) 179: 809; Lane et al. J Exp Med. (1994) Mar. 1; 179(3):819). Sutherland et al. (Transplantation. 2000 69(9): 1806-12) described the protective effect of CTLA4-Ig secreted by transgenic fetal pancreas allografts in mice to test the effects of transgenically expressed CTLA4-Ig on allogenic islet transplantation. Lui et al. (J Immunol Methods 2003 277: 171-183) reported the production of transgenic mice that expressed CTLA4-Ig under control of a mammary specific promoter to induce expression of soluble CTLA4-Ig in the milk of transgenic animals for use as a bioreactor.

PCT Publication No. WO 01/30966 by Alexion Phamaceuticals Inc. describes chimeric DNA constructs containing the T cell inhibitor CTLA-4 attached to the complement protein CD59, as well as transgenic porcine cells, tissues, and organs containing the same. PCT Publication No. WO2007035213 (Revivicor) describes transgenic porcine animals that have been genetically modified to express CTLA4-Ig.

Additional immunosuppressors can be expressed in the animals, tissues or cells. For example, genes which have been inactivated in mice to produce an immuno compromised phenotype, can be cloned and disrupted by gene targeting in pigs. Some genes which have been targeted in mice and may be targeted to produce immuno compromised pigs include beta 2-microglobulin (MHC class I deficiency, Koller et al., Science, 248:1227-1230), TCR alpha, TCR beta (Mombaerts et al., Nature, 360:225-231), RAG-1 and RAG-2 (Mombaerts et al., (1992) Cell 68, 869-877, Shinkai, et al., (1992) Cell 68, 855-867, U.S. Pat. No. 5,859,307).

In one embodiment, the donor animals is modified to transgenically express a cytoxic T-lymphocyte associated protein 4-immunoglobin (CTLA4). The animals or cells can be modified to express CTLA4 peptide or a biologically active fragment (e.g., extracellular domain, truncated form of the peptide in which at least the transmembrane domain has been removed) or derivative thereof. The peptide may be, e.g., human or porcine. The CTLA4 peptide can be mutated. Mutated peptides may have higher affinity than wildtype for porcine and/or human B7 molecules. In one specific embodiment, the mutated CTLA4 can be CTLA4 (Glu104, Tyr29). The CTLA4 peptide can be modified such that it is expressed intracellularly. Other modifications of the CTLA4 peptide include addition of a endoplasmic reticulum retention signal to the N or C terminus The endoplasmic reticiulum retention signal may be, e.g., the sequence KDEL. The CTLA4 peptide can be fused to a peptide dimerization domain or an immunoglobulin (Ig) molecule. The CTLA4 fusion peptides can include a linker sequence that can join the two peptides. In another embodiment, animals lacking expression of functional immunoglobulin, produced according to the present invention, can be administered a CTLA4 peptide or a variant thereof (pCTLA4-Ig, or hCTLA4-Ig (Abatacept/Orencia, or Belatacept) as a drug to suppress their T-cell response. As used herein, CTLA4 is used to refer to any of these variants or those known in the art, e.g., CTLA4-Ig.

In one embodiment, the CTLA4 peptide is the full length CTLA4. In a further embodiment, the CTLA4 peptide can contain less than the full length CTLA4 protein. In one embodiment, the CTLA4 peptide can contain the extracellular domain of a CTLA-4 peptide. In a particular embodiment, the CTLA4 peptide is the extracellular domain of CTLA4. In still further embodiments, the present invention provides mutated forms of CTLA4. In one embodiment, the mutated form of CTLA4 can have higher affinity than wild type for porcine and/or human B7. In one specific embodiment, the mutated CTLA4 can be human CTLA4 (Glu104, Tyr29).

In one embodiment, the CTLA4 can be a truncated form of CTLA4, in which at least the transmembrane domain of the protein has been removed. In another embodiment, the CTLA4 peptide can be modified such that it is expressed intracellularly. In one embodiment, a Golgi retention signal can be added to the N or C terminus of the CTLA4 peptide. In one embodiment, the Golgi retention signal can be the sequence KDEL, which can be added to the C or N terminal of the CTLA4 peptide. In further embodiments, the CTLA4 peptide can be fused to a peptide dimerization domain. In one embodiment, the CTLA4 peptide can be fused to an immunoglobulin (Ig). In another embodiment, the CTLA4 fusion peptides can include a linker sequence that can join the two peptides.

Any human CTLA4 sequences or biologically active portion or fragment thereof known to one skilled in the art can be according to the compositions and methods of the present invention. Non-limiting examples include, but are not limited to the following Genbank accession numbers that describe human CTLA4 sequences: NM005214.2; BC074893.2; BC074842.2; AF414120.1; AF414120; AY402333; AY209009.1; BC070162.1; BC069566.1; L15006.1; AF486806.1; AC010138.6; AJ535718.1; AF225900.1; AF225900; AF411058.1; M37243.1; U90273.1; and/or AF316875.1. Further nucleotide sequences encoding CTLA4 peptides can be selected from those including, but not limited to the following Genbank accession numbers from the EST database: CD639535.1; A1733018.1; BM997840.1; BG536887.1; BG236211.1; BG058720.1; A1860i99.1; AW207094.1; AA210929.1; A1791416.1; BX113243.1; AW515943.1; BE837454.1; AA210902.1; BF329809.1; A1819438.1; BE837501.1; BE837537.1; and/or AA873138.1.

In additional embodiments, any consensus CTLA4 peptide can be used according to the present invention. In another embodiment, nucleic acid and/or peptide sequences at least 80%, 85%, 90% or 95% homologous to the native CTLA4 peptides and nucleotide sequences. In further embodiments, any fragment or homologous sequence that exhibits similar activity as CTLA4 can be used.

In other embodiments, the amino acid sequence which exhibits T cell inhibitory activity can be amino acids 38 to 162 of the porcine CTLA4 sequence or amino acids 38 to 161 of the human CTLA4 sequence (see, for example, PCT Publication No. WO 01/30966). In one embodiment, the portion used should have at least about 25% and preferably at least about 50% of the activity of the parent molecule.

In other embodiments, the CTLA4 nucleic acids and peptides of the present invention can be fused to immunoglobulin genes and molecules or fragments or regions thereof. Reference to the CTLA4 sequences of the present invention include those sequences fused to immunoglobulins. In one embodiment, the Ig can be a human Ig. In another embodiment, the Ig can be IgG, in particular, IgG1. In another embodiment, the Ig can be the constant region of IgG. In a particular embodiment, the constant region can be the C.gamma.1 chain of IgG. In one particular embodiment of the present invention, the extracelluar domain of porcine CTLA4 can be fused to human C.gamma.1 Ig. In another particular embodiment, the extracellular domain of human CTLA4 can be fused to IgG1 or IgG4. In a further particular embodiment, the extracellular domain of mutated CTLA4 (Glu 104, Tyr 29) can be fused to IgG.

In one embodiment, at least one of the transgenes is B7-H4, also known as B7x. B7-4H was identified in 2003, and belongs to the B7 family of immunoglobulins. See Sica, GL Immunity, Vol. 18, 849-861, June, 2003

In one embodiment, the donor animals is modified to transgenically express class II transactivators (CIITA) and mutants thereof PDL1, PDL2, tumor necrosis factor-.alpha.-related apoptosis-inducing ligand (TRAIL), Fas ligand (FasL, CD95L) integrin-associated protein (CD47), HLA-E, HLA-DP, HLA-DQ, or HLA-DR.

The class II transactivator (CIITA) is a bi- or multifunctional domain protein that acts as a transcriptional activator and plays a critical role in the expression of MHC class II genes. It has been previously demonstrated that a mutated form of the human CIITA gene, coding for a protein lacking the amino terminal 151 amino acids, acts as a potent dominant-negative suppressor of HLA class II expression (Yun et al., Int Immunol. 1997 October; 9(10): 1545-53). Porcine MHC class II antigens are potent stimulators of direct T-cell recognition by human CD4+ T cells and are, therefore, likely to play an important role in the rejection responses to transgenic pig donors in clinical xenotransplantation. It was reported that one mutated human CIITA construct was effective in pig cells, markedly suppressing IFN[gamma]-induced as well as constitutive porcine MHC class II expression. Moreover, stably transfected porcine vascular endothelial cell lines carrying mutated human CIITA constructs failed to stimulate direct T-cell xenorecognition by purified human CD4+ T cells (Yun et al., Transplantation. 2000 Mar. 15; 69(5):940-4). Organs, tissues and cells from CIITA-DN transgenic animals could induce a much reduced T-cell rejection responses in human recipients. In combination with other transgenes, transgenic expression of a mutated CIITA might enable long-term xenograft survival with clinically acceptable levels of immunosuppression.

In one embodiment, the present invention provides a transgenic animal (e.g., a pig) comprising genetic modifications that result in (i) lack of expression of alpha Gal and (ii) incorporation and expression of at least two transgenes at a single locus, wherein the at least four transgenes include at least one immunosuppressant. The single locus may be selected from a native locus, a modified native locus or a transgenic locus. Optionally, the transgenic animal includes one or more additional genetic modifications.

In exemplary embodiments, the present invention provides a transgenic animal (e.g., ungulate, porcine animal) comprising genetic modifications that result in (i) lack of expression of alpha Gal and (ii) incorporation and expression of at least four transgenes at a single locus, wherein at least two of the at least two transgenes are immunosuppressants. The single locus may be selected from a native locus, a modified native locus or a transgenic locus. The at least four transgenes may be provided as an MCV and incorporated into the locus utilizing a gene editing tool. Optionally, the transgenic animal includes one or more additional genetic modifications In an exemplary embodiment, animals (and organs, tissues and cells derived therefrom) are provided that lack expression of functional alpha GTalpha Gal (or expression is reduced) and have been genetically modified to (i) incorporate and express at least four transgenes at a single locus, wherein the at least four transgenes include at least one immunosuppressant. The immunosuppressant may be, for example, CIITA-DN or CLTA4-IG. The at least four transgenes may include additional transgenes selected from a compliment inhibitor, an anticoagulant or combinations thereof. The single locus may be selected from a native locus, a modified native locus or a transgenic locus. The at least three transgenes may be provided as an MCV and incorporated into the locus utilizing a gene editing tool. Optionally, the transgenic animal includes one or more additional genetic modifications In an exemplary embodiment, animals (and organs, tissues and cells derived therefrom) are provided that lack expression of functional alpha GTalpha Gal (or expression is reduced) and have been genetically modified to (i) incorporate and express at least four transgenes at a single locus, wherein the at least four transgenes include at least two immunosuppressants. The immunosuppressant may be, for example, CIITA-DN or CLTA4-IG. The at least four transgenes may also include a compliment inhibitor, an anticoagulant, or combinations thereof. The single locus may be selected from a native locus, a modified native locus or a transgenic locus. The at least three transgenes may be provided as an MCV and incorporated into the locus utilizing a gene editing tool. Optionally, the transgenic animal includes one or more additional genetic modifications C. Other Immunomodulators PDL1, PDL2: Typical costimulatory molecules for T-cell activation are CD80/86 or CD40. In addition to these positive costimulatory pathways over the past several years, new costimulatory pathways that mediate negative signals and are important for the regulation of T-cell activation have been found. One of these newer pathways is the pathway consisting of Programmed death 1 (PD-1) receptor and its ligands, PD-L1 and PD-L2. The PD-1 receptor is not expressed in resting cells but is upregulated after T and B cell activation. PD-1 contains a cytoplasmic immunoreceptor tyrosine-based switch motif and binding of PD-L1 or PD-L2 to PD-1 leads to inhibitory signals in T cells. Recent data suggest that PD1/PDLigand pathways may play a role in the control of T-cell subsets exhibiting regulatory activity. In mice, PD-1 signals have been shown to be required for the suppressive activity of regulatory T cells (Treg) and the generation of adaptive Treg. These observations suggest that PD-1/PDLig and interactions do not only inhibit T-cell responses but may also provoke immunoregulation. Several lines of evidence demonstrate that PD-1/PDLigand pathways can control engraftment and rejection of allografts implying that these molecules are interesting targets for immunomodulation after organ transplantation. Indeed, prolongation of allograft survival could be obtained by PDL1Ig gene transfer to donor hearts in a rat transplantation model. Moreover, enhancing PD-1 signaling by injection of PD-L1Ig has also been reported to protect grafts from rejection in mice. Recent data also show that overexpression of PD-L1IG on islet grafts in mice can partially prolong islet graft survival. Transgenic expression of human PD-L1 or PD-L2 in pig cells and tissues should reduce early human anti-pig T-cell responses initiated via the direct route of sensitization (Plege et al., Transplantation. 2009 Apr. 15; 87(7):975-82). By the induction of Treg it might also be possible to control T cells sensitized to the xenograft through the indirect route that is required to achieve long-lasting tolerance.

In a particular embodiment, the transgenic animal lacking expression of alpha Gal and incorporating and expressing at least four transgenes under the control of at least two promoters comprises incorporation and expression of PDL1 or PDL2.

TRAIL/Fas L: Expression of apoptosis inducing ligands, such as Fas ligand (FasL, CD95L) or tumor necrosis factor-.alpha.-related apoptosis-inducing ligand (TRAIL, Apo-2L) may eliminate T cells attacking a xenograft. TRAIL is a type II membrane protein with an extracellular domain homologous to that of other tumor necrosis factor family members showing the highest amino acid identity to FasL (28%). TRAIL exerts its apoptosis-inducing action preferentially on tumor cells. In normal cells, binding of TRAIL receptors does not lead to cell death. Recent studies have shown that the cytotoxic effects of immune cells, including T cells, natural killer cells, macrophages, and dendritic cells, are mediated at least partly by TRAIL. Expression of human TRAIL in transgenic pigs may provide a reasonable strategy for protecting pig tissues against cell-mediated rejection after xenotransplantation to primates. Stable expression of human TRAIL has been achieved in transgenic pigs and TRAIL expressed has been shown to be biologically functional in vitro (Klose et al., Transplantation. 2005 Jul. 27; 80(2):222-30). (d) CD47: CD47, known as integrin-associated protein, is a ubiquitously expressed 50-kDa cell surface glycoprotein that serves as a ligand for signal regulatory protein (SIRP).alpha. (also known as CD172a, SHPS-1), an immune inhibitory receptor on macrophages. CD47 and SIRP.alpha. constitute a cell-cell communication system (the CD47-SIRP.alpha. system) that plays important roles in a variety of cellular processes including cell migration, adhesion of B cells, and T cell activation. In addition, the CD47-SIRP.alpha. system is implicated in negative regulation of phagocytosis by macrophages. CD47 on the surface of several cell types (i.e., erythrocytes, platelets, or leukocytes) can protect against phagocytosis by macrophages by binding to the inhibitory macrophage receptor SIRP.alpha. The role of CD47-SIRP.alpha interactions in the recognition of self and inhibition of phagocytosis has been illustrated by the observation that primary, wild-type mouse macrophages rapidly phagocytose unopsonized RBCs obtained from CD47-deficient mice but not those from wild-type mice. It has also been reported that through its SIRP.alpha receptors, CD47 inhibits both Fc.gamma. and complement receptor-mediated phagocytosis. It has been demonstrated that porcine CD47 does not induce SIRP.alpha. tyrosine phosphorylation in human macrophage-like cell line, and soluble human CD47-Fc fusion protein inhibits the phagocytic activity of human macrophages toward porcine cells. It was also indicated that manipulation of porcine cells for expression of human CD47 radically reduces the susceptibility of the cells to phagocytosis by human macrophages (Ide et al., Proc Natl Acad Sci USA. 2007 Mar. 20; 104(12):5062-6). Expression of human CD47 on porcine cells could provide inhibitory signaling to SIRP.alpha. on human macrophages, providing an approach to preventing macrophage-mediated xenograft rejection.

In a particular embodiment, the transgenic animal lacking expression of alpha Gal and incorporating and expressing at least four transgenes under the control of at least two promoters comprises incorporation and expression of TRAIL or Fas L.

NK Cell Response. HLA-E/Beta 2 Microglobulin and HLA-DP, HLA-DQ, HLA-DR: Human natural killer (NK) cells represent a potential hurdle to successful pig-to-human xenotransplantation because they infiltrate pig organs perfused with human blood ex vivo and lyse porcine cells in vitro both directly and, in the presence of human serum, by antibody-dependent cell-mediated cytotoxicity. NK cell autoreactivity is prevented by the expression of major histocompatibility complex (MHC) class I ligands of inhibitory NK receptors on normal autologous cells. The inhibitory receptor CD94/NKG2A that is expressed on a majority of activated humanNK cells binds specifically to human leukocyte antigen (HLA)-E. The nonclassical human MHC molecule HLA-E is a potent inhibitory ligand for CD94/NKG2A-bearing NK cells and, unlike classical MHC molecules, does not induce allogeneic T-cell responses. HLA-E is assembled in the endoplasmic reticulum and transported to the cell surface as a stable trimeric complex consisting of the HLA-E heavy chain, .beta.2-microglobulin (.beta.2m), and a peptide derived from the leader sequence of some MHC class 1 molecules. The expression of HLA-E has been shown to provide partial protection against xenogeneic human NK cell cytotoxicity (Weiss et al., Transplantation. 2009 Jan. 15; 87(1):35-43). Transgenic expression of HLA-E on pig organs has the potential to substantially alleviate human NK cell-mediated rejection of porcine xenografts without the risk of allogeneic responses. In addition, transgenic pigs carrying other HLA genes have been successfully generated with the goal of "humanizing" porcine organs, tissues, and cells (Huang et al., Proteomics. 2006 November; 6(21):5815-25, see also U.S. Pat. No. 6,639, 122).

In a particular embodiment, the transgenic animal lacking expression of alpha Gal and incorporating and expressing at least four transgenes under the control of at least two promoters comprises incorporation and expression of HLA-3.

CD47: CD47 (Cluster of Differentiation 47) also known as integrin associated protein (IAP) is a transmembrane protein that in humans is encoded by the CD47 gene. CD47 is known to be both an immunosuppressant and immunomodulator and tolerogenic at of SIRPalpha signaling.

In an exemplary embodiment, animals (and organs, tissues and cells derived therefrom) are provided that lack expression of functional alpha GTalpha Gal (or expression is reduced) and have been genetically modified to (i) incorporate and express at least four transgenes at a single locus, wherein one of the at least four transgenes is CD47 The at least four transgenes may include additional transgenes selected from a compliment inhibitor, an anticoagulant or combinations thereof. The single locus may be selected from a native locus, a modified native locus or a transgenic locus. The at least three transgenes may be provided as an MCV and incorporated into the locus utilizing a gene editing tool. Optionally, the transgenic animal includes one or more additional genetic modifications In an exemplary embodiment, animals (and organs, tissues and cells derived therefrom) are provided that lack expression of functional alpha GTalpha Gal (or expression is reduced) and have been genetically modified to (i) incorporate and express at least four transgenes at a single locus, wherein one of the at least four transgenes is CD7. The at least four transgenes may include additional transgenes selected from a compliment inhibitor, an anticoagulant or combinations thereof. The single locus may be selected from a native locus, a modified native locus or a transgenic locus. The at least three transgenes may be provided as an MCV and incorporated into the locus utilizing a gene editing tool. Optionally, the transgenic animal includes one or more additional genetic modifications (ii) Anticoagulants In one embodiment, the present invention provides a transgenic donor animal suitable for use as a source of organs, tissues and cells for xenotransplantation, wherein the donor animal has been genetically modified to incorporate and express at least one anticoagulant. The animal typically has additional genetic modifications, are more particularly, at least five additional genetic modifications, and even more particularly, at least six additional genetic modifications. In exemplary embodiments, the present invention is a transgenic animal which comprises genetic modifications that result in (i) lack of expression of alpha Gal and (ii) incorporation and expression of at least four transgenes at a single locus under the control of at least two promoters, wherein at least one transgene is an anticoagulant.

The anticoagulant may be any suitable anticoagulant. Expression may be ubiquitous or tissue specific. In a particular embodiment, expression is controlled by a promoter active primarily in endothelium.

Representative, non-limiting examples of suitable anticoagulant transgenes include tissue factor pathway inhibitor, hirudin, thrombomodulin, Endothelial cell protein C receptor (EPCR), CD39 and combinations thereof.

Tissue factor pathway inhibitor (TFPI) is a single-chain polypeptide which can reversibly inhibit Factor Xa (Xa) and Thrombin (Factor IIa) and thus inhibits TF dependent coagulation. For a review of TFPI, please see Crawley and Lane (Arterioscler Thromb Vasc Biol. 2008, 28(2):233-42). Dorling and colleagues generated transgenic mice expressing a fusion protein consisting of the three Kunitz domains of human TFPI linked to the transmembrane/cytoplasmic domains of human CD4, with a P-selectin tail for targeting to Weibel-Palade intracellular storage granules (Chen D, et al. Am J Transplant 2004; 4: 1958-1963.). The resulting activation-dependent display of TFPI on the endothelium was sufficient to completely inhibit thrombosis-mediated acute humoral rejection of mouse cardiac xenografts by cyclosporine-treated rats. There was also a suggestion that effective regulation of coagulation may prevent chronic rejection. Similar results were obtained with transgenic mouse hearts expressing a hirudin/CD4/P-selectin fusion protein, indicating that inhibition of thrombin generation or activity was the key to protection in this model.

Hirudin is a naturally occurring peptide in the salivary glands of medicinal leeches (such as Hirudo medicinalis) and is a potent inhibitor of thrombin. Dorling and coworkers (Chen et al., J Transplant. 2004 December; 4(12):1958-63) also generated transgenic mice expressing membrane-tethered hirudin fusion proteins, and transplanted their hearts into rats (mouse-rat Xeno-Tx). In contrast to control non-transgenic mouse hearts, which were all rejected within 3 days, 100% of the organs from both strains of transgenic mice were completely resistant to humoral rejection and survived for more than 100 days when T-cell-mediated rejection was inhibited by administration of ciclosporin A. Riesbeck et al., (Circulation. 1998 Dec. 15; 98(24):2744-52) also explored the expression of hirudin fusion proteins in mammalian cells as a strategy for prevention of intravascular thrombosis. Expression in cells reduced local thrombin levels and inhibited fibrin formation. Therefore, hirudin is another anticoagulant transgene of interest for preventing the thrombotic effects present in xenotransplantation.

Thrombomodulin (TM) functions as a cofactor in the thrombin-induced activation of protein C in the anticoagulant pathway by forming a 1:1 stoichiometric complex with thrombin. Endothelial cell protein C receptor (EPCR) is an N-glycosylated type I membrane protein that enhances the activation of protein C. The role of these proteins in the protein C anticoagulant system is reviewed by Van de Wouwer et al., Arterioscler Thromb Vasc Biol. 2004 August; 24(8):1374-83. Expression of these and other anticoagulant transgenes has been explored by various groups to potentially address the coagulation barriers to xenotransplantation (reviewed by Cowan and D'Apice, Cur Opin Organ Transplant. 2008 April; 13(2): 178-83). Esmon and coworkers (Li et al., J Thromb Haemost. 2005 July; 3(7):1351-9 over-expressed EPCR on the endothelium of transgenic mice and showed that such expression protected the mice from thrombotic challenge. Iino et al., (J Thromb Haemost. 2004 May; 2(5):833-4), suggested ex-vivo over expression of TM in donor islets via gene therapy as a means to prevent thrombotic complications in islet transplantation.

CD39 is a major vascular nucleoside triphosphate diphosphohydrolase (NTPDase), and converts ATP, and ADP to AMP and ultimately adenosine. Extracellular adenosine plays an important role in thrombosis and inflammation, and thus has been studied for its beneficial role in transplantation (reviewed by Robson et al. Semin Thromb Hemost. 2005 April; 31(2):217-33). Recent studies have shown that CD39 has a major effect in reducing the inflammatory response (Beldi et al., Front Biosci, 2008, 13:2588-2603). Transgenic mice expressing hCD39 exhibited impaired platelet aggregation, prolonged bleeding times, and resistance to systemic thromboembolism in a heart transplant model (Dwyer et al., J Clin Invest. 2004 May; 113(10): 1440-6). They were also shown to express CD39 on pancreatic islets and when incubated with human blood, these islets significantly delayed clotting time compared to wild type islets (Dwyer et al., Transplantation. 2006 Aug. 15; 82(3):428-32). Preliminary efforts at expressing hCD39 at high levels from a constitutive promoter system in transgenic pigs, showed high post-natal lethality (Revivicor, Inc., unpublished data). However, endothelial cell specific expression of CD39 has shown to be better tolerated by transgenic pigs. Thus there is a need to express certain anticoagulant transgenes in pigs in a manner that does not compromise the animal's wellbeing, yet still provides adequate levels of expression for utility in clinical xenotransplantation.

In exemplary embodiments, the present invention provides a transgenic animal (e.g., ungulate, porcine animal) that has genetic modifications that result in (i) lack of expression of alpha Gal (or expression is reduced) and (ii) incorporation and expression of at least four transgenes at a single locus under the control of two promoters, wherein at least one of the at least two transgenes is an anticoagulant. In one embodiment, the anticoagulant is selected from tissue factor pathway inhibitor, hirudin, thrombomodulin, Endothelial cell protein C receptor (EPCR), CD39 and combinations thereof. The single locus may be a native locus, modified native locus or transgenic locus. The native locus could be GGTA1, B4GalNT2, CMAH, Rosa26, AAVS1, or other endogenous loci that might impart beneficial expression characteristics on the integrated transgenes. The at least four transgenes under control of at least two promoters may be provided as an MCV and incorporation may involve a gene editing tool. Such editing may involve targeted insertion into a predetermined site (eg. landing pad) that acts as either a "safe harbor" (so as not to interrupt any essential genes in the genome), and/or to provide desirable characteristics specific to the integration site. In the case of insertions at loci important to preventing xenograft rejection, insertion of the multi-transgenes also can have the outcome of inactivation of a porcine gene involved in inducing xeno reactions in primates (ie. inactivation of alpha Gal, CMAH, or B4GalNT2 or others (iGB3, Forssman). Optionally, the animal may include one or more additional genetic modifications, and at more than one locus, wherein the at least four transgenes are inserted at one locus, and another set of two or more transgenes (under control of at least two promoters) could be co-integrated at a second site. An alternative embodiment provides for MCV insertion at one locus, and targeted inactivation at a different locus, where such inactivation might be facilitated by a gene editing tool.

In exemplary embodiments, the present invention provides a transgenic animal (e.g., ungulate, porcine animal) that has genetic modifications that result in (i) lack of expression of alpha Gal (or expression is reduced) and (ii) incorporation and expression of at least four, at least five, at least six, at least seven, or at least eight or more transgenes at a single locus, wherein at least one, at least two or at least three of the transgenes is an anticoagulant.

In one embodiment, the anticoagulant is selected from tissue factor pathway inhibitor, hirudin, thrombomodulin, Endothelial cell protein C receptor, CD39 and combinations thereof. The at least four transgenes may be provided as an MCV and incorporation may involve a gene editing tool. The single locus may be a native locus, modified native locus or transgenic locus. Optionally, the animal may include one or more additional genetic modifications.

In one embodiment, the present invention provides a transgenic animal (e.g., ungulate, porcine animal) that lacks expression of alpha Gal (or expression is reduced) and has been genetically modified to incorporate and express at least three anticoagulants. In certain embodiments, the anticoagulant is selected from tissue factor pathway inhibitor (TFPI), hirudin, thrombomodulin, Endothelial cell protein C receptor, CD39 and combinations thereof. In certain embodiments, at least one of the at least three anticoagulants is controlled by expression of a promoter primarily active in endothelial cells. In certain embodiments, at least two of the at least three anticoagulants is controlled by expression of a promoter primarily active in endothelial cells.

In exemplary embodiments, the present invention provides a transgenic animal (e.g., ungulate, porcine animal) that lacks expression of alpha Gal (or expression is reduced) and has been genetically modified to incorporate and express at least three anticoagulants, wherein one of the at least three anticoagulant is EPCR.

In exemplary embodiments, the present invention provides a transgenic animal (e.g., ungulate, porcine animal) that lacks expression of alpha Gal (or expression is reduced) and has been genetically modified to incorporate and express at least three anticoagulants, wherein the at least three anticoagulants include EPCR and TBM.

In one embodiment, the present invention provides a transgenic animal (e.g., ungulate, porcine animal) that lacks expression of alpha Gal (or expression is reduced) and has been genetically modified to incorporate and express at least four additional transgenes, wherein the at least four additional transgenes include at least one anticoagulant. In certain embodiments, the at least one anticoagulant is selected from tissue factor pathway inhibitor, hirudin, thrombomodulin, Endothelial cell protein C receptor, CD39 and combinations thereof. In one embodiment, the at least one anticoagulant is EPCR.

In one embodiment, the present invention provides a transgenic animal (e.g., ungulate, porcine animal) that lacks expression of alpha Gal (or expression is reduced) and has been genetically modified to incorporate and express at least four additional transgenes, wherein the at least four additional transgenes include at least two anticoagulants. In certain embodiments, the at least two anticoagulants are selected from tissue factor pathway inhibitor, hirudin, thrombomodulin, Endothelial cell protein C receptor, CD39 and combinations thereof. In one embodiment, the at least two anticoagulants include EPCR and TBM. In another embodiment, the at least two anticoagulants include EPCR and TFPI.

In one embodiment, the present invention provides a transgenic animal (e.g., ungulate, porcine animal) that lacks expression of alpha Gal (or expression is reduced) and has been genetically modified to incorporate and express at least four additional transgenes, wherein the at least four additional transgenes include at least three anticoagulants. In certain embodiments, the at least three anticoagulants are selected from tissue factor pathway inhibitor, hirudin, thrombomodulin, Endothelial cell protein C receptor, CD39 and combinations thereof. In one embodiment, the at least three anticoagulants include EPCR, TBM and TFPI. In another embodiment, the at least three anticoagulants include EPCR, TBM and CD39.

In one embodiment, the present invention provides a transgenic animal (e.g., ungulate, porcine animal) that lacks expression of alpha Gal (or expression is reduced) and has been genetically modified to incorporate and express at least five additional transgenes, wherein the at least five additional transgenes include at least two anticoagulants. In certain embodiments, the at least two anticoagulants are selected from tissue factor pathway inhibitor, hirudin, thrombomodulin, Endothelial cell protein C receptor, CD39 and combinations thereof. In one embodiment, the at least two anticoagulants include EPCR and TBM. In another embodiment, the at least two anticoagulants include EPCR and TFPI.

In one embodiment, the present invention provides a transgenic animal (e.g., ungulate, porcine animal) that lacks expression of alpha Gal (or expression is reduced) and has been genetically modified to incorporate and express at least five additional transgenes, wherein the at least five additional transgenes include at least three anticoagulants. In certain embodiments, the at least three anticoagulants are selected from tissue factor pathway inhibitor, hirudin, thrombomodulin, Endothelial cell protein C receptor, CD39 and combinations thereof. In one embodiment, the at least three anticoagulants include EPCR, TBM and TFPI. In another embodiment, the at least three anticoagulants include EPCR, TBM and CD39.

In one embodiment, the present invention provides a transgenic animal (e.g., ungulate, porcine animal) that lacks expression of alpha Gal (or expression is reduced) and has been genetically modified to incorporate and express at least six additional transgenes, wherein the at least six additional transgenes include at least two anticoagulants. In certain embodiments, the at least two anticoagulants are selected from tissue factor pathway inhibitor, hirudin, thrombomodulin, Endothelial cell protein C receptor, CD39 and combinations thereof. In one embodiment, the at least two anticoagulants include EPCR and TBM. In another embodiment, the at least two anticoagulants include EPCR and TFPI. Optionally, the at least six additional transgenes also include at least one immunosuppressant.

In one embodiment, the present invention provides a transgenic animal (e.g., ungulate, porcine animal) that lacks expression of alpha Gal (or expression is reduced) and has been genetically modified to incorporate and express at least six additional transgenes, wherein the at least six additional transgenes include at least three anticoagulants. In certain embodiments, the at least three anticoagulants are selected from tissue factor pathway inhibitor, hirudin, thrombomodulin, Endothelial cell protein C receptor, CD39 and combinations thereof. In one embodiment, the at least three anticoagulants include EPCR, TBM and TFPI. In another embodiment, the at least three anticoagulants include EPCR, TBM and CD39.

(iii) Cytoprotective Transgenes

In one embodiment, the present invention provides a transgenic donor animal suitable for use as a source of organs, tissues and cells for xenotransplantation, wherein the donor animal has been genetically modified to incorporate and express at least one cryoprotective transgene ("cytoprotectants'). In exemplary embodiments, the present invention provides a transgenic animal (e.g., a pig) comprising genetic modifications that result in (i) lack of expression of alpha Gal; and (ii) incorporation and expression of at least four transgenes at a single locus under the control of at least two promoters, wherein at least one of the at least four transgenes is a cytoprotective transgene.

Cytoprotective transgenes are considered to include anti-apoptotics, anti-oxidants and anti-inflammatories. Examples include:

(a) A20: A20 provides anti-inflammatory and anti-apoptotic activity. Vascularized transplanted organs may be protected against endothelial cell activation and cellular damage by anti-inflammatory, anticoagulant and/or anti-apoptotic molecules. Among genes with great potential for modulation of acute vascular rejection (AVR) is the human A20 gene (hA20) that was first identified as a tumor necrosis factor (TNF)-.alpha.inducible factor in human umbilical vein endothelial cells. Human A20 has a double cytoprotective function by protecting endothelial cells from TNF-mediated apoptosis and inflammation, via blockade of several caspases, and the transcription factor nuclear factor-.kappa.B, respectively. Viable A20 transgenic piglets have been produced and in these animals expression of hA20 was restricted to skeletal muscle, heart and PAECs which were protected against TNF mediated apoptosis by hA20 expression and at least partly against CD95(Fas)L-mediated cell death. In addition, cardiomyocytes from hA20-transgenic-cloned pigs were partially protected against cardiac insults (Oropeza et al., Xenotransplantation. 2009 November; 16(6):522-34).

(b) HO-1: HO provides anti-inflammatory, anti-apoptotic, and anti-oxidant activity. Heme oxygenases (HOs), rate-limiting enzymes in heme catabolism, also named HSP32, belong to members of heat shock proteins, wherein the heme ring is cleaved into ferrous iron, carbon monoxide (CO) and biliverdin that is then converted to bilirubin by biliverdin reductase. Three isoforms of HOs, including HO-1, HO-2 and HO-3, have been cloned. The expression of HO-1 is highly inducible, whereas HO-2 and HO-3 are constitutively expressed (Maines M D et al., Annual Review of Pharmacology & Toxicology 1997; 37:517-554, and Choi A M et al., American Journal of Respiratory Cell & Molecular Biology 1996; 15:9-19). An analysis of HO-1−/−mice suggests that the gene encoding HO-1 regulates iron homeostasis and acts as a cytoprotective gene having potent antioxidant, anti-inflammatory and anti-apoptotic effects (Poss K D et al., Proceedings of the National Academy of Sciences of the United States of America 1997; 94:10925-10930, Poss K D et al., Proceedings of the National Academy of Sciences of the United States of America 1997; 94:10919-10924, and Soares M P et al., Nature Medicine 1998; 4:1073-1077). Similar findings were recently described in a case report of HO-1 deficiency in humans (Yachie A et al., Journal of Clinical Investigation 1999; 103:129-135). The molecular mechanisms responsible for the cytoprotective effects of HO-1, including anti-inflammation, anti-oxidation and anti-apoptosis, are mediated by its' reaction products. HO-1 expression can be modulated in vitro and in vivo by protoporphyrins with different metals. Cobalt protoporphyrins (CoPP) and iron protoporphyrins (FePP) can up-regulate the expression of HO-1. In contrast, tin protoporphyrins (SnPP) and zinc protoporphyrins (ZnPP) inhibit the activity of HO-1 at the protein level. Recently, it has been proved that the expression of HO-1 suppresses the rejection of mouse-to-rat cardiac transplants (Sato K et al., J. Immunol. 2001; 166:4185-4194), protects islet cells from apoptosis, and improves the in vivo function of islet cells after transplantation (Pileggi A et al., Diabetes 2001; 50: 1983-1991). It has also been proved that administration of HO-1 by gene transfer provides protection against hyperoxia-induced lung injury (Otterbein L E et al., J Clin Invest 1999; 103: 1047-1054), upregulation of HO-1 protects genetically fat Zucker rat livers from ischemia/reperfuiision injury (Amersi F et al., J Clin Invest 1999; 104: 1631-1639), and ablation or expression of HO-1 gene modulates cisplatin-induced renal tubular apoptosis (Shiraishi F et al., Am J Physiol Renal Physiol 2000; 278:F726-F736). In transgenic animal models, it was shown that over-expression of HO-1 prevents the pulmonary inflammatory and vascular responses to hypoxia (Minamino T et al., Proc. Natl. Acad. Sci. USA 2001; 98:8798-8803) and protects heart against ischemia and reperfusion injury (Yet S F, et al., Cir Res 2001; 89:168-173). Pigs carrying a HO-1 transgene have been produced however clinical effects related to their use in xenotransplantation were not reported (U.S. Pat. No. 7,378,569).

(c) FAT-1: FAT-1 provides anti-inflammatory activity. Polyunsaturated fatty acids (PUFAs) play a role in inhibiting (n-3 class) inflammation. Mammalian cells are devoid of desaturase that converts n-6 to n-3 PUFAs. Consequently, essential n-3 fatty acids must be supplied with the diet. Unlike mammals, however, the free-living nematode *Caenorhabditis elegans* expresses a n-3 fatty acid desaturase that introduces a double bond into n-6-fatty acids at the n-3 position of the hydrocarbon chains to form n-3 PUFAs. Transgenic mice have been generated that express the *C. elegans* fat-1 gene and, consequently, are able to efficiently convert dietary PUFAs of the 6 series to PUFAs of 3-series, such as EPA (20:5 n-3) and DHA (22-6 n-3). (Kang et al., Nature. 2004 Feb. 5; 427(6974):504). Another group produced a transgenic mouse model wherein the codons of fat-1 cDNA were further optimized for efficient translation in mammalian systems; endogenous production of n-3 PUFAs was achieved through overexpressing a *C. elegans* n-3 fatty acid desaturase gene, mfat-1. This group showed that cellular increase of n-3 PUFAs and reduction of n-6 PUFAs through transgenic expression of mfat-1 enhanced glucose-, amino acid-, and GLP-1-stimulated insulin secretion in isolated pancreatic islets of the mice, and rendered the islets strongly resistant to cytokine-induced cell death (Wei et al., Diabetes. 2010 February; 59(2):471-8).

(d) Soluble TNF-alpha receptor (sTNFR1): Tumor necrosis factor (TNF, cachexin or cachectin and formally known as tumor necrosis factor-alpha) is a cytokine involved in systemic inflammation and is a member of a group of cytokines that stimulate the acute phase reaction. The primary role of TNF is in the regulation of immune cells. TNF is able to induce apoptotic cell death, to induce inflammation. Soluble TNF-alpha receptor 1 (sTNFR1) is an extracellular domain of TNFR1 and an antagonist to TNF-alpha (Su et al., 1998. Arthritis Rheum. 41, 139-149). Transgenic expression of sTNFR1 in xenografts may have beneficial anti-inflammatory effects.

Other cytoprotectives with relevant anti-oxidant properties include, without limitation, SOD and Catalyse. Oxygen is the essential molecule for all aerobic organisms, and plays predominant role in ATP generation, namely, oxidative phosphorylation. During this process, reactive oxygen species (ROS) including superoxide anion (O(2)(−)) and hydrogen peroxide (H(2)O(2)) are produced as by-products. In man, an antioxidant defense system balances the generation of ROS. Superoxide dismutase (SOD) and catalase are two enzymes with anti-oxidant properties. SOD catalyses the dismutation of superoxide radicals to hydrogen peroxide, the latter being converted to water by catalase and glutathione peroxidase. Cellular damage resulting from generation of ROS can occur in a transplant setting. Because of reduced antioxidant defenses, pancreatic beta-cells are especially vulnerable to free radical and inflammatory damage. Commonly used antirejection drugs are excellent at inhibiting the adaptive immune response; however, most are harmful to islets and do not protect well from reactive oxygen species and inflammation resulting from islet isolation and ischemia-reperfusion injury. Therefore there is an interest in treating islets ex-vivo with anti-oxidants, or expressing anti-oxidant genes via gene therapy or transgenic expression in donor tissues. Ex vivo gene transfer of EC-SOD and catalase were anti-inflammatory in a rat model of antigen induced arthritis (Dai et al., Gene Ther. 2003 April; 10(7): 550-8). In addition, delivery of EC-SOD and/or catalase genes through the portal vein markedly attenuated hepatic I/R injury in a mouse model (He et al., Liver Transpl. 2006 December; 12(12): 1869-79). In a recent mouse study, pancreatic islets treated with catalytic antioxidant before syngeneic, suboptimal syngeneic, or xenogeneic transplant exhibited superior function compared with untreated controls. In this same study, diabetic murine recipients of catalytic antioxidant-treated allogeneic islets exhibited improved glycemic control post-transplant and demonstrated a delay in allograft rejection (Sklavos et al., Diabetes. 2010 July; 59(7): 1731-8. Epub 2010 Apr. 22). In another mouse study, islet grafts overexpressing MnSOD functioned approximately 50% longer than control grafts (Bertera et al., Diabetes. 2003 February; 52(2):387-93).

Moreover, certain anti-coagulants also provide anti-inflammatory activity including thrombomodulin, EPCR and CD39.

In exemplary embodiments, the present invention provides a transgenic animal (e.g., a pig) comprising genetic modifications that result in (i) lack of expression of alpha Gal; and (ii) incorporation and expression of at least four transgenes at a single locus (under control of at least two promoters), wherein at least one of the at least four transgenes is a cytoprotective transgene. The single locus may be a native locus, a modified native locus or a transgenic locus. The at least two transgenes may be provided as an MCV and incorporation may involve a gene editing tool. Optionally, the animal may have one or more additional genetic modifications.

In exemplary embodiments, the present invention provides a transgenic animal (e.g., a pig) comprising genetic modifications that result in (i) lack of expression of alpha Gal; and (ii) incorporation and expression of, at least five, at least six, at least seven, or at least eight transgenes at a single locus, or at least four transgenes at one locus and one or more transgenes at a second locus, wherein at least one of the transgenes is a cytoprotective transgene, and wherein the at least four transgenes are under control of at least two promoters, which could be different combinations of constitutive, ubiquitous, tissue-specific or inducible regulated promoter systems. The transgenes may be provided as an MCV and incorporation may involve a gene editing tool. The single locus may be a native locus, a modified native locus or a transgenic locus. Optionally, the animal may have one or more additional genetic modifications.

D. Production of Transgenic Animals

Transgenic animals can be produced by any method known to one of skill in the art including, but not limited to, selective breeding, nuclear transfer, introduction of DNA into oocytes, sperm, zygotes, or blastomeres, or via the use of embryonic stem cells. Genetic editing tools may also be utilized, as described further herein.

In some embodiments, genetic modifications may be identified in animals that are then bred together to form a herd of animals with a desired set of genetic modifications (or a single genetic modification). These progeny may be further bred to produce different or the same set of genetic modifications (or single genetic modification) in their progeny. This cycle of breeding for animals with desired genetic modification(s) may continue for as long as one desires. “Herd” in this context may comprise multiple generations of animals produced over time with the same or different genetic modification(s). “Herd” may also refer to a single generation of animals with the same or different genetic modification(s).

Cells useful for genetic modification (via, for example, but not limited to, homologous recombination, random insertion/integration, nuclease editing, zinc finger plus TALEN nucleases, CRISPR/Cas 9 nucleases) include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc. Moreover, the cells used for producing the genetically modified animal (via, for example, but not limited to, nuclear transfer) can be obtained from different organs, e.g., skin, lung, pancreas, liver, stomach, intestine, heart, reproductive organs, bladder, kidney, urethra and other urinary organs, etc. Cells can be obtained from any cell or organ of the body, including all somatic or germ cells.

Additionally, animal cells that can be genetically modified can be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In one embodiment of the invention, cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, blood cells, blood precursor cells, bone cells, bone precursor cells, neuronal stem cells, primordial stem cells, adult stem cells, mesenchymal stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B-cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts. In one alternative embodiment, embryonic stem cells can be used. An embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF).

Embryonic stem cells are a preferred germ cell type, an embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF).

Cells of particular interest include, among other lineages, stem cells, e.g. hematopoietic stem cells, embryonic stem cells, mesenchymal stem cells, etc., the islets of Langerhans, adrenal medulla cells which can secrete dopamine, osteoblasts, osteoclasts, epithelial cells, endothelial cells, leukocytes, e.g. B- and T-lymphocytes, myelomonocytic cells, etc., neurons, glial cells, ganglion cells, retinal cells, liver cells, e.g. hepatocytes, bone marrow cells, keratinocytes, hair follicle cells, and myoblast (muscle) cells.

In a particular embodiment, the cells can be fibroblasts or fibroblast-like cells having a morphology or a phenotype that is not distinguishable from fibroblasts, or a lifespan before senescense of at least 10 or at least 12 or at least 14 or at least 18 or at least 20 days, or a lifespan sufficient to allow homologous recombination and nuclear transfer of a non-senescent nucleus; in one specific embodiment, the cells can be fetal fibroblasts. Fibroblast cells are a suitable somatic cell type because they can be obtained from developing fetuses and adult animals in large quantities. These cells can be easily propagated in vitro with a rapid doubling time and can be clonally propagated for use in gene targeting procedures. The cells to be used can be from a fetal animal, or can be neonatal or from an adult animal in origin. The cells can be mature or immature and either differentiated or non-differentiated.

(i) Homologous Recombination

Homologous recombination permits site-specific modifications in endogenous genes and thus novel alterations can be engineered into the genome. A primary step in homologous recombination is DNA strand exchange, which involves a pairing of a DNA duplex with at least one DNA strand containing a complementary sequence to form an intermediate recombination structure containing heteroduplex DNA (see, for example Radding, C. M. (1982) Ann. Rev. Genet. 16: 405; U.S. Pat. No. 4,888,274). The heteroduplex DNA can take several forms, including a three DNA strand containing triplex form wherein a single complementary strand invades the DNA duplex (Hsieh et al. (1990) Genes and Development 4: 1951; Rao et al., (1991) PNAS 88:2984)) and, when two complementary DNA strands pair with a DNA duplex, a classical Holliday recombination joint or chi structure (Holliday, R. (1964) Genet. Res. 5: 282) can form, or a double-D loop ("Diagnostic Applications of Double-D Loop Formation" U.S. Ser. No. 07/755,462, filed Sep. 4, 1991). Once formed, a heteroduplex structure can be resolved by strand breakage and exchange, so that all or a portion of an invading DNA strand is spliced into a recipient DNA duplex, adding or replacing a segment of the recipient DNA duplex. Alternatively, a heteroduplex structure can result in gene conversion, wherein a sequence of an invading strand is transferred to a recipient DNA duplex by repair of mismatched bases using the invading strand as a template (Genes, 3rd Ed. (1987) Lewin, B., John Wiley, New York, N.Y.; Lopez et al. (1987) Nucleic Acids Res. 15: 5643). Whether by the mechanism of breakage and rejoining or by the mechanism(s) of gene conversion, formation of heteroduplex DNA at homologously paired joints can serve to transfer genetic sequence information from one DNA molecule to another.

The ability of homologous recombination (gene conversion and classical strand breakage/rejoining) to transfer genetic sequence information between DNA molecules renders targeted homologous recombination a powerful method in genetic engineering and gene manipulation.

In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome). The present invention can use homologous recombination to inactivate a gene or insert and upregulate or activate a gene in cells, such as the cells described above. The DNA can comprise at least a portion of the gene(s) at the particular locus with introduction of an alteration into at least one, optionally both copies, of the native gene(s), so as to prevent expression of functional gene product. The alteration can be an insertion, deletion, replacement, mutation or combination thereof. When the alteration is introduced into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable markers can be used. The resulting transformants are screened for the absence of a functional target antigen and the DNA of the cell can be further screened to ensure the absence of a wild-type target gene. Alternatively, homozygosity as to a phenotype can be achieved by breeding hosts heterozygous for the mutation.

A number of papers describe the use of homologous recombination in mammalian cells. Illustrative of these papers are Kucherlapati et al. (1984) Proc. Natl. Acad. Sci. USA 81:3153-3157; Kucherlapati et al. (1985) Mol. Cell. Bio. 5:714-720; Smithies et al. (1985) Nature 317:230-234; Wake et al. (1985) Mol. Cell. Bio. 8:2080-2089; Ayares et al. (1985) Genetics 111:375-388; Ayares et al. (1986) Mol. Cell. Bio. 7:1656-1662; Song et al. (1987) Proc. Natl. Acad. Sci. USA 84:6820-6824; Thomas et al. (1986) Cell 44:419-428; Thomas and Capecchi, (1987) Cell 51: 503-512; Nandi et al. (1988) Proc. Natl. Acad. Sci. USA 85:3845-3849; and Mansour et al. (1988) Nature 336:348-352; Evans and Kaufman, (1981) Nature 294:146-154; Doetschman et al. (1987) Nature 330:576-578; Thoma and Capecchi, (1987) Cell 51:503-512; Thompson et al. (1989) Cell 56:316-321.

In one embodiment, the at least four transgenes incorporated and expressed in the transgenic animal of the present invention are introduced by homologous recombination. In another embodiment, at least one of the four transgenes incorporated and expressed in the transgenic animal of the present invention are introduced by homologous recombination.

(ii) Random Insertion

In one embodiment, the DNA encoding the transgene sequences can be randomly inserted into the chromosome of a cell. The random integration can result from any method of introducing DNA into the cell known to one of skill in the art. This may include, but is not limited to, electroporation, sonoporation, use of a gene gun, lipotransfection, calcium phosphate transfection, use of dendrimers, microinjection, the use of viral vectors including adenoviral, AAV, and retroviral vectors, and group II ribozymes. In one embodiment, the DNA encoding the can be designed to include a reporter gene so that the presence of the transgene or its expression product can be detected via the activation of the reporter gene. Any reporter gene known in the art can be used, such as those disclosed above. The reporter gene could also be one of the transgenes that is being added to the cell, such that cell surface expression of that transgene (eg. DAF or CD46 or EPCR or CD47) could be used in conjunction with flow cytometry (and a florescent antibody specific for said transgene) as a means to enrich for gene transfer and subsequence expression of the transgene (and co-inserted transgene combinations). By selecting in cell culture those cells in which the reporter gene has been activated, cells can be selected that contain the transgene. In other embodiments, the DNA encoding the transgene can be introduced into a cell via electroporation. In other embodiments, the DNA can be introduced into a cell via lipofection, infection, or transformation. In one embodiment, the electroporation and/or lipofection can be used to transfect fibroblast cells. In a particular embodiment, the transfected fibroblast cells can be used as nuclear donors for nuclear transfer to generate transgenic animals as known in the art and described below.

Cells that have been stained for the presence of a reporter gene can then be sorted by FACS to enrich the cell population such that we have a higher percentage of cells that contain the DNA encoding the transgene of interest. In other embodiments, the FACS-sorted cells can then be cultured for a periods of time, such as 12, 24, 36, 48, 72, 96 or more hours or for such a time period to allow the DNA to integrate to yield a stable transfected cell population.

In one embodiment, the at least four transgenes incorporated and expressed in the transgenic animal of the present invention are introduced by random integration. In another embodiment, at least one of the four transgenes incorporated and expressed in the transgenic animal of the present invention are introduced by random integration. For example, a bi-cistronic vector comprising at least two transgenes is incorporated into the genome by random integration.

(iii) Targeted Genomic Editing:

In exemplary embodiments, the transgenes are incorporated into the animal utilizing genomic editing tools. These tools include, but are not limited to, nucleases and site-specific recombinases. In exemplary embodiments, the method of insertion is facilitated by genome editing methods utilizing genetic editing tools such as, but not limited to, integrases (recombinases), CRISPR/CAS 9 nucleases, TALAN nucleases, Zinc Finger Nucleases.

The transgenes may be targeted to a single locus selected from a native locus, a modified native locus or a transgenic locus (e.g., landing pad). The native locus may be, for example, GGTA1, $ß_4$GalNT2, CMAH, ROSA26, AAVS1. The native locus may be modified, i.e., a modified native locus, such as modified (GGTA1, $ß_4$GalNT2, or CMAH) In exemplary embodiments, the transgenes may be targeted to a landing pad and/or docking site or other stable expression site. In one embodiment, the landing pad or docking vector can be inserted into any locus of interest, e.g. GGTA1, CMAH, $ß_4$Gal, ROSA26, AAVS1 or the transgenes may be targeted to any known "safe harbor" locus, or any predetermined locus that might provide a beneficial gene expression profile, or where the predetermined locus may also inactivate a preferred gene where simultaneous insertion and knockout is beneficial to the transplant outcome. In another embodiment gene editing can be utilized to create the double-strand break, that initiates the DNA repair machinery to create small insertions, deletions, or nucleic acid substitutions (INDELs) resulting in gene activation or knockout at the target site; in such cases an INDEL at one predetermined locus (eg. GGTA1, CMAH, B4GalNT2) could be created in a cell or resulting cloned pig, simultaneously with gene-editing-enhanced knockin of a multicistronic vector at another locus.

In a particular embodiment, gene editing is used to simultaneously (using multiple Crispr-Cas9 guide RNAs, TALEN, or ZFN (or combinations thereof), to inactivate one, two or three endogenous loci in the porcine genome (eg. one or all of GGTA1, CMAH, B4GalNT2), and where one or more of these gene-editing-enhanced modifications also result in targeted insertion of a multicistronic vector with at least four transgenes under control of at least two promoters at one or more of such native or modified native loci.

A. Zinc Finger Nucleases/TALENs

In one embodiment, the transgenes are incorporated utilizing zinc Finger Nucleases (ZFN).

Zinc finger nucleases are fusions of a nonspecific DNA cleavage motif with a sequence-specific zinc finger protein. The nuclease activity is a derivative of the Fold bacterial restriction endonuclease, capable of creating a single strand break. ZFNs operate by dimerizing two DNA-binding domains with two Fold enzymes to produce double-strand breaks with 18 bp specificity.

In another embodiment, the transgenes are incorporated using transcription activator-like effector nucleases (TALENs).

TALENs function like ZFNs to create doublestranded breaks by tethering the Fold endonuclease to DNA binding domains. In this process, the targeting efficiency of TALEN-directed mutagenesis has been reported with efficiencies reaching 73.1% with a 27.8% rate of biallelic knockout. TALENs may be distinguished from ZFNs by their ease of genes design, decreased cost, and marginally improved targeting frequencies.

In one embodiment, the present invention utilizes the direct injection of ZFNs and TALENs into porcine zygotes that could introduce endogenous genes or small insertions or deletions or nucleotide substitutions, and produce piglets with the desired genetic modifications.

B. CRISPR/CAS9 Nuclease

In another embodiment, the transgenes are incorporated utilizing CRISPR/CAS 9 nucleases.

CRISPR/Cas9 is derived from a bacterial defense mechanism that cleaves exogenous DNA by RNA-guided targeting. In bacteria, foreign DNA is digested and inserted into the CRISPR locus, from which CRISPR RNA (crRNA) is made. These short RNA sequences then associate with homologous—presumably foreign-sequences in the genome. When the homologous genomic sequence is followed by an appropriate 'protospacer-adjacent motif' (PAM) at the 3' end, the Cas9 endonuclease creates a double stranded break. The PAM spacer helps prevent the CRISPR-locus itself from being targeted. The CRISPR/Cas9 system has proven to be useful outside of bacteria and was first used to remove alpha Gal from the porcine genome in 2013. The most commonly used system originates from *Streptococcus pyogenes*, which has a 3' PAM sequence of NGG, where N represents any nucleotide. This system allows for the creation of a mutation event in any porcine genomic sequence consisting of $GN_{19}NGG$.

CRISPR/Cas9 system can also be used in conjunction with homology directed repair (HDR), a naturally occurring nucleic acid repair system that is initiated by the presence of double strand breaks (DSBs) in DNA (Liang et al. 1998). More specifically, the CRISPR/Cas9 system can be used to create targeted double strand breaks, it can be used to control the specificity of HDR genome engineering techniques (Findlay et al. 2014; Mali et al. February 2014; Ran et al. 2013). and useful to modify genomes in many organisms, including mammals and humans (Sander and Joung, 2014).

Following the RNA-guided cleavage of a specific site of DNA to create a double stranded break, the DNA fragment or DNA construct of interest can be inserted. This donor template, fragment or construct has the desired insertion or modification, flanked by segments of DNA homologous to the blunt ends of the cleaved DNA. Thus the natural DNA-repair mechanisms of the cell can be used to insert the desired genetic material, editing the genome of a target cell with high-precision, utilizing homology driven recombination combined with any genome editing technique known to create highly targeted double strand breaks. Genome modification carried out in this way can be used to insert novel genes, referred to as "enhanced homology driven insertion or knock-in" is described as the insertion of a DNA and to simultaneously knock out existing genes (Mali et al. February 2013).

The CRISPR/Cas system offers several advantages over previous site-specific nucleases. Foremost, the Cas9 endonuclease represents the first untethered method of DNA cleavage. It is free to associate with multiple guide RNAs and thereby allows for simultaneous targeting of several loci within a single transfection. This has allowed for the efficient combination of multiple genetic knockouts on a single cell. In 2013, the creation of a GGTA1, GGTA1/iGb3S, GGTA1/CMAH, and GGTA1/iGb3S/CMAH homozygous knockout cells was accomplished in a single reaction. The CRISPR/Cas9 system has been successfully used to generate transgenic animals in various vertebrates including zebrafish, monkeys, mice, rats, and pigs see Withworth et al., Biol. Reprod. 91(3):78, pp. 1-13 [2014] and Li et al.; Xenotransplantation 22(1), pp. 20-31 [2015].

Targeting efficiency, or the percentage of desired mutation achieved, is one of the most important parameters by which to assess a genome-editing tool. The targeting efficiency of Cas9 compares favorably with more established methods, such as TALENs or ZFNs. For example, in human cells, custom-designed ZFNs and TALENs could only achieve efficiencies ranging from 1% to 50%. In contrast, the Cas9 system has been reported to have efficiencies up to >70% in zebrafish and plants and ranging from 2-5% in induced pluripotent stem cells.

In one embodiment, the present invention may utilize a CRISPR/Cas9 system to generate transgenic pigs (e.g., ungulate, porcine animal) via micro-injection of CRISPRs designed specifically to target genes of interest into "in vitro" derived zygotes.

In another embodiment, the present invention may utilize a CRISPR/Cas9 system to generate transgenic pigs (e.g., ungulate, porcine animal) by modification of somatic donor cells with CRISPRs designed specifically to target genes of interest, followed by SCNT.

In another embodiment, the present invention may utilize a CRISPR/Cas9 system to generate transgenic pigs (e.g., ungulate, porcine animal) by target a specific region/sequence of an existing genetic modification. More specific embodiment, targeting a sequence of the neomycin gene sequence.

In another embodiment, the present invention may utilize genome editing system such as TALEN, Zinc Finger or CRISPR/Cas9 system to generate transgenic pigs (e.g., ungulate, porcine animal) by targeting a specific region/sequence of an existing genetic modification. More specific embodiment, targeting a single locus that can be a native locus, a modified native locus or a transgenic locus (e.g., landing pad).

In another embodiment the CRISPR/Cas9 system can be used to generate transgenic pigs (e.g., ungulate, porcine animal) by targeting a specific region/sequence of an existing genetic modification via the insertion of a large DNA fragment or construct flanked with arms or segments of DNA homologous to the double strand breaks, utilizing homology driven recombination.

C. Site-Specific Recombinases

In exemplary embodiments, the transgenes are incorporated utilizing site-specific recombinases. specific recombinase technology is widely used to carry out deletions, insertions, translocations and inversions at specific sites in the DNA of cells. It allows the DNA modification to be targeted to a specific cell type or be triggered by a specific external stimulus. It is implemented both in eukaryotic and prokaryotic systems. There are several recombination systems that work efficiently for genetic engineering strategies, The Flp-FRT and Cre-loxP recombinase systems are reversible and thus facilitate both site specific integration and excision. Integrases mediate the genome integration process that catalysis highly site specific recombination reaction that results in the precise integration, excision and/or inversion of DNA. Serine (ΦC31, Bxb1, R4) and tyrosine integrases (λ, P22, HP1) are the two major families of integrases currently applied to genome engineering. In broad, the process of site specific recombination involves the binding of recombinase to recombinase substrate(s) to bring them in close proximity via protein-protein interactions. During the process the substrates are cleaved and DNA ends reorganized in a strand exchange reaction so that the rejoining of the DNA backbone give rise to the recombinant products. In most cases serine integrase is catalyzing highly efficient irreversible recombination using simple att sites.

In order to make use of the high efficiency of site-specific recombinases, a docking site or landing pad comprises an attachment site for recombinase substrate binding sites, e.g. att sites; or the recombination systems, e.g. Flp-FRT and Cre-loxP can be introduced at the desired locus of cell line and/or anima line. This insertion of the docking vector into the target genome is either random or via homologous recombination. This allows for successive rounds of plasmid integration, where the plasmid or vector may contain different transgenes and/or additional DNA sequences. In return the recombination systems, such as Flp/FRT can be used to remove unwanted vector and marker sequences.

(iv) Vectors for Producing Transgenic Animals

Nucleic acid targeting vector constructs can be designed to accomplish homologous recombination in cells. In one embodiment, a targeting vector is designed using a promoter trap, wherein integration at the targeted locus allows the inserted open reading frame of the transgene to utilize the endogenous or native promoter to drive expression of the inserted gene (or inserted selectable marker; eg. Neo or Puro). In a particular embodiment a targeting vector is designed using a "poly(A) trap". Unlike a promoter trap, a poly(A) trap vector captures a broader spectrum of genes including those not expressed in the target cell (i.e. fibroblasts or ES cells). A polyA trap vector includes a constitutive promoter that drives expression of a selectable marker gene lacking a polyA signal. Replacing the polyA signal is a splice donor site designed to splice into downstream exons. In this strategy, the mRNA of the selectable marker gene can be stabilized upon trapping of a polyA signal of an endogenous gene regardless of its expression status in the target cells. In one embodiment, a targeting vector is constructed including a selectable marker that is deficient of signals for polyadenylation.

These targeting vectors can be introduced into mammalian cells by any suitable method including, but not limited, to transfection, transformation, virus-mediated transduction, or infection with a viral vector. In one embodiment, the targeting vectors can contain a 3' recombination arm and a 5' recombination arm (i.e. flanking sequence) that is homologous to the genomic sequence of interest. The 3' and 5' recombination arms can be designed such that they flank the 3' and 5' ends of at least one functional region of the genomic sequence. The targeting of a functional region can render it inactive, which results in the inability of the cell to produce functional protein. In another embodiment, the homologous DNA sequence can include one or more intron and/or exon sequences. In addition to the nucleic acid sequences, the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells. The selectable marker can be located between the 5' and 3' recombination arm sequence.

Modification of a targeted locus of a cell can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al., Nature Biotechnology 20: 251-255, 2002; WO 00/51424. In such example, the selectable marker gene could be a promoterless neomycin phosphtransferase (Neo) gene that not only results in targeted insertion and expression of Neo (by trapping and utilizing the endogenous porcine alpha Gal gene promoter), but functional inactivation of the target locus (eg. GGTA1) from said targeted insertion and interruption of the GGTA1 catalytic domain.

A variety of enzymes can catalyze the insertion of foreign DNA into a host genome. Viral integrases, transposases and site-specific recombinases mediate the integration of virus genomes, transposons or bacteriophages into host genomes. An extensive collection of enzymes with these properties can be derived from a wide variety of sources. Retroviruses combine several useful features, including the relative simplicity of their genomes, ease of use and their ability to integrate into the host cell genome, permitting long-term transgene expression in the transduced cells or their progeny. They have, therefore, been used in a large number of gene-therapy protocols. Vectors based on Lentivirus vectors, have been attractive candidates for both gene therapy and transgenic applications as have sdeno-associated virus, which is a small DNA virus (parvovirus) that is co-replicated in mammalian cells together with helper viruses such as adenovirus, herpes simplex virus or human cytomegalovirus. The viral genome essentially consists of only two ORFs (rep, a non-structural protein, and cap, a structural protein) from which (at least) seven different polypeptides are derived by alternative splicing and alternative promoter usage. In the presence of a helper-virus, the rep proteins mediate replication of the AAV genome. Integration, and thus a latent virus infection, occurs in the absence of helper virus. Transposons are also of interest. These are segments of mobile DNA that can be found in a variety of organisms. Although active transposons are found in many prokaryotic systems and insects, no functional natural transposons exist in vertebrates. The *Drosophila* P element transposon has been used for many years as a genome engineering tool. The sleeping beauty transposon was established from non-functional transposon copies found in salmonid fish and is significantly more active in mammalian cells than prokaryotic or insect transposons. Site-specific recombinases are enzymes that catalyze DNA strand exchange between DNA segments that possess only a limited degree of sequence homology. They bind to recognition sequences that are between 30 and 200 nucleotides in length, cleave the DNA backbone, exchange the two DNA double helices involved and relegate the DNA. In some site-specific recombination systems, a single polypeptide is sufficient to perform all of these reactions, whereas other recombinases require a varying number of accessory proteins to fulfill these tasks. Site-specific recombinases can be clustered into two protein families with distinct biochemical properties, namely tyrosine recombinases (in which the DNA is covalently attached to a tyrosine residue) and serine recombinases (where covalent attachment occurs at a serine residue). The most popular enzymes used for genome modification approaches are Cre (a tyrosine recombinase derived from *E. coli* bacteriophage P1) and phiC31 integrase (a serine recombinase derived from the *Streptomyces* phage phiC31). Several other bacteriophage derived site-specific recombinases (including Flp, lambda integrase, bacteriophage HK022 recombinase, bacteriophage R4 integrase and phage TP901-1 integrase, and bxb1 integrase) have been used successfully to mediate stable gene insertions into mammalian genomes. Recently, a site-specific recombinase has been purified from the *Streptomyces* bacteriophage. The phiC31 recombinase is a member of the resolvase family and mediates phage integration. In this process the bacteriophage attP site recombines with the corresponding attB site in the bacterial genome. The crossover generates two sites, attL and attR, which are no longer a target for recombinase action, in the absence of accessory proteins. The reaction also takes place in mammalian cells and can therefore be used to mediate site-specific integration of therapeutic genes. The site-specificity of tyrosine-recombinases has been difficult to modify by direct protein engineering because the catalytic domain and the DNA recognition domain are closely interwoven. Therefore, changes in specificity are often accompanied by a loss in activity. Serine recombinases might be more amenable to engineering and a hyperactive derivative of Tn3 resolvase has been modified by exchange of the natural DBD for a zinc-finger domain of the human zinc-finger transcription factor Zif268. The DNA site-specificity of the resulting chimeric protein, termed Z-resolvase, had been switched to that of Zif268. Zinc-finger proteins can be modified by in vitro protein evolution to recognize any DNA sequence, therefore, this approach could enable development of chimeric recombinases that can integrate therapeutic genes into precise genomic locations. Methods for enhancing or mediating recombination include the combination of site-specific recombination and homologous recombination, AAV-vector mediated, and zinc-finger nuclease mediated recombination (ref: Geurts et. al., Science, 325: 433, 2009)

The term "vector," as used herein, refers to a nucleic acid molecule (preferably DNA) that provides a useful biological or biochemical property to an inserted nucleic acid. "Expression vectors" according to the invention include vectors that are capable of enhancing the expression of one or more molecules that have been inserted or cloned into the vector, upon transformation of the vector into a cell. Examples of such expression vectors include, phages, autonomously replicating sequences (ARS), centromeres, and other sequences which are able to replicate or be replicated in vitro or in a cell, or to convey a desired nucleic acid segment to a desired location within a cell of an animal. Expression vectors useful in the present invention include chromosomal-, episomal- and virus-derived vectors, e.g., vectors derived from bacterial plasmids or bacteriophages, and vectors derived from combinations thereof, such as cosmids and phagemids or virus-based vectors such as adenovirus, AAV, lentiviruses. A vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575), TA Cloning.RT-PCR, cloning (Invitrogen Corp., Carlsbad, Calif.)) can also be applied to clone a nucleic acid into a vector to be used according to the present invention.

Figure 6:
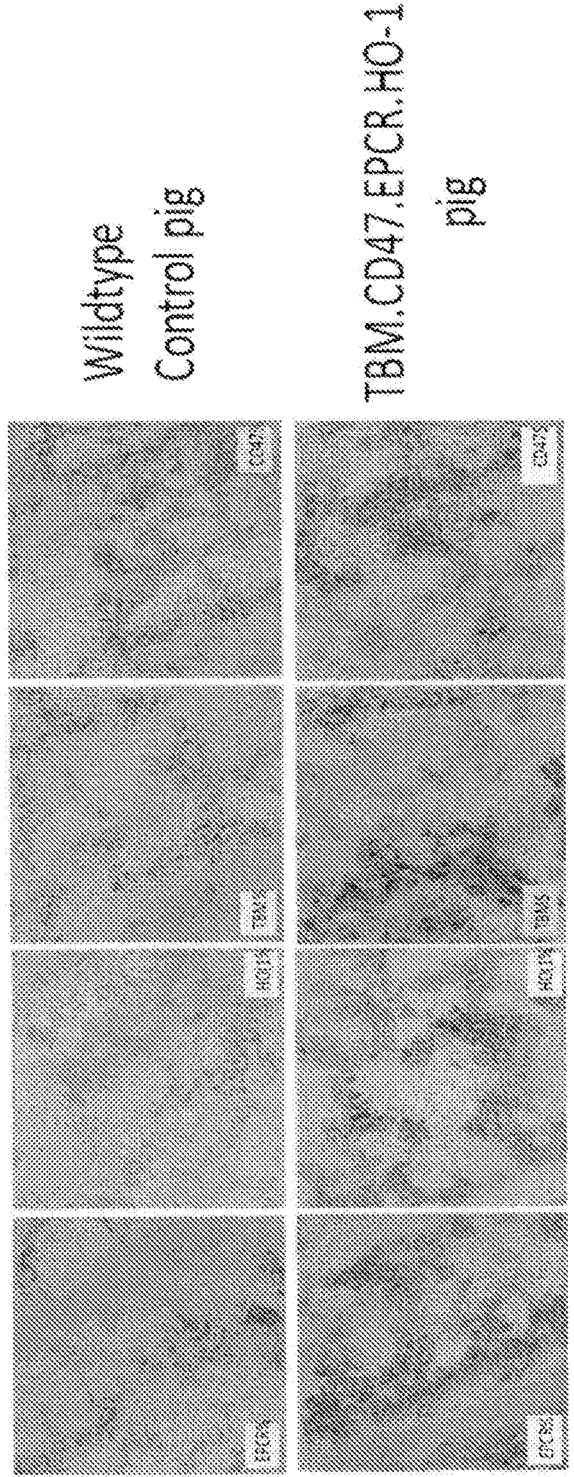
FIG. 6 depicts expression analysis of pREV971 transgenes in lung.
Figure 8:
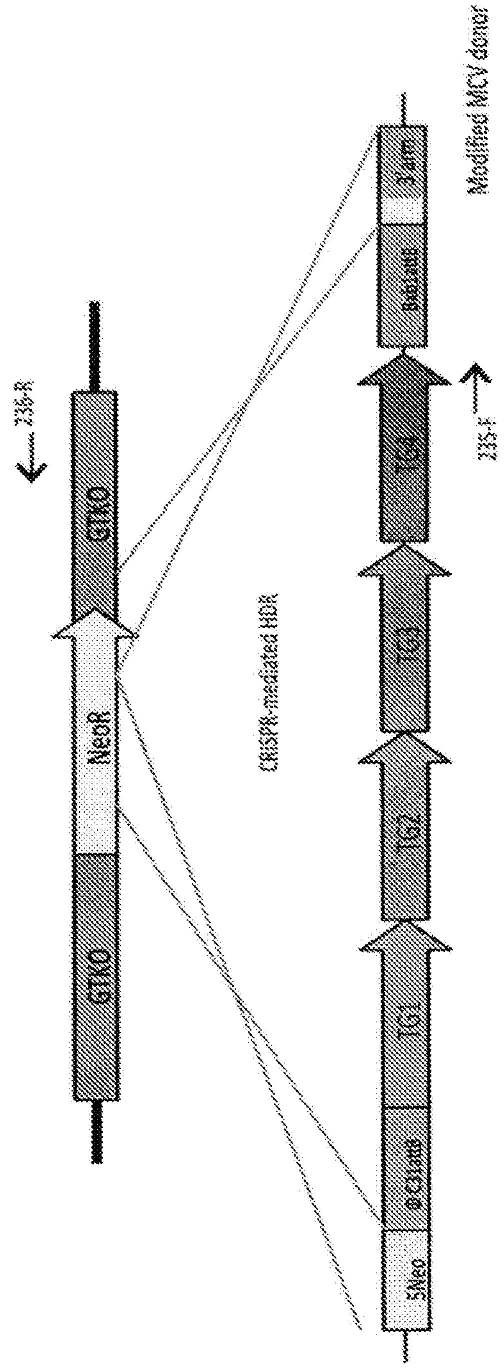
FIG. 8 depicts the 941 HDR vector (MCV vector pREV941—with human transgenes EPCR, DAF, TBM, and CD39); 500 bp homology arms specific for targeting the modified alpha Gal locus in GTKO cells)

Cells homozygous at a targeted locus can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al. (2002) Nature Biotechnology 20: 251-255; WO 00/51424, FIG. 6; and Gene Targeting: A Practical Approach. Joyner, A. Oxford University Press, USA; 2.sup.nd ed. Feb. 15, 2000.

Various constructs can be prepared for homologous recombination at a target locus. Usually, the construct can include at least 25 bp, 50 bp, 100 bp, 500 bp, 1 kbp, 2 kbp, 4 kbp, 5 kbp, 10 kbp, 15 kbp, 20 kbp, or 50 kbp of sequence homologous with the target locus.

Various considerations can be involved in determining the extent of homology of target DNA sequences, such as, for example, the size of the target locus, availability of sequences, relative efficiency of double cross-over events at the target locus and the similarity of the target sequence with other sequences. The targeting DNA can include a sequence in which DNA substantially isogenic flanks the desired sequence modifications with a corresponding target sequence in the genome to be modified. The substantially isogenic sequence can be at least about 95%, 97-98%, 99.0-99.5%, 99.6-99.9%, or 100% identical to the corresponding target sequence (except for the desired sequence modifications). The targeting DNA and the target DNA preferably can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See Song et al. (1987) Proc. Nat'l Acad. Sci. U.S.A. 84:6820-6824. See also Sambrook et al. (1989) Molecular Cloning—A Laboratory Manual, Cold Spring Harbor Laboratory, Cold Spring Harbor, N.Y., see chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo) (Southern, P., and P. Berg, (1982) J. Mol. Appl. Genet. 1:327-341); and the hygromycin resistance gene (hyg) (Nucleic Acids Research 11:6895-6911 (1983), and Te Riele et al. (1990) Nature 348:649-651). Additional reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, blasticidin, zeocin, methotrexate, phosphinothricin, puromycin, and tetracycline. Methods to determine suppression of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Combinations of selectable markers can also be used. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. Selectable markers can also be used for negative selection. Negative selection markets generally kill the cells in which they are expressed either because the expression is per se toxic or produces a catalyst that leads to toxic metabolite, such as Herpes simplex virus Type I thymidine kinase (HSV-tk) or diphtheria toxin A. Generally, the negative selection marker is incorporated into the targeting vector so that it is lost following a precise recombination event. Similarly, conventional selectable markers such as GFP can be used for negative selection using, for example, FACS sorting the insertion of selected transgenes if expressed at significant levels on cell surface could serve as a "selectable marker" for gain or loss of function. Use of the inserted or targeted transgenes as the selection tool allows for positive selection without the use of added florescent markers (eg. GFP, RFP), or antibiotic selection genes. In certain cases, targeted insertion of the transgene may inactivate the target locus, such that loss of function could be monitored or selected for. E.g inactivation of the GGTA1 locus would eliminate or reduce binding of targeted cells to a lectin (1B4), or inactivation of B4GalNT2 would eliminate or reduce binding of targeted cells by DBA lectin, and in each case targeted integration could be sorted for, or enriched, in cells which lack such lectin binding.

Deletions can be at least about 50 bp, more usually at least about 100 bp, and generally not more than about 20 kbp, where the deletion can normally include at least a portion of the coding region including a portion of or one or more exons, a portion of or one or more introns, and can or cannot include a portion of the flanking non-coding regions, particularly the 5-non-coding region (transcriptional regulatory region). Thus, the homologous region can extend beyond the coding region into the 5'-non-coding region or alternatively into the 3-non-coding region. Insertions can generally not exceed 10 kbp, usually not exceed 5 kbp, generally being at least 50 bp, more usually at least 200 bp.

The region(s) of homology can include mutations, where mutations can further inactivate the target gene, in providing for a frame shift, or changing a key amino acid, or the mutation can correct a dysfunctional allele, etc. Usually, the mutation can be a subtle change, not exceeding about 5% of the homologous flanking sequences or even a single nucleotide change such as a point mutation in an active site of an exon. Where mutation of a gene is desired, the marker gene can be inserted into an intron, so as to be excised from the target gene upon transcription.

Various considerations can be involved in determining the extent of homology of target DNA sequences, such as, for example, the size of the target locus, availability of sequences, relative efficiency of double cross-over events at the target locus and the similarity of the target sequence with other sequences. The targeting DNA can include a sequence in which DNA substantially isogenic flanks the desired sequence modifications with a corresponding target sequence in the genome to be modified. The substantially isogenic sequence can be at least about 95%, or at least about 97% or at least about 98% or at least about 99% or between 95 and 100%, 97-98%, 99.0-99.5%, 99.6-99.9%, or 100% identical to the corresponding target sequence (except for the desired sequence modifications). In a particular embodiment, the targeting DNA and the target DNA can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

The construct can be prepared in accordance with methods known in the art, various fragments can be brought together, introduced into appropriate vectors, cloned, analyzed and then manipulated further until the desired construct has been achieved. Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed.

The construct can be prepared using a bacterial vector, including a prokaryotic replication system, e.g. an origin recognizable by *E. coli*, at each stage the construct can be cloned and analyzed. A marker, the same as or different from the marker to be used for insertion, can be employed, which can be removed prior to introduction into the target cell. Once the vector containing the construct has been completed, it can be further manipulated, such as by deletion of the bacterial sequences, linearization, introducing a short deletion in the homologous sequence. After final manipulation, the construct can be introduced into the cell.

Techniques which can be used to allow the DNA or RNA construct entry into the host cell include calcium phosphate/DNA coprecipitation, microinjection of DNA into the nucleus, electroporation, bacterial protoplast fusion with intact cells, transfection, lipofection, infection, particle bombardment, or any other technique known by one skilled in the art. The DNA or RNA can be single or double stranded, linear or circular, relaxed or supercoiled DNA. For various techniques for transfecting mammalian cells, see, for example, Keown et al., Methods in Enzymology Vol. 185, pp. 527-537 (1990).

The following vectors are provided by way of example. Bacterial: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR54O, pRIT5 (Pharmacia). Eukaryotic: pWLneo, pSv2cat, pOG44, pXT1, pSG (Stratagene) pSVK3, pBPv, pMSG, pSVL (Pharmiacia). Also, any other plasmids and vectors can be used as long as they are replicable and viable in the host. Vectors known in the art and those commercially available (and variants or derivatives thereof) can in accordance with the invention be engineered to include one or more recombination sites for use in the methods of the invention. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. Other vectors of interest include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBaclll, pCDM8, pcDNA1, pZeoSV, pcDNA3 pREP4, pCEP4, and pEBVHis (Invitrogen, Corp.) and variants or derivatives thereof.

Other vectors include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSYSPORT1 (Invitrogen) and variants or derivatives thereof.

Viral vectors can also be used, such as lentiviral vectors (see, for example, WO 03/059923; Tiscornia et al. PNAS 100: 1844-1848 (2003)).

Additional vectors of interest include pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pAO81S, pPICZ, pPICZA, pPICZB, pPICZC, pGAPZA, pGAPZB, pGAPZC, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; .lamda. ExCell, .lamda. gt11, pTrc99A, pKK223-3, pGEX-1.lamda. T, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4-abc(+), pOCUS-2, pTAg, pET-32L1C, pET-30LIC, pBAC-2 cp LIC, pBACgus-2 cp LIC, pT7Blue-2 LIC, pT7Blue-2, .lamda. SCREEN-1, .lamda. BlueSTAR, pET-3abcd, pET-7abc, pET9abcd, pET11 abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3 cp, pBACgus-2 cp, pBACsurf-1, pig, Signal pig, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6×His-GFP, pSEAP2-Basic, pSEAP2-Contral, pSEAP2-Promoter, pSEAP2-Enhancer, p.beta.gal-Basic, p.beta.gal-Control, p.beta.gal-Promoter, p.beta.gal-Enhancer, pCMV, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTrip1Ex, 2.lamda.gt10, .lamda.gt11, pWE15, and .lamda. Trip1Ex from Clontech; Lambda ZAP II, pBK-CMV, pBK-RSV, pBluescript II KS+/−, pBluescript II SK+/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS+/−, pBC KS+/−, pBC SK+/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRT.beta.GAL, pNEO.beta.GAL, pRS403, pRS404, pRS405, pRS406, pRS413, pRS414, pRS415, and pRS416 from Stratagene.

Additional vectors include, for example, pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

In an exemplary embodiment, the vector is a bicistronic vector. The bicistronic vector comprises a promoter and two transgenes. In a particular embodiment, the bicistronic vector comprises a promoter and two transgenes linked by a 2A sequence. This embodiment allows for the co-expression of multiple functional transgenes from a single transcript. More specifically, this embodiment utilizes a short (18-24aa) cleavage peptide, “2A”, that allows for co-expression of linked open reading frames to express functional transgenes from a single transcript 2A vector system.

In an exemplary embodiment, the vector is a multi-cistronic vector (MCV). In one embodiment, MCV comprises a promoter and at least four transgenes. In a particular embodiment, the MCV comprises four transgenes linked by 2A peptide sequences, under control of at least two promoters. This embodiment allows for the co-expression of multiple functional transgenes from a single transcript. More specifically, this embodiment utilizes a short (18-24aa) cleavage peptide, “2A”, that allows for co-expression of linked open reading frames to express functional transgenes from a single transcript 2A vector system.

In an exemplary embodiment, the vector is a 2A-peptide MCV vector comprising at least two bi-cistronic units, wherein each bi-cistronic unit contains 2 transgenes. In a particular embodiment one bicistronic unit is controlled by a constitutive or ubiquitous promoter (e.g. CAG), and the second bicistronic unit is controlled by an endothelial or other tissue specific or inducible promoter system. In a certain embodiment, only at least four transgenes are inserted at the single locus but where each is controlled by its own promoter or a total of at least two promoters per single locus insertion.

In an exemplary embodiment, the vector is an 4-gene MCV comprising at least two anticoagulants and more particularly, at least three anticoagulants.

In an exemplary embodiment, the vector is a 4-gene MCV vector comprising at least two anticoagulants and a compliment inhibitor, and more particularly, three anticoagulants and a compliment inhibitor.

In an exemplary embodiment, the vector is a 4-gene MCV vector comprising two anticoagulants, a compliment inhibitor and an immunosuppressant.

Promoters

Vector constructs used to produce the animals of the invention can include regulatory sequences, including, but not limited to, a promoter-enhancer sequence, operably linked to the sequence, “2A” peptide technology and a docking vector. Large numbers of suitable vectors and promoters are known to those of skill in the art, and are commercially available.

In specific embodiments, the present invention provides animals, tissues and cells that express at least one transgene in endothelial cells (in combination with at least one transgene under control of a second same or different promoter), and more particularly, at least two, at least three or at least four transgenes in endothelial cells. To target expression to a particular tissue, the animal is developed using a vector that includes a promoter specific for endothelial cell expression. In a particular embodiment, expression is controlled by a promoter active primarily in endothelium.

In one embodiment, the nucleic acid construct contains a regulatory sequence operably linked to the transgene sequence to be expressed. In one embodiment, the regulatory sequence can be a promoter sequence. In one embodiment, the promoter can be a regulatable promoter. In such systems, drugs, for example, can be used to regulate whether the peptide is expressed in the animal, tissue or organ. For example, expression can be prevented while the organ or tissue is part of the pig, but expression induced once the pig has been transplanted to the human for a period of time to overcome the cellular immune response. In addition, the level of expression can be controlled by a regulatable promoter system to ensure that immunosuppression of the recipient's immune system does not occur. The regulatable promoter system can be selected from, but not limited to, the following gene systems: a metallothionein promoter, inducible by metals such as copper (see Lichtlen and Schaffner, Swiss Med. Wkly., 2001, 131 (45-46):647-52); a tetracycline-regulated system (see Imhof et al., J Gene Med., 2000, 2(2): 107-16); an ecdysone-regulated system (see Saez et al., Proc Natl Acad Sci USA., 2000, 97(26): 14512-7); a cytochrome P450 inducible promoter, such as the CYPlA1 promoter (see Fujii-Kuriyama et al., FASEB J., 1992, 6(2): 706-10); a mifepristone inducible system (see Sirin and Park, Gene., 2003, 323:67-77); a coumarin-activated system (see Zhao et al., Hum Gene Ther., 2003, 14(17): 1619-29); a macrolide inducible system (responsive to macrolide antibiotics such as rapamycin, erythromycin, clarithromycin, and roxitiromycin) (see Weber et al., Nat Biotechnol., 2002, 20(9):901-7; Wang et al., Mol Ther., 2003, 7(6):790-800); an ethanol induced system (see Garoosi et al., J Exp Bot., 2005, 56(416): 163542; Roberts et al., Plant Physiol., 2005, 138 (3): 1259-67); a streptogramin inducible system (see Fussenegger et al., Nat Biotechnol., 2000 18(11):1203-8) an electrophile inducible system (see Zhu and Fahl, Biochem Biophys Res Commun., 2001, 289(1):212-9); a nicotine inducible system (see Malphettes et al., Nucleic Acids Res., 2005, 33(12):e107), immune-inducible promoter, cytokine response promoters (e.g. promoters that are induced by IFN-gamma, TNF-alpha, IL-1, IL-6 or TGF-beta (or other secondary pathways), and thus can be turned on or upregulated in association with or in response to an immune or inflammatory response.

In a particular embodiment, the bicistronic vector includes two transgenes and a promoter that is active primarily in endothelial cells or a constitutive promoter that ubiquitously expresses transgenes in all organs, tissues and cells. In other embodiments the at least four transgenes in a multicistronic vector (MCV) are under control of at least two promoters. The promoters may be exogenous, native or a combination of both exogenous and native.

In a particular embodiment, the bi-cistronic vector includes two transgenes and a constitutive promoter that ubiquitously expresses transgenes in all organs, tissues and cells.

In a particular embodiment, the bi-cistronic vector includes two transgenes and a tissue specific promoter controlling expression in organs, tissues and cells In an exemplary embodiment, the vector is a four-gene MCV comprising at least two anticoagulants under the control of an endothelial-specific promoter.

In an exemplary embodiment, the vector is a four-gene MCV comprising at least one compliment inhibitor transgene under the control of a constitutive promoter and at least one anticoagulant transgene under the control of an endothelial-cell specific promoter In an exemplary embodiment, the vector is a four-gene MCV comprising at least one compliment inhibitor transgene under the control of a constitutive promoter and at least one anticoagulant gene under the control of a second constitutive promoter.

In an exemplary embodiment, the vector is a four-gene MCV vector comprising an anticoagulant transgene and an immunosuppressant transgene under the control of an endothelial-cell promoter.

In an exemplary embodiment the vector is a two-gene MCV vector comprising a total of two genes under control of at least two separate promoters; or in a selected embodiment a vector with multiple transgenes in a string, each with their own promoter, and all integrated into a single locus.

In other embodiments an enhancer element is used in the nucleic acid construct to facilitate increased expression of the transgene in a tissue-specific manner. Enhancers are outside elements that drastically alter the efficiency of gene transcription (Molecular Biology of the Gene, Fourth Edition, pp. 708-710, Benjamin Cummings Publishing Company, Menlo Park, Calif. COPYRGT. 1987). In a particular embodiment, the pdx-1 enhancer (also known as IPF-1, STF-1, and IDX1 (Gerrish K et al., Mol. Endocrinol., 2004, 18(3): 533; Ohlsson et al., EMBO J. 1993 November, 12(11):4251-9; Leonard et al., Mol. Endocrinol., 1993, 7(10):1275-83; Miller et al., EMBO J., 1994, 13(5):1145-56; Serup et al., Proc Natl Acad Sci USA., 1996, 93(17):9015-20; Melloul et al., Diabetes., 2002, 51 Suppl 3:S320-5; Glick et al., J Biol Chem., 2000, 275(3):2199-204; GenBank AF334615.)) is used in combination with the ins2 promoter, for pancreas specific expression of the transgene(s). In certain embodiments, the animal expresses a transgene under the control of a promoter in combination with an enhancer element. In particular embodiments, the animal includes an endothelial specific promoter, such as a porcine ICAM-2 or murine Tie-2 promoter, and further includes an enhancer element (e.g., murine Tie-2 enhancer or CMV enhancer). In other embodiments, the promoter can be a ubiquitous promoter element that further includes an enhancer element. In a particular element the ubiquitous promoter is CAG (CMV enhancer, chicken beta-Actin promoter, rabbit beta-globin intron) used in combination with a endothelium-specific Tie-2 enhancer element (Tie2-CAG). For Tie2-CAG, the transgene(s) would be expected to be expressed in both a constitutive and ubiquitous manner, but at an even higher level in endothelial cells versus other body cells. In some embodiments, the promoter is used in combination with an enhancer element which is a non-coding or intronic region of DNA intrinsically associated or co-localized with the promoter. In another specific embodiment, the enhancer element is ICAM-2 used in combination with the ICAM-2 promoter. Other ubiquitous promoters include, but are not limited to the following: viral promoters like CMV and SV40, also chicken beta actin and gamma-actin promoter, GAPDH promoters, H2K, CD46 promoter, GGTA1, ubiquitin and the ROSA promoter.

(v) Selection of Genetically Modified Cells

In some cases, the transgenic cells have genetic modifications that are the result of targeted transgene insertion or integration (i.e. via homologous recombination) into the cellular genome. In some cases, the transgenic cells have genetic modification that are the result of non-targeted (random) integration into the cellular genome. The cells can be grown in appropriately-selected medium to identify cells providing the appropriate integration. Those cells which show the desired phenotype can then be further analyzed by restriction analysis, electrophoresis, Southern analysis, polymerase chain reaction, or another technique known in the art. By identifying fragments which show the appropriate insertion at the target gene site, (or, in non-targeted applications, where random integration techniques have produced the desired result) cells can be identified in which homologous recombination (or desired non-targeted integration events) has occurred to inactivate or otherwise modify the target gene.

The presence of the selectable marker gene or other positive selection agent or trangene establishes the integration of the target construct into the host genome. Those cells which show the desired phenotype can then be further analyzed by restriction digest analysis, electrophoresis, Southern analysis, polymerase chain reaction, etc. to analyze the DNA in order to establish whether homologous or non-homologous recombination occurred. This can be determined by employing probes for the insert and then sequencing the 5' and 3' regions flanking the insert for the presence of the gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. For example, by demonstrating the presence of the primer sequences or the expected size sequence, the occurrence of homologous recombination is supported.

The polymerase chain reaction used for screening homologous recombination events is described in Kim and Smithies, (1988) Nucleic Acids Res. 16:8887-8903; and Joyner et al. (1989) Nature 338:153-156.

The cell lines obtained from the first round of targeting (or from non-targeted (random) integration into the genome) are likely to be heterozygous for the integrated allele.

Homozygosity, in which both alleles are modified, can be achieved in a number of ways. One approach is to grow up a number of cells in which one copy has been modified and then to subject these cells to another round of targeting (or non-targeted (random) integration) using a different selectable marker. Alternatively, homozygotes can be obtained by breeding animals heterozygous for the modified allele. In some situations, it can be desirable to have two different modified alleles. This can be achieved by successive rounds of gene targeting (or random integration) or by breeding heterozygotes, each of which carries one of the desired modified alleles. An event of genome editing with efficient targeted double-stranded breaks allows for frequent biallelic gene targeting event such that in a single transfection (or embryo or zygote targeting strategy), homozygousys knock out or knockin events can be achieved with high frequency. Such gene-editing-enhanced (e.g. Crispr-CAS9 nuclease) gene targeting or homology-dependent repair events, can include both monoallelic or heterozygous, and biallelic or homozygous knockout (via small nucleotide insertions, deletions, substitutions, otherwise described as INDELs), and also gene insertions, including both monallelic and biallelic insertion/knockin of a single transgene, multi-transgene string (strings of transgenes under their own promoters or bicistronic or multicistronic), or multicistronic vectors (including 4-transgene multicistonic vectors under control of at least 2 promoters where said promoters could be constitutive or tissue-specific, e.g., CAG and Icam-2). Alternatively, via use of multiple gene editing nucleases (e.g. Crispr/Cas9), one could expect to efficiently produce a cell (via transfection or infection) or zygote (simultaneously via microinjection) with a combination of base genotype (ie. GGTA1 knockout or GGTA1/CD46), where one genetic modification might include knockin (e.g., at GGTA1), or random insertion, of a 4-gene MCV (under control of at least two promoters), and simultaneously, either a nuclease-mediated INDEL at another locus (mono or biallelic, e.g., at GGTA1 or CMAH or B4GalNT2), or in a preferred embodiment, a targeted insertion of a multitransgene vector (bicistronic or 4-gene MCV) at two different loci (landing pads, safe harbor, or GGTA1, B4GalNT2, CMAH, ROSA26, AAVS1 or other predetermined locus, including native or modified native loci), for example targeted insertion of a 4-gene MCV at GGTA1 along with targeted, homologous recombination (or gene-editing-enhanced) insertion of a bicistronic or 4-gene MCV at a second locus (e.g., CMAH or B4GalNT2). In certain embodiments, a selection technique is used to obtain homologous knockout cells from heterozygous cells by exposure to very high levels of a selection agent. Such a selection can be, for example, by use of an antibiotic such as geneticin (G418).

Cells that have been transfected or otherwise received an appropriate vector can then be selected or identified via genotype or phenotype analysis. In one embodiment, cells are transfected, grown in appropriately-selected medium to identify cells containing the integrated vector. The presence of the selectable marker gene indicates the presence of the transgene construct in the transfected cells. Those cells which show the desired phenotype can then be further analyzed by restriction analysis, electrophoresis, Southern analysis, polymerase chain reaction, etc to analyze the DNA in order to verify integration of transgene(s) into the genome of the host cells. Primers can also be used which are complementary to transgene sequence(s). The polymerase chain reaction used for screening homologous recombination and random integration events is known in the art, see, for example, Kim and Smithies, Nucleic Acids Res. 16:8887-8903, 1988; and Joyner et al., Nature 338:153-156, 1989. The specific combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in Teratocarcinoma Stem Cell, eds. Siver, Martin and Strikland (Cold Spring Harbor Lab., Cold Spring Harbor, N.Y. (pp. 469-497); and Linney and Donerly, Cell 35:693-699, 1983.

Cells that have undergone homologous recombination can be identified by a number of methods. In one embodiment, the selection method can detect the absence of an immune response against the cell, for example by a human anti-gal antibody. In a preferred embodiment, the selection method can utilize the inserted or targeted transgenes as the selection tool allows for positive selection without the use of added florescent markers (eg. GFP, RFP), or antibiotic selection genes. In certain cases, targeted insertion of the transgene may produce a cell surface protein, which with appropriate transgene specific florescence-marked cells can be sorted for positive expression of the desired transgene. Alternatively, one could inactivate the target locus, such that loss of function could be monitored or selected for. E.g inactivation of the GGTA1 locus would eliminate or reduce binding of targeted cells to a lectin (IB4), or inactivation of B4GalNT2 would eliminate or reduce binding of targeted cells by DBA lectin, and in each case targeted integration could be sorted for, or enriched, in cells which lack such lectin binding. In each case expression of the transgenes on the cell surface allows the selection of cells to be used for further analysis.

In other embodiments, the selection method can include assessing the level of clotting in human blood when exposed to a cell or tissue. Selection via antibiotic resistance has been used most commonly for screening. This method can detect the presence of the resistance gene on the targeting vector, but does not directly indicate whether integration was a targeted recombination event or a random integration. Alternatively, the marker can be a fluorescent marker gene such as GFP or RFP, or a gene that is detectable on the cell surface via cell sorting or FACs analysis.

Certain technology, such as Poly A and promoter trap technology, increase the probability of targeted events, but again, do not give direct evidence that the desired phenotype has been achieved. In addition, negative forms of selection can be used to select for targeted integration; in these cases, the gene for a factor lethal to the cells (e.g. Tk or diptheria A toxin) is inserted in such a way that only targeted events allow the cell to avoid death. Cells selected by these methods can then be assayed for gene disruption, vector integration and, finally, gene depletion. In these cases, since the selection is based on detection of targeting vector integration and not at the altered phenotype, only targeted knockouts, not point mutations, gene rearrangements or truncations or other such modifications can be detected.

Characterization can be further accomplished by the following techniques, including, but not limited to: PCR analysis, Southern blot analysis, Northern blot analysis, specific lectin binding assays, and/or sequencing analysis. Phenotypic characterization can also be accomplished, including by binding of anti-mouse antibodies in various assays including immunofluoroescence, immunocytochemistry, ELISA assays, flow cytometry, western blotting, testing for transcription of RNA in cells such as by RT-PCR. Genotype can be determined by Southern analysis and PCR. Gene expression is monitored by flow cytometry of PBMCs and endothelial cells, and in cells and organs by immunohistochemistry, Q-PCR (quantitative polymerase chain reaction) and Western blot analysis. Bioactivity assays specific to the transgenes will quantitate and characterize complement inhibition, platelet aggregation, activated protein C formation, ATPase activity, Factor Xa cleavage, mixed lymphocyte reaction (MLR) and apoptosis.

In other embodiments, GTKO animals or cells contain additional genetic modifications. Genetic modifications can include more than just homologous targeting, but can also include random integrations of exogenous genes, co-integration of a group or string of genes at a single locus, mutations, deletions and insertions of genes of any kind. The additional genetic modifications can be made by further genetically modifying cells obtained from the transgenic cells and animals described herein or by breeding the animals described herein with animals that have been further genetically modified. Such animals can be modified to eliminate the expression of at least one allele of .alpha.GT gene, the CMP-Neu5Ac hydroxylase gene (see, for example, U.S. Pat. No. 7,368,284), the iGb3 synthase gene (see, for example, U.S. Patent Publication No. 2005/0155095), and/or ß1,4 N-acetylgalactosaminyl transferase ($ß_4$GalNT2; see for example Estrada J L et al., Xenotransplantation 22:194-202 [2015]) the Forssman synthase gene (see, for example, U.S. Patent Publication No. 2006/0068479).

In additional embodiments, the animals described herein can also contain genetic modifications to express transgenes of interest, more specifically human transgenes that are from the group consisting of immunomodulators, anticoagulants and cytoprotective transgenes. In a preferred embodiment, in addition to multitransgene integration (targeted or random, but exceeding at least 4 genes and where such at least 4 genes are controlled by at least two promoters), genetic modification of the porcine vWF locus can be achieved, including knockout (lack of function), INDELs, and simultaneous knockout of porcine vWF sequences in the genome, or including targeted knockin and replacement of some or all of defined porcine vWF exons (e.g. exons 22-28), with their human exon 22-28 counterparts from the human vWF gene sequence.

To achieve these additional genetic modifications, in one embodiment, cells can be modified to contain multiple genetic modifications. In other embodiments, animals can be bred together to achieve multiple genetic modifications. In one specific embodiment, animals, such as pigs, produced according to the process, sequences and/or constructs described herein, can be bred with animals, such as pigs, lacking expression of alpha Gal (for example, as described in WO 04/028243).

In another embodiment, the expression of additional genes responsible for xenograft rejection can be eliminated or reduced. Such genes include, but are not limited to the CMP-NEUAc Hydroxylase Gene (CMAH), Beta-4GalNT2, the isoGloboside 3 (iGb3) Synthase gene, and the Forssman synthase gene.

In addition, genes or cDNA encoding complement related proteins, which are responsible for the suppression of complement mediated lysis can also be expressed in the animals and tissues of the present invention. Such genes include, but are not limited to CD59, DAF (CD55), and CD46 (see, for example, WO 99/53042; Chen et al. Xenotransplantation, Volume 6 Issue 3 Page 194-August 1999, which describes pigs that express CD59/DAF transgenes; Costa C et al, Xenotransplantation. 2002 January; 9(1):45-57, which describes transgenic pigs that express human CD59 and H-transferase; Zhao L et al.; Diamond L E et al. Transplantation. 2001 Jan. 15; 71(1): 132-42, which describes a human CD46 transgenic pigs.)

Additional modifications can include expression of compounds, such as antibodies, which down-regulate the expression of a cell adhesion molecule by the cells, such as described in WO 00/31126, entitled "Suppression of xenograft rejection by down regulation of a cell adhesion molecules" and compounds in which co-stimulation by signal 2 is prevented, such as by administration to the organ recipient of a soluble form of CTLA-4 from the xenogeneic donor organism, for example as described in WO 99/57266, entitled "Immunosuppression by blocking T cell co-stimulation signal 2 (B7/CD28 interaction)".

(vi) Nuclear Transfer

Genetically modified or transgenic animals such as ungulates or pigs described herein may be produced using any suitable techniques known in the art. These techniques include, but are not limited to, microinjection (e.g., of pronuclei and/or cytoplasmic), electroporation of ova or zygotes, and/or somatic cell nuclear transfer (SCNT).

Any additional technique known in the art may be used to introduce the transgene, or multi-transgene or MCV vector (s) into animals. Such techniques include, but are not limited to pronuclear microinjection (see, for example, Hoppe, P. C. and Wagner, T. E., 1989, U.S. Pat. No. 4,873,191); cytoplasmic microinjection (see for example Whitworth et al., 2014): retrovirus mediated gene transfer into germ lines (see, for example, Van der Putten et al., 1985, Proc. Natl. Acad. Sci., USA 82:6148-6152); gene targeting in embryonic stem cells (see, for example, Thompson et al., 1989, Cell 56:313-321; Wheeler, M. B., 1994, WO 94/26884); electroporation of embryos (see, for example, Lo, 1983, Mol Cell. Biol. 3:1803-1814); transfection; transduction; retroviral infection; adenoviral infection; adenoviral-associated infection; liposome-mediated gene transfer; naked DNA transfer; and sperm-mediated gene transfer (see, for example, Lavitrano et al., 1989, Cell 57:717-723); etc. For a review of such techniques, see, for example, Gordon, 1989, Transgenic Anithals, Intl. Rev. Cytol. 115:171-229. In particular embodiments, the expression of CTLA4 and/or CTLA4-Ig fusion genes in ungulates can be accomplished via these techniques.

In one embodiment, microinjection of the constructs encoding the transgene can be used to produce the transgenic animals. In one embodiment, the nucleic acid construct or vector can be microinjection into the pronuclei of a zygote. In one embodiment, the construct or vector can be injected into the male pronuclei of a zygote. In another embodiment, the construct or vector can be injected into the female pronuclei of a zygote. In a further embodiment, the construct or vector, CRISPR(s), Messenger RNA (mRNA) coding for Cas9 and gRNA (single guided RNA), can be injected into the cytoplasm of fertilized oocytes either to achieve gene knockout or gene inactivation (insertions, deletions, substitutions) resulting from repair errors following treatment with such gene editing nucleases, or can be used to achieve targeted knockin of a transgene(s) or multigene vector in such zygotes, resulting in stable transmission of the genetic modification (reference, Whitworth 2014?). In another embodiment, nuclear transfer can be initiated with an existing transgenic somatic cell, and following embryo reconstruction and fusion, the gene editing nuclease (eg. Crispr/Cas9) can be injected into the cytoplasm of the reconstructed nuclear-transfer embryo, with or without a transgene vector, or multigene vector or MCV, such that the gene editing event occurs in the diploid embryo, and in the subsequent transgenic pig following embryo transfer.

Microinjection of the transgene construct or vector can include the following steps: superovulation of a donor female; surgical removal of the egg, fertilization of the egg; injection of the transgene transcription unit into the was injected into the cytoplasm of fertilized oocytes at postfertilization (e.g. presumptive zygotes at approximately 14 hours post-fertilization), and introduction of the transgenic embryo into the reproductive tract of a pseudopregnant host mother, usually of the same species. See for example U.S. Pat. No. 4,873,191, Brinster, et al. 1985. PNAS 82:4438; Hogan, et al., in "Manipulating the Mouse Embryo: A Laboratory Manual". Cold Spring Harbor Laboratory, Cold Spring Harbor, N.Y., 1986. Robertson, 1987, in Robertson, ed. "Teratocarcinomas and Embryonic Stem Cells a Practical Approach" IRL Press, Evnsham. Oxford, England. Pedersen, et al., 1990. "Transgenic Techniques in Mice-A Video Guide", Cold Spring Harbor Laboratory, Cold Spring Harbor, N.Y. Transgenic pigs are routinely produced by the microinjection of a transgene construct or vector into pig embryos, see Withworth et al., Biol. Reprod. 91(3):78, 1-13 [2014]. In one embodiment, the presence of the transgene can be detected by isolating genomic DNA from tissue from the tail of each piglet and subjecting about 5 micrograms of this genomic DNA to nucleic acid hybridization analysis with a transgene specific probe. In a particular embodiment, transgenic animals can be produced according to any method known to one skilled in the art, for example, as disclosed in Bleck et al., J. Anim. Sci., 76:3072 [1998]; also described in U.S. Pat. Nos. 6,872,868; 6,066,725; 5,523,226; 5,453,457; 4,873,191; 4,736,866; and/or PCT Publication No. WO/9907829.

In one embodiment, the pronuclear microinjection method can include linking at least approximately 50, 100, 200, 300, 400 or 500 copies of the transgene-containing construct or vector of the present invention to a promoter of choice, for example, as disclosed herein, and then the foreign DNA can be injected through a fine glass needle into fertilized eggs. In one embodiment, the DNA can be injected into the male pronucleus of the zygote. Pig zygotes are opaque and visualization of nuclear structures can be difficult. In one embodiment, the pronuclei or nuclei of pig zygotes can be visualized after centrifugation, for example, at 15000 g for 3 mm. The injection of the pronucleus can be carried out under magnification and use of standard microinjection apparatus. The zygote can be held by a blunt holding pipette and the zona pellucida, plasma membrane and pronuclear envelope can be penetrated by an injection pipette. The blunt holding pipette can have a small diameter, for example, approximately 50 um. The injection pipette can have a smaller diameter than the holding pipette, for example, approximately 15 um. DNA integration occurs during replication as a repair function of the host DNA. These eggs, containing the foreign DNA, can then be implanted into surrogate mothers for gestation of the embryo according to any technique known to one skilled in the art.

In some embodiments, pronuclear microinjection can be performed on the zygote 12 hours post fertilization. Uptake of such genes can be delayed for several cell cycles. The consequence of this is that depending on the cell cycle of uptake, only some cell lineages may carry the transgene, resulting in mosaic offspring. If desired, mosaic animals can be bred to form true germline transgenic animals.

In an exemplary embodiment, the cytoplasmic microinjection method can inject CRISPRs targeting at least one or more targeted native gene, or modified native locus, m RNA coding for Cas9 and gRNA through a fine glass needle into fertilized eggs. In a particular embodiment, CRISPRs targeting at least one or more targeted gene (e.g. GGTA1, B4GalNT2, CMAH, and including multiple guide RNAs, along with mRNA coding for Cas9 and gRNA can be injected into the cytoplasm of the zygote.

Somatic Cell Nuclear Transfer

In other embodiments, ungulate cells such as porcine cells containing transgenes can be used as donor cells to provide the nucleus for nuclear transfer into enucleated oocytes to produce cloned, transgenic animals. In one embodiment, the ungulate cell need not express the transgene protein in order to be useful as a donor cell for nuclear transfer. In one embodiment, the porcine cell can be engineered to express a transgene from a nucleic acid construct or vector that contains a promoter. Alternatively, the porcine cells can be engineered to express transgene under control of an endogenous promoter through homologous recombination. In one embodiment, the transgene nucleic acid sequence can be inserted into the genome under the control of a tissue specific promoter, tissue specific enhancer or both. In another embodiment, the transgene nucleic acid sequence can be inserted into the genome under the control of a constitutive promoter. In certain embodiments, targeting vectors are provided, which are designed to allow targeted homologous recombination in somatic cells. These targeting vectors can be transformed into mammalian cells to target the endogenous genes of interest via homologous recombination. In one embodiment, the targeting construct inserts both the transgene nucleotide sequence and a selectable maker gene into the endogenous gene so as to be in reading frame with the upstream sequence and produce an active fusion protein. Cells can be transformed with the constructs using the methods of the invention and are selected by means of the selectable marker and then screened for the presence of recombinants.

The present invention provides a method for cloning an ungulate such as a pig containing certain transgenes via SCNT. In general, the pig can be produced by a nuclear transfer process comprising the following steps: obtaining desired differentiated pig cells to be used as a source of donor nuclei; obtaining oocytes from a pig; enucleating said oocytes; transferring the desired differentiated cell or cell nucleus into the enucleated oocyte, e.g., by fusion or injection, to form SCNT units; activating the resultant SCNT unit; and transferring said cultured SCNT unit to a host pig such that the SCNT unit develops into a fetus.

Nuclear transfer techniques or nuclear transplantation techniques are known in the art (see, for example, Dai et al. Nature Biotechnology 20:251-255; Polejaeva et al Nature 407:86-90 (2000); Campbell, et al., Theriogenology 68 Suppl 1:S214-3 1 (2007); Vajta, et al., Reprod Fertil Dev 19(2): 403-23 (2007); Campbell et al. (1995) Theriogenology, 43:181; Collas et al. (1994) Mol. Report Dev., 38:264-267; Keefer et al. (1994) Biol. Reprod., 50:935-939; Sims et al. (1993) Proc. Natl. Acad. Sci., USA, 90:6143-6147; WO 94/26884; WO 94/24274, and WO 90/03432, U.S. Pat. Nos. 4,944,384, 5,057,420, WO 97/07669, WO 97/07668, WO 98/30683, WO 00/22098, WO 004217, WO 00/51424, WO 03/055302, WO 03/005810, U.S. Pat. Nos. 6,147,276, 6,215,041, 6,235,969, 6,252,133, 6,258,998, 5,945,577, 6,525,243, 6,548,741, and Phelps et al. (Science 299:411-414 (2003)).

A donor cell nucleus, which has been modified to contain a transgene of the present invention, is transferred to a recipient porcine oocyte. The use of this method is not restricted to a particular donor cell type. The donor cell can be as described in Wilmut et al. (1997) Nature 385:810; Campbell et al. (1996) Nature 380:64-66; or Cibelli et al. (1998) Science 280:1256-1258. All cells of normal karyotype, including embryonic, fetal and adult somatic cells which can be used successfully in nuclear transfer can in principle be employed. Fetal fibroblasts are a particularly useful class of donor cells. Generally suitable methods of nuclear transfer are described in Campbell et al. (1995) Theriogenology 43:181, Collas et al. (1994) Mol. Reprod. Dev. 38:264-267, Keefer et al. (1994) Biol. Reprod. 50:935-939, Sims et al. (1993) Proc. Nat'l. Acad. Sci. USA 90:6143-6147, WO-A-9426884, WO-A-9424274, WO-A-9807841, WO-A-9003432, U.S. Pat. Nos. 4,994,384 and 5,057,420, Campbell et al., (2007) Theriogenology 68 Suppl 1, S214-231, Vatja et al., (2007) Reprod Fertil Dev 19, 403-423). Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (see, for example, Campbell et al. (1996) Nature, 380:64-68) and Stice et al. (1996) Biol. Reprod., 20 54:100-110). In a particular embodiment, fibroblast cells, such as porcine fibroblast cells can be genetically modified to contain the transgene of interest.

Methods for isolation of oocytes are well known in the art. Essentially, this can comprise isolating oocytes from the ovaries or reproductive tract of a pig. A readily available source of pig oocytes is slaughterhouse materials. For the combination of techniques such as porcine IVF (in vitro fertilization), SCNT, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration and in the case of porcine generally occurs at about 35-55 hours. This period of time is known as the maturation period."

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated porcine 35 to 48, or 39-41, hours past the onset of estrus or past the injection of human chorionic gonadotropin (hCG) or similar hormone.

After a fixed time maturation period, the oocytes can be enucleated. Prior to enucleation the oocytes can be removed and placed in appropriate medium, such as HECM or TCM199 containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM or TCM199, optionally containing 7-10 micrograms per milliliter cytochalasin B, for immediate enucleation, or can be placed in a suitable medium, for example an embryo culture medium such as PZM or CRlaa, plus 10% estrus cow serum, and then enucleated later, for example not more than 24 hours later or 16-18 hours later.

Enucleation can be accomplished microsurgically using a micropipette to remove the polar body and the adjacent cytoplasm. The oocytes can then be screened to identify those of which have been successfully enucleated. One way to screen the oocytes is to stain the oocytes with 3-10 microgram per milliliter 33342 Hoechst dye in suitable holding medium, and then view the oocytes under ultraviolet irradiation for less than 10 seconds. The oocytes that have been successfully enucleated can then be placed in a suitable holding medium, for example, HECM or TCM 199.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. For example, the fusion media can comprise a 280 milli molar (mM) solution of mannitol, containing 0.05 mM MgCl.sub.2 and 0.001 mM CaCl.sub.2 (Walker et al., Cloning and Stem Cells. 2002; 4(2): 105-12). Fusion can also be accomplished using Sendai virus as a fusogenic agent (Graham, Wister Inot. Symp. Monogr., 9, 19, 1969). Also, the nucleus can be injected directly into the oocyte rather than using electroporation fusion. See, for example, Collas and Barnes, (1994) Mol. Reprod. Dev., 38:264-267. After fusion, the resultant fused NT units are then placed in a suitable medium until activation, for example, HECM or TCM199, until activation, 1-4 hours later. Typically activation can be effected shortly thereafter, for example less than 24 hours later, or about 4-9 hours later for bovine NT and 1-4 hours later for porcine NT.

The NT unit can be activated by known methods. Such methods include, for example, culturing the NT unit at sub-physiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prelusion oocytes to yield greater numbers of viable pregnancies and multiple genetically identical calves after nuclear transfer. Also, treatments such as electrical and chemical shock can be used to activate NT embryos after fusion. See, for example, U.S. Pat. No. 5,496,720 to Susko-Parrish et al. Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units can then be cultured until they reach a suitable size for transferring to a recipient female, or alternately, they may be immediately transferred to a recipient female. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's Whitten's media, PZM, NCSU23 and NCSU37. See Yoshioka K, Suzuki C, Tanaka A, Anas I M, Iwamura S. Biol Reprod. (2002) January; 66(1):112-9 and Petters R M, Wells K D. J Reprod Fertil Suppl. 1993; 48:61-73.

Afterward, the cultured NT unit or units can be washed and then placed in a suitable media contained in well plates which can optionally contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. NT units can be cultured until at least about 2 to 400 cells, about 4 to 128 cells, or at least about 50 cells. Alternatively, NT units may be immediately transferred to a recipient female.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. See, for example, Siedel, G. E., Jr. (1981) "Critical review of embryo transfer procedures with cattle in Fertilization and Embryonic Development in Vitro, L. Mastroianni, Jr. and J. D. Biggers, ed., Plenum Press, New York, N.Y., page 323. Porcine embryo transfer can be conducted according to methods known in the art. For reference, see Youngs et al. "Factors Influencing the Success of Embryo Transfer in the Pig," Theriogenology (2002) 56: 1311-1320.

Multi-Transgenic Animal Breeding Herd

Animals (or fetuses) of the present invention can be reproduced according to the following means, including, but not limited to the group selected from: SCNT, natural breeding, rederivation via SCNT using cells from an existing cell line, fetus, or animal as nuclear donors—optionally adding additional transgenes to these cells prior to NT, sequential nuclear transfer, artificial reproductive technologies (ART) or any combination of these methods or other methods known in the art. In general, "breeding" or "bred" refers to any means of reproduction, including both natural and artificial means. Further, the present invention provides for all progeny of animals produced by the methods disclosed herein. It is understood that in certain embodiments such progeny can become homozygous for the genes described herein.

In one embodiment, the genetically modified animal produced by multicistronic vector design can be bred to an animal produced by a different multicistronic vector. In particular, each multicistronic vector would be comprised of four different transgenes and a two different promoter/enhancer system.

In another embodiment transgenic animals with different multicistronic vectors, thus having different transgenes, can be bred together and have a gene repertoire that equals eight different transgenes where expression of these genes are under control of their different promoter/enhancer systems.

E. Genetically Modified Organs, Organ Fragments, Tissues or Cells

In one embodiment, the present invention is an organ, organ tissue or cell derived from the transgenic animal (e.g., porcine animal) disclosed herein.

In certain embodies, the organ is a lung. In certain embodiments, the tissue is lung tissue.

In selected embodiments, the organ is a kidney, heart, or liver. In other embodiments, the tissue is derived from liver (including isolated hepatocytes, or liver derived stem cells), from fat (including adipocytes or mesenchymal stem cells), from cardiac tissue including heart valves, pericardium, cardiac vessels or other derivatives (viable or non-viable), derived from skin, dermis or connective tissue, bone, bone derivatives or other orthopedic tissue, dura, blood vessels, or any other tissues, including from other organs, viable or non-viable.

The lung is a large, spongy organ optimized in mammals for gas exchange between blood and the air. In mammals and more complex life forms, two lungs are located near the backbone on either side of the heart. Each lung is made up of sections called lobes. Humans have three lobes in the right lung and two lobes in the left lung. Pigs have two lobes in the left lung and four lobes in the right lung. The lungs of mammals including those of humans, are honeycombed with epithelium, having a much larger surface area in total than the outer surface area of the lung itself. Porcine lungs have cellular lineages and composition that are comparable with human lungs.

The donor animal (e.g., porcine animal) of the present invention may be at any stage of development including, but not limited to, fetal, neonatal, young and adult. In some embodiments, organs or tissue are isolated from adult porcine transgenic animals. In alternate embodiments, the organ or tissue is isolated from fetal or neonatal transgenic animals (see e.g. Mandel (1999) J. Mol. Med. 77:155-60; Cardona, et al. (2006) Nat. Med. 12:304-6).

In exemplary embodiments, the donor animal may be under the age of 10, 9, 8, 7, 6, 5, 4, 3, 2, or 1 year(s). In one embodiment, the organ or tissue or tissue isolated from transgenic animal under the age of 6 years. In another embodiment, the organ or tissue is isolated from transgenic animal under the age of 3 years. The donor animal may be any age between 0 to 2 years, 2 to 4 years, 4 to 6 years, 6 to 8 years, or 8 to 10 years. In another embodiment, the organ or tissue is isolated from the fetal or neonatal stage In another embodiment, the organ or tissue is isolated from newborn to 6 months old transgenic pigs. In one embodiment, the organ or tissue is isolated from fetal to 2 year old transgenic animals. In a particular embodiment, the organ or tissue is isolated from 6 months old to 2 year old transgenic animals, and in a more particular embodiment, 7 months old to 1 year old transgenic animals. In one embodiment, the organs or tissues are isolated from 2-3 year old transgenic animal. In another embodiment, the organs or tissues are isolated from a transgenic animal that is matched in weight (not age) to provide organs or tissues of optimal size to the human transplant recipient, such that said pig organs or tissues are procured from donor animals customized for age, weight, and/or sex of the recipient/patient.

In certain embodiments, the donor transgenic lung(s) or tissue is surgically removed. Following surgical removal, the donor lung or tissue may be further processed or evaluated prior to transplantation.

"Xenoluni Pre-Conditioning" or Immune Conditioning

The long term survival of transplanted lungs are inferior to other organs, including hearts, kidney and liver. This inferior outcomes after lung transplant can be associated with a multitude of factors of which ischemia and reperfusion (IRI) injury, an inflammatory insult, initiated by ischemia mainly resulting from the donor being brain death after cardiac arrest, but include factors such as duration of organ retrieval during procurement, cold organ preservation, etc. Subsequently, IRI is exacerbated upon re-oxygenation of the lung tissue when blood flow is restored. Further insult to injury is that in comparison to other transplanted organs, the newly transplanted lungs continue to be exposed to environmental antigens after surgery and can partially be blamed for the decrease in survival rates. The near continuous exposure of the transplanted lung to environmental antigens has been proposed to create a unique situation where immune recognition pathways are activated, leading to rejection, and perhaps increased sensitivity to the consequences of inflammation, tissue damage and IRI and should be address to increase the survival rates. In an exemplary embodiment strategies for lung transplant tolerance induction are taken in consideration, a non-limiting example of recondition lungs via ex vivo lung perfusion, more specifically perfusion of the lungs with a STEEN solution supplemented with AdhIL-10 as a gene therapy to enhance long term survival of transplanted lungs. In one further embodiment, the tolerance can be induced via "mixed chimerism", bone marrow collected from the sternum, thymus, with or without CD47.

Ex Vivo Lung Perfusion

Ex vivo lung perfusion (EVLP) may be used to evaluate and recondition lungs following removal from the donor, such that the function of marginal/injured lungs can be improved and significant, persistent dysfunction can be identified prior to recipient implantation.

Lungs placed in an ex vivo circuit (Toronto XVIVO™ System) and perfused normothermically with Steen Solution™ for 2 to 4 h for physiologic re-assessment. With respect to the decision for lung utilization, lungs with a delta pO2 (pO2 Pulmonary vein pO2-pulmonary artery pO2) during ex vivo perfusion assessment >400 mmHg, are considered transplantable. Lungs are excluded for transplantation: if pO2<400 mmHg or if they demonstrate >10% deterioration in any of the following functional parameters: pulmonary vascular resistance (PVR), dynamic compliance or airway pressures. Lungs are also excluded for transplantation if they are deemed unsuitable based on the clinical judgment of the lung transplant surgeon.

In one embodiment, lungs are perfused with a hyperoncotic, acellular serum that dehydrates edematous lungs by drawing fluid from extravascular compartments such that gas exchange can be improved and lungs initially judged to be unsuitable for transplant can be rendered usable. Additionally, anti-inflammatory cytokines may be infused into the lungs to promote injury repair, and vector-mediated transfer of interleukin (IL)-10 utilized to decrease proinflammatory cytokine production, promote recovery of intercellular alveolar epithelial tight junctions, improve oxygenation, and decrease vascular resistance. Antibiotics can also be infused to suppress/eliminate infection.

Ex Vivo Lung Perfusion Base Gene Therapy—Interleukin-10 (IL-10)

Additionally, anti-inflammatory cytokines may be infused into the lungs to promote injury repair, and vector-mediated transfer of interleukin (IL)-10 utilized to decrease proinflammatory cytokine production, promote recovery of intercellular alveolar epithelial tight junctions, improve oxygenation, and decrease vascular resistance.

In one embodiment the ex vivo lung perfusion maybe utilized as a delivery mechanism to deliver IL-10, that is consistently expressed from an adeno-IL10 vector, to the xenolung. The embodiment facilitates the transplantation of the lung from the transgenic animal, by providing excellent control of early inflammation under lower exposure of conventional immunosuppression. In addition, anti-IL6r (antibiotic) can be given at lung transplant with conventional immunosuppression, and repeated after period of time (~4 months) with the tolerance conditioning regimen as a method to allow for the successful withdrawal of conventional immunosuppression.

Tolerance

XenoLung and tolerance: Induction of mixed chimerism uses an intensive, non-myeloablative conditioning regimen during the 5-7 days prior to transplantation; attempts to shorten this to accommodate needs in the deceased donor setting were excessively toxic and poorly tolerated. Although not yet demonstrated clinically, "delayed" tolerance induction by depleting CD8+ memory T cells, then timing the bone marrow transplant to minimize pro-inflammatory cytokines, has been used in non-human primate kidney transplant experiments F. Method of Treatment The invention described herein encompasses methods of xenotransplantation of the organ, organ fragment, tissue or cell described herein. In an exemplary embodiment, the methods include, but are not limited to, administering an organ, organ fragment, tissue or cell a donor animal described herein to a subject. The donor animal may be a porcine. The subject or host may be a primate, for example, a non-human primate (NHP) including, but not limited to, a baboon. The host may be a human and in particular, a human suffering from a disease or disorder that could be impacted therapeutically by the transplant.

In an exemplary embodiment, the methods include, but are not limited to, administering a lung(s) or lung tissue from a donor animal described herein to a host. The donor animal may be a porcine. The host may be a primate, for example, a non-human primate (NHP) including, but not limited to, a baboon. The host may be a human and in particular, a human suffering from a lung disease or disorder.

Advantageously, the transgenic lungs and lung tissues provided by the present invention have improved functionality relative to xenotransplants known in the art. In one embodiment, the transgenic lungs have improved survival in an ex vivo model of pig-to-human xenotransplantation. In a particular embodiment, the transgenic lungs survive at least about 90, at least about 120, or at least about 150, at least about 180, at least about 210, at least about 240, at least about 270, at least about 300, at least about 330, at least about 360 minutes or more. In another particular embodiment, the transgenic lungs survive at least about two times, at least about four times, at least about eight times, at least about ten times longer or at least about 20 times longer than unmodified porcine lungs.

In another embodiment, the transgenic lungs have improved function and survivability in a life supporting in-vivo model. In a particular embodiment, the lung(s) or lung tissue provided herein supports life in a baboon in a life-supporting model for at least about 10 hours, at least about 20 hours, at least about 30 hours, or about 30 hours or more. In another particular embodiment, the transgenic lungs survive at least about two times, at least about four times, at least about eight times, at least about ten times longer or at least about 20 times longer than unmodified porcine lungs.

Another method of the invention is a method of xenotransplantation wherein the transgenic lung(s) or lung tissue provided herein is transplanted into a primate and, the transplanted lung or tissue survives at least about one, at least about two, at least about three, at least about four, at least about five, at least about six, at least about seven, at least about eight, at least about nine, at least about ten, at least about eleven or at least about twelve weeks or more.

A further method of the invention is a method of xenotransplantation wherein the transgenic lung(s) or lung tissue provided herein is transplanted into a primate and, the transplanted lung or tissue survives at least about one, at least about two, at least about three, at least about four, at least about five, at least about six, at least about seven, at least about eight, at least about nine, at least about ten, at least about eleven or at least about twelve months or more.

An additional method of the invention is a method of xenotransplantation wherein the transgenic lung(s) or lung tissue provided herein is transplanted into a primate and, the transplanted lung or tissue survives for a period of time as described above. In one embodiment, a life-supporting model of lung xenotransplantation is used to assess lung function. In one embodiment, the life supporting model includes removing one lung from the primate and transplanting a single lung from the porcine donor of the present invention into the primate recipient. In another embodiment, life supporting model includes removing both lungs from the primate and transplanting both lungs from the porcine donor of the present invention into the primate recipient. In a further embodiment, both lungs and the heart can be removed from the primate and replaced with the porcine lungs and heart of the present invention. In embodiments of the present invention, duration of life-supporting lung function can be assessed in the primate.

To assess duration of life-supporting lung function, genetically modified porcine lungs of the present invention can be harvested from the pig. The heart-lung block can be excised, and either one lung, two lungs or two lungs and the heart can be prepared for transplant into the primate. Primate recipients can be sedated and maintained under general anesthesia. The lung, lungs or heart and lungs can then be removed from primate using methods known in the art (see, for example, Nguyen et al The Journal of Thoracic and Cardiovascular Surgery May 2007; 133: 1354-63 and Kubicki et al International Journal of Surgery 2015: 1-8), transplanted into the primate and then the primate can be reperfused. Before and after graft reperfusion, blood and tissue biopsy specimens can be collected serially at predetermined time points for in vitro analysis. Vascular flow probes (Transonic Systems Inc, Ithaca, N.Y.) on the aorta and left pulmonary artery can continuously measure cardiac output and flow to the transplanted organs, respectively. In models in which only one lung is transplanted and the second lung remains a native primate lung, blood flow to the native lung can be progressively occluded to assess the capacity of the transplanted lung to support life. Graft survival can be defined as duration of life-supporting lung function. For long-term survival experiments, flow probes placed on the aorta and one pulmonary artery allow monitoring of blood flow through the pulmonary transplant. The International Society for Heart and Lung Transplantation has recommended consistent achievement of three months of life-supporting function in a model such as this in order to consider a human trial (Kubicki et al International Journal of Surgery 2015: 1-8).

One method of the invention is a method of xenotransplantation wherein the transgenic lung or lung tissue provided herein are transplanted into a primate and, after the transplant, the primate requires reduced or no immunosuppressive therapy. Reduced or no immunosuppressive therapy includes, but is not limited to, a reduction (or complete elimination of) in dose of the immunosuppressive drug(s)/agent(s) compared to that required by other methods; a reduction (or complete elimination of) in the number of types of immunosuppressive drug(s)/agent(s) compared to that required by other methods; a reduction (or complete elimination of) in the duration of immunosuppression treatment compared to that required by other methods; and/or a reduction (or complete elimination of) in maintenance immunosuppression compared to that required by other methods.

The methods of the invention also include methods of treating or preventing lung disease wherein the transgenic lung(s) or lung tissue provided herein is transplanted into a primate and, after the transplant, the primate has improved lung function. The transplanted primate may have improved lung function when compared to the level prior to transplant or when compared to the level achieved using other methods.

The methods of the invention also include methods of treating or preventing disease after the transplantation of transgenic lung(s) or lung tissue, there are not numerous, or serious life-threatening, complications associated with the transplant procedure, immunosuppressive regimen, and/or tolerance-inducing regimen.

In some embodiments, the method reduces the need for administration of anti-inflammatories to the host. In other embodiments, the method reduces the need for administration of anticoagulant to the host. In certain embodiments, the method reduces the need for administration of immunosuppressive agents to the host. In some embodiments, the host is administered an anti-inflammatory agent for less than thirty days, or less than 20 days, or less than 10 days, or less than 5 days, or less than 4 days, or less than 3 days, or less than 2 days, or less than one day after administration of the organ (e.g., lung), tissue or cell. In some embodiments, the host is administered an anti-coagulant agent for less than thirty days, or less than 20 days, or less than 10 days, or less than 5 days, or less than 4 days, or less than 3 days, or less than 2 days, or less than one day after administration of the organ (e.g., lung), tissue or cell. In some embodiments, the host is administered an immunosuppressive agent for less than thirty days, or less than 20 days, or less than 10 days, or less than 5 days, or less than 4 days, or less than 3 days, or less than 2 days, or less than one day after administration of the organ (e.g., lung), tissue or cell.

The recipient (host) may be partially or fully immunosuppressed or not at all at the time of transplant. Immunosuppressive agents/drugs that may be used before, during and/or after the time of transplant are any known to one of skill in the art and include, but are not limited to, MMF (mycophenolate mofetil (Cellcept)), ATG (anti-thymocyte globulin), anti-CD154 (CD40L), anti-CD20 antibody, anti-CD40 (2C10R4 antibody therapy). See Mohiuddin M M. et al., Apr. 5; 7:11138. [2016].
alemtuzumab (Campath), CTLA4-Ig (Abatacept/Orencia), belatacept (LEA29Y), sirolimus (Rapimune), tacrolimus (Prograf), daclizumab (Zenapax), basiliximab (Simulect), infliximab (Remicade), cyclosporin, deoxyspergualin, soluble complement receptor 1, cobra venom, methylprednisolone, FTY720, everolimus, anti-CD154-Ab, leflunomide, anti-IL-2R-Ab, rapamycin, and human anti-CD154 monoclonal antibody. One or more than one immunosuppressive agents/drugs may be used together or sequentially. One or more than one immunosuppressive agents/drugs may be used for induction therapy or for maintenance therapy. The same or different drugs may be used during the induction and maintenance stages. In one embodiment, daclizumab (Zenapax) is used for induction therapy and tacrolimus (Prograf) and sirolimus (Rapimune) is used for maintenance therapy. In another embodiment, daclizumab (Zenapax) is used for induction therapy and low dose tacrolimus (Prograf) and low dose sirolimus (Rapimune) is used for maintenance therapy. In one embodiment, alemtuzumab (Campath) is used for induction therapy. See Teuteberg et al., Am J Transplantation, 10(2):382-388. 2010; van der Windt et al., 2009, Am. J. Transplantation 9(12): 2716-2726. 2009; Shapiro, The Scientist, 20(5):43. 2006; Shapiro et al., N Engl J. Med. 355:1318-1330. 2006 Immunosuppression may also be achieved using non-drug regimens including, but not limited to, whole body irradiation, thymic irradiation, and full and/or partial splenectomy, "mixed chimerism", bone marrow collected from the sternum, thymus (Sachs, 2014). These techniques may also be used in combination with one or more immunosuppressive drug/agent.

A person is in need of a lung transplant when their lungs can no longer perform its vital function of exchanging oxygen and carbon dioxide. Lung transplant candidates have end-stage lung disease and are expected to live less than two years. They often require continuous oxygen and are extremely fatigued from the lack of oxygen. Their lungs are too diseased to be managed medically, and no other kind of surgery will help them.

Single Lung Transplant

If the recipient is having a single lung transplant, he/she will have a thoracotomy incision either on their right or their left side, depending on which lung is being replaced. After the donor lung arrives in the operating room, the surgeon will remove the diseased lung. The recipient will be ventilated using the other lung. If the remaining lung is not able to exchange enough oxygen, the surgeon may place the recipient on cardiopulmonary bypass. Their blood will be filtered through a machine outside the body which will put oxygen into their blood and remove carbon dioxide.

Three connections will be used to attach the new lung. These connections are called anastomoses. First, the main bronchus from the donor lung is attached to the recipient's bronchus. Then the blood vessels are attached-first the pulmonary artery, and then the pulmonary veins. Finally, the incision is closed and the recipient will be taken to the intensive care unit, where he/she will be asleep for approximately 12 to 24 hours.

Bi-Lateral or Double Lung Transplant

If both lungs are transplanted (a bilateral transplant), the surgeon will make an incision below each breast, called an anterior thoracotomy, or an incision that goes from the right side to the left side at the base of the breasts. This is called a transverse sternotomy incision. In a bilateral lung transplant, each lung is replaced separately. The surgeon begins by removing the lung with the poorest function. The recipient will be ventilated using their remaining lung unless partial cardiopulmonary bypass is needed. Once the first lung is removed, a donor lung will be attached using three connections. The donor bronchus is attached to the recipient's main bronchus, then the blood vessels are attached—first the pulmonary artery, then the pulmonary veins. The recipient's second diseased lung is removed and the other new lung is attached in the same way. Once the second lung is completely connected, blood flow is restored.

The transgenic lung(s) lung tissue or heart-lung transplantation may be transplanted using any means known in the art.

Sufficient time to allow for engraftment (for example, 1 week, 3 weeks, and the like) is provided and successful engraftment is determined using any technique known to one skilled in the art. These techniques may include, but are not limited to, assessment of donor C-peptide levels, histological studies, intravenous glucose tolerance testing, exogenous insulin requirement testing, arginine stimulation testing, glucagon stimulation testing, testing of IEQ/kg (pancreatic islet equivalents/kg) requirements, testing for persistence of normoglycemia in recipient, testing of immunosuppression requirements, and testing for functionality of transplanted islets (See Rood et al., Cell Transplantation, 15:89-104. 2006; Rood et al., Transplantation, 83:202-210. 2007; Dufrane and Gianello, Transplantation, 86:753-760. 2008; van der Windt et al., 2009, Am. J. Transplantation, 9(12):2716-2726. 2009).

One or more techniques may be used to determine if engraftment is successful. Successful engraftment may refer to relative to no treatment, or in some embodiments, relative to other approaches for transplantation (i.e., engraftment is more successful than when using other methods/tissues for transplantation). In some cases, successful engraftment is determined by assessment of donor C-peptide levels including life supporting function with added immunosuppression.

In one embodiment, the present invention provides a method of treating a lung disease or disorder in a subject in need thereof comprising implanting a lung, or a portion thereof, derived from a transgenic pig of the present invention into the subject.

The lung disease may be an advanced lung disease. In one embodiment, the advanced lung disease is associated with primary pulmonary hypertension (PAH), chronic obstructive pulmonary disease (COPD), interstitial lung disease (ILD), sarcoidosis, bronchiectasis, idiopathic pulmonary fibrosis (IPD), cystic fibrosis (CF), alpha1-antitrypsin deficiency disease.

As would be understood by one of skill in the art, primary pulmonary hypertension (PAH) refers to high blood pressure in the arteries of the lung.

As would be understood by one of skill in the art, cystic fibrosis refers to is a genetic disease that is recessively inherited, meaning both parents need to have the defective gene. Approximately 30,000 Americans have CF, and about 12 million carry the gene but are not affected by it. CF patients often have respiratory problems including bronchitis, bronchiectasis, pneumonia, sinusitis (inflammation of the sinuses), nasal polyps (growths inside the nose), or pneumothorax (collapsed lung). Symptoms of CF include frequent wheezing or pneumonia, chronic cough with thick mucus, persistent diarrhea, salty-tasting skin, and poor growth.

As would be understood by one of skill in the art, chronic obstructive pulmonary disease (COPD) refers to can be caused by asthma, chronic bronchitis or emphysema. Over time, individuals with COPD slowly lose their ability to breathe. Symptoms of COPD range from chronic cough and sputum production to severe, disabling shortness of breath As would be understood by one of skill in the art, alpha1-antitrypsin disease/alpha-1 antitrypsin deficiency is a hereditary condition in which a lack of alpha-1 antitrypsin—a protein that protects the lungs—results in early-onset lung disease. Smoking greatly increases this risk. The first symptoms of alpha-1 related emphysema often appear between ages 20 and 40 and include shortness of breath following activity, decreased exercise capacity, and wheezing.

As would be understood by one of skill in the art, interstitial lung disease (ILD), is a general term that includes a variety of chronic lung disorders such as idiopathic pulmonary fibrosis, sarcoidosis, eosinophilic granuloma, Goodpasture's syndrome, idiopathic pulmonary hemosiderosis and Wegener's granulomatosis. When a person has ILD, the lung is affected in four ways: 1) The lung tissue becomes damaged, 2) the walls of the air sacs in the lung become inflamed, 3) scarring begins in the interstitium (tissue between the air sacs), and 4) the lung becomes stiff.

As would be understood by one of skill in the art, sarcoidosis refers to a disease involving abnormal collections of inflammatory cells (granulomas) that can form as nodules in multiple organs. The granulomas are most often located in the lungs or its associated lymph nodes.

As would be understood by one of skill in the art, bronchiectasis refers to the irreversible widening of the airways. As airways widen, they become less rigid and more prone to collapse. It also becomes more difficult to clear away secretions. Bronchiectasis can be present at birth, or it can develop later as a result of injury or other diseases (most often cystic fibrosis). It can occur at any age but most often begins in childhood. Symptoms of bronchiectasis include coughing, fever, weakness, weight loss, and fatigue In one embodiment, the method further comprises administering to the subject one or more therapeutic agents.

In a particular embodiment, the one or more therapeutic agents are selected from anti-rejection agents, anti-inflammatory agents, immunosuppressive agents, immunomodulatory agents, anti-microbial agents, anti-viral agents and combinations thereof.

The transplant may involve a single lung or both lungs (bilateral).

The transplant can also involve cardiopulmonary transplantation or heart-lung transplantation that is the simultaneous surgical replacement of the heart and lungs in patients with end-stage cardiac and pulmonary disease. This procedure remains a viable therapeutic alternative for patients in specific disease states. Causes of end-stage cardiopulmonary failure that necessitate cardiopulmonary transplantation range from congenital cardiac disease to idiopathic causes and include the following: irreparable congenital cardiac anomalies with pulmonary hypertension (Eisenmenger complex), primary pulmonary hypertension with irreversible right-heart failure; sarcoidosis involving only the heart and lungs.

EXAMPLES

Example 1: Vector Construction and Generation of Pigs Using a Bicistronic Vector Vector Construction Multiple bicistronic units were synthesized consisting of two (2) transgenes linked by 2A peptide sequences that share a single promoter. Two forms of 2A sequences, P2A (66 bp) and T2A (55 bp) were utilized and linked a large number of two transgene units to allow co-expression of both genes from one promoter. Promoters were either the constitutive CAG promoter (CMV enhancer, chicken actin promoter, rabbit b-globin intron), the endothelial-specific porcine ICAM-2 promoter or a combination of the Tie2 endothelial-specific enhancer with the CAG promoter. Pairs of human transgenes were constructed (connected by the 2A sequence) including thrombomodulin (TBM), CD39, EPCR, DAF, A20, CD47, CIITA, HO1, TFPI, and in certain bicistronic vectors also included porcine CTLA4-Ig.

A multicistronic vector was engineered with cloning sites behind a) porcine ICAM-2 enhancer/promoter and b) the constitutive CAG promoter. See FIG. 1. This vector permitted insertion of two bicistronic units with provision of insulation between and flanking these units. Several multicistronic vectors (MCV's) were constructed in which each bicistronic was regulated by its own promoter, drawing from a repertoire of mechanistically relevant genes paired and linked by 2A peptide sequences.

Generation of Pigs Using a Bicistronic Vector

Genotype: GTKO.CD46.cagEPCR.DAF.cagTFPI.CD47.

Pigs with bicistronic vectors (under control of the CAG promoter) were produced. In certain lines, two bicistronics were incorporated into alpha Gal knockout (GTKO) pig fibroblasts (by transfection and random integration) that were also transgenic for the human CD46 complement inhibitor gene (GTKO.CD46). Such multigene fibroblasts were used for somatic cell nuclear transfer (SCNT) to produce cloned transgenic pigs. A single line of transgenic pigs that robustly expressed all 4 MCV genes as two bicistronics under the control of the CAG promoter (CAG-EPCR.DAF and CAG-TFPI.CD47) was been used to produce several pigs for use in organ transplant experiments in non-human primates (baboons).

Multi-transgenic pigs with the genotype "CAG-EPCR.DAF and CAG-TFPI.CD4T" have demonstrated efficacy in kidney, heart, and lung transplants. M multiple pigs provided >30 h life support in the in vivo lung treatment model.

Baboons that received lungs from pigs with the genotype "GTKO.hCD46.hDAF.hEPCR.hCD47.hTFPF" exhibited only modest fluid retention (edema) and inotrope requirements, in contrast to the progressive xenograft injury and physiologic perturbations (ascites, escalating volume and inotrope requirements, native (baboon) lung edema) frequently seen in past experiments with pigs having three genetic modifications (GTKO.CD46.TBM). Pig lungs from these longest surviving experiments appeared macro- and microscopically grossly normal without signs of rejection.

In other pig organ to baboon transplant studies, this 6GE genotype extended survival time of heart transplants (>6 mos survival in heterotopic Tx), and orthotopic kidney Tx (>8 months) in two successive transplants for each organ model (heart and kidney). In comparison, for the life supporting orthotopic kidney Tx model, only <3 months survival was achieved when using a kidney from a three-gene GTKO.CD46.TBM pig (3GE).

Figure 2:
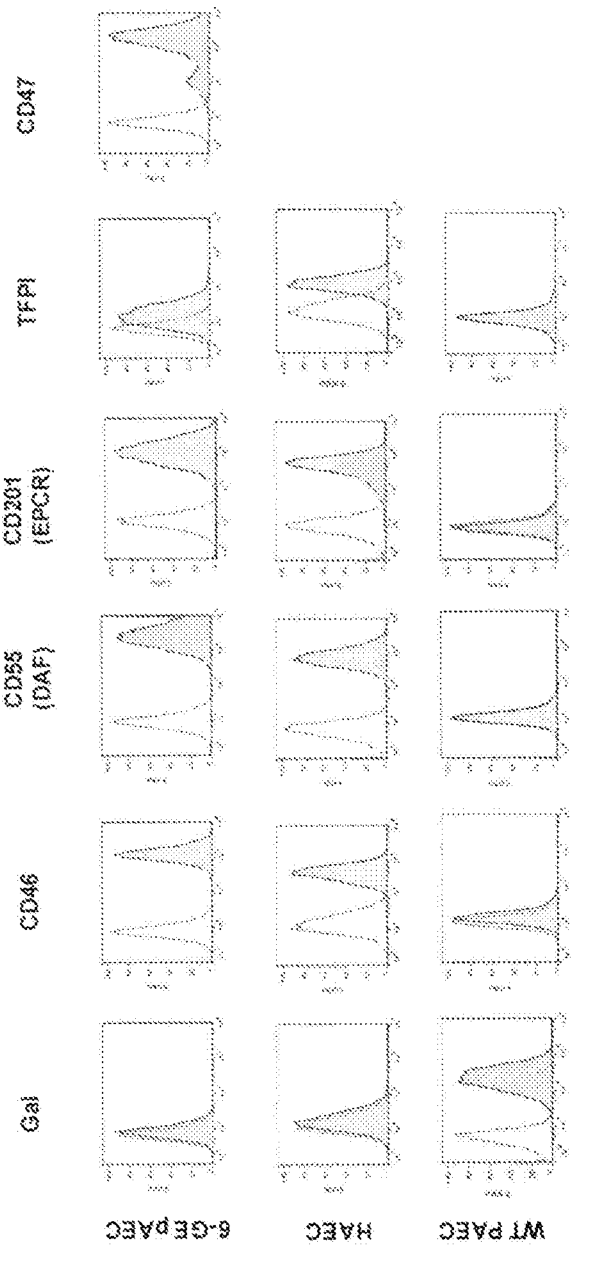
FIG. 2 depicts gene expression in 6GE pigs (GTKO.CD46.TBM.CD39.EPCR.DAF) by flow cytometry demonstrating lack of alpha-Gal expression, and robust expression of five (5) human transgenes including CD46, CD55(DAF), EPCR, TFPI, and CD47.
Figure 3:
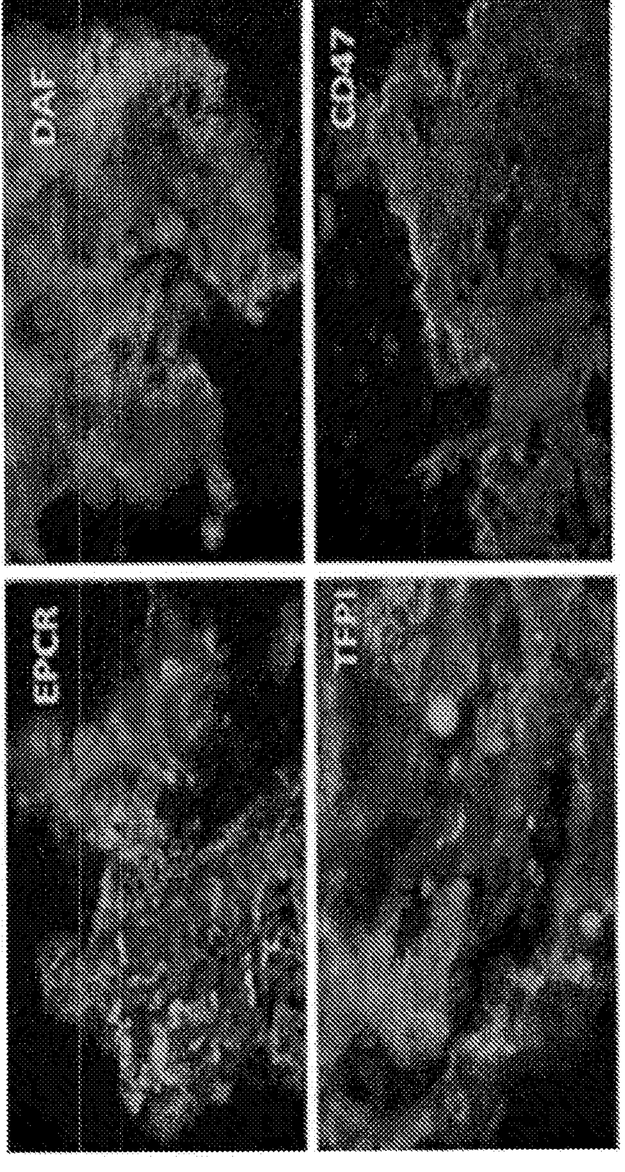
FIG. 3 depicts immunohistochemistry staining of lung sections using fluorescently labeled antibodies against EPCR, DAF, TFPI, and CD47 in 6GE pigs (GTKO.CD46.TBM.CD39.EPCR.DAF)

This six-gene line (6GE) had strong expression of all MCV transgenes, by both flow cytometry of aortic endothelial cells (see FIG. 2), or by immunohistochemistry (FIG. 3) and staining separately using florescent antibodies specific for each human transgenic protein. Viability of this line to maturity has recently been demonstrated with a mature healthy 1 year old boar that is currently being bred to GTKO.CD46 females.

This line is bred to three GE pigs that are GTKO.CD46.TBM or GTKO.CD46.CIITA, or GTKO.CD46.CMAH-KO to produce herds of seven GE pigs (7GE) from multiple combinations, and males and females of such genotypes for further line expansion.

Example 2: Construction of Multicistronic Vectors for the Production of Genetically Modified Pigs Multi-cistronic "2A" vectors (MCVs) were used for production of 6-GE pigs, employing four-gene vectors (two bicistronics under control of two promoters in each MCV) transfected into well-characterized GTKO.hCD46 cells, which were then used for somatic cell nuclear transfer. Genotype was determined by Southern analysis. Gene expression was monitored by flow cytometry of PBMCs and endothelial cells, and in cells and organs by immunohistochemistry, Q-PCR (quantitative polymerase chain reaction) and Western blot analysis. Bioactivity assays specific to the transgenes were developed to quantitate and characterize complement inhibition, platelet aggregation, activated protein C formation, ATPase activity, Factor Xa cleavage, mixed lymphocyte reaction (MLR) and apoptosis. Pigs with expected genotype and robust expression of all transgenes were identified in these assays and used in both ex vivo and in vivo models of xenotransplantation.

Figure 4A:
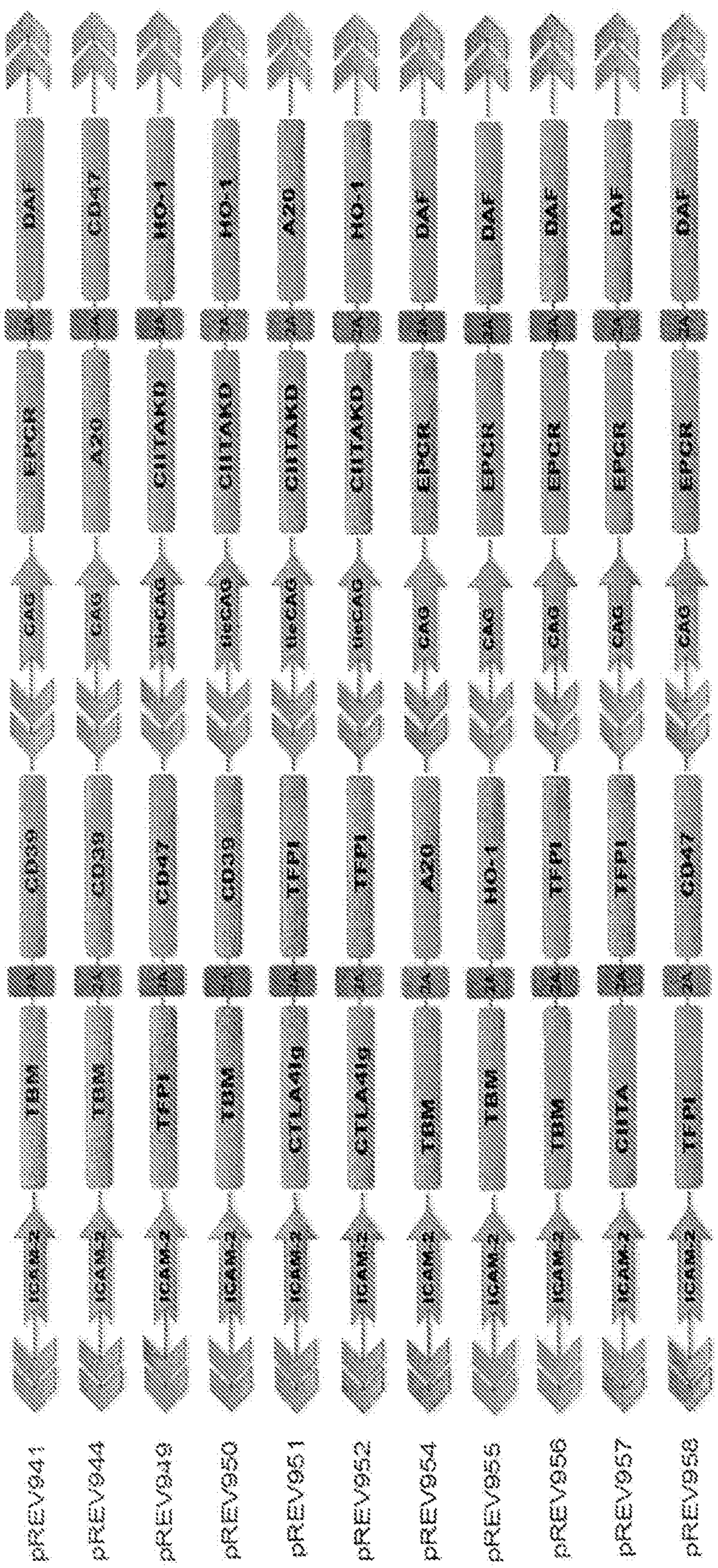
FIGS. 4A and B depict multicistronic vectors (MCV) designed and produced according to the present invention. Pigs were produced with 6 genetic modifications including expression cassettes for the complement regulatory genes hCD46 and CD55, combined with endothelial-specific or ubiquitous expression of anti-coagulant genes thrombomodulin (TBM), endothelial protein C receptor (EPCR), CD39, and tissue factor pathway inhibitor (TFPI)], immunosuppressive genes porcine cytotoxic T lymphocyte-associated protein-4 (pCTLA4Ig), class II major histocompatibility complex dominant negative (CIITA-DN), and/or anti-inflammation transgenes heme oxygenase-1 (HO1), A20, CD47
Figure 4B:
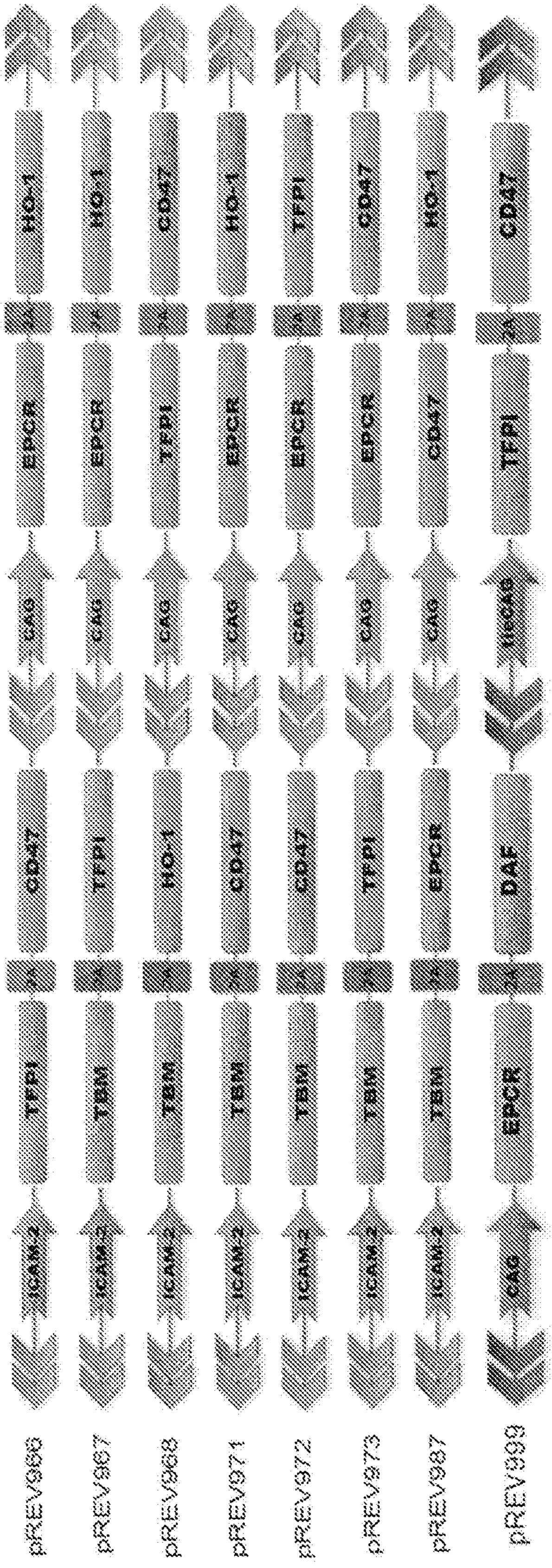
Figure 5:
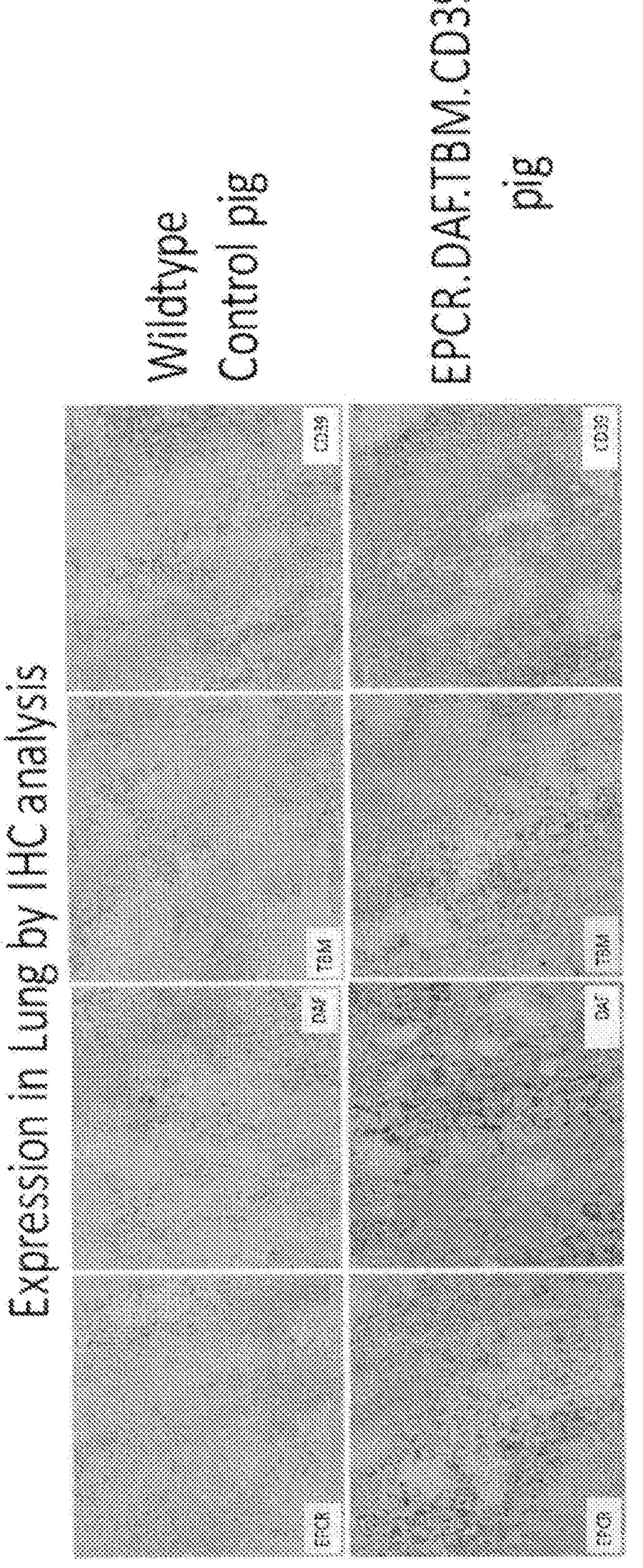
FIG. 5 depicts expression analysis of pREV941 transgenes in lung.

Types of Multicistronic Vectors:

Eighteen multi-cistronic vectors were generated and used to produce pigs with different combinations of these bioactive transgenes (see FIG. 4). In most cases, one pair of genes was expressed under the control of the endo-specific pICAM-2 promoter, and in the same vector, two other genes (in the 2$^{nd}$ bi-cistronic) were expressed via the constitutive CAG promoter. However, in MCV vector pREV999, both promoters utilized were CAG. The bicistrons were separated and flanked by insulator sequences (represented by double arrows in FIG. 4) to minimize any effects related to genomic integration site, and also to limit cross-talk between the regulatory sequences present in each bicistron.

FIG. 4 shows expression cassettes used for the production of pigs with 6 genetic modifications including GTKO, the complement regulatory genes hCD46 or CD55, combined with endothelial-specific or ubiquitous expression of anti-coagulant genes thrombomodulin (TBM), endothelial protein C receptor (EPCR), CD39, and tissue factor pathway inhibitor (TFPI), immunosuppressive genes porcine cytotoxic T lymphocyte-associated protein-4 (pCTLA4Ig), class II major histocompatibility complex dominant negative (CIITA-DN), and/or anti-inflammation transgenes heme oxygenase-1 (HO1), A20, CD47

Example 3: Production of Porcine Animals with Six Genetic Modifications (6GE)

Linear MCV 4 gene fragments (see, for example, FIG. 4) were transfected into porcine fetal fibroblasts having GTKO (alpha-1,3-galactosyltransferase knockout) or GTKO.CD46 (alpha-1,3-galactosyltransferase knockout and ubiquitous expression of CD46) platform genetics. Transfected cells were selected for both genes expressed behind the CAG promoter by fluorescence-activated cell sorting (FACS) and these sorted cells were used as nuclear donors for somatic cell nuclear transfer (SCNT or cloning). Fused embryos were transferred to multiple recipient gilts (8-10 gilts/MCV) and pregnancies were monitored until farrowing.

Pigs expressing these MCV elements were produced from several of the gene combinations. Four of the 4-gene MCV combinations that provided robust expression in viable pigs included:

pREV941: EPCR-CD55-TBM-CD39
pREV971: EPCR-HO-1-TBM-CD47
pREV967: EPCR-HO-1-TBM-TFPI
pREV958: EPCR-CD55-TFPI-CD47

Depending on the vector configuration, expression of TBM, TFPI, CD39 and CD47, HO-1 was driven by an endothelial-specific promoter, porcine Icam-2. Expression of EPCR, DAF, and HO-1 was driven by a constitutive CAG promoter.

The genetics of these 6GE pigs was:

pREV941: GTKO.CD46.EPCR.CD55.TBM.CD39
pREV971: GTKO.CD46.EPCR.HO-1.TBM.CD47
pREV967: GTKO.CD46.EPCR.HO-1.TBM.TFPI
pREV958: GTKO.CD46.EPCR.CD55.TFPI.CD47

Example 4: Survival and Function of Organs from 6GE Pigs pREV941: GTKO.CD46.EPCR.CD55.TBM.CD39. Several founder pigs of this 6-gene genotype were produced and used for lung, heart, and kidney transplant. One founder provided twelve (12) hours of life support in the pig to non-human primate (NHP) in vivo lung model. A second founder provided seven (7) hours of life support in the in vivo lung Tx model. A third founder provided a heart that lasted greater than five (5) months in a non-human primate. One of the founders with excellent expression of all six (6) genes (see FIG. 4) was re-cloned and several of the progeny used as organ donors for transplants (Tx) in vivo in baboon models, including a heterotopic heart transplant that lasted 10 months. This line was used for in vivo lung transplant, with seven (7) hours of life support function.

pREV971: GTKO.CD46.EPCR.HO-1.TBM.CD47. Three founder pigs as well as three re-cloned pigs were produced with this genotype. Additional pigs with this genotype were in utero. One of the founders with expression of all 6 genes provided life support of approximately 24 hours in the in vivo model of lung transplant (Tx). There was no edema or thrombus reported. Re-clones of this high expressing line were produced by SCNT from kidney cells procured from the founder animal. Transplantation studies are conducted to test immunosuppressant therapies pre-Tx and during the course of the transplant. Additional treatments are used in conjunction with immunosuppressive drugs, such as administration of human alpha-1-antitrypsin (hAAT) to reduce inflammation and chlodronate liposomes to deplete the donor lung of resident macrophages prior to transplant into the baboon model.

pREV967: GTKO.CD46.EPCR.HO-1.TBM.TFPI. Eight viable founder pigs were produced. Two additional pregnancies were established with re-clones of one of these pigs.

pREV958: GTKO.CD46.EPCR.CD55.TFPI.CD47. A 4-gene MCV version of the genotype "pREV958" (see FIG. 4), which utilized the pICAM-2 promoter to drive expression of TFPI+CD47 and the CAG promoter to drive expression of EPCR+DAF was constructed and utilized to produce a similar genotype but as a 4-gene MCV with all 4 genes integrated at one locus. Two recipient baboons, receiving porcine lungs derived from pigs with the pREV958 genotype, were recovered and extubated after the transplantation and followed up demonstrating survival for up to eight (8) days. This is the longest recorded survival of a xenolung in vivo in non-human primates.

Example 5: Targeted Insertion of an Oligonucleotide "Landing Pad" into the Gal Locus A synthesized DNA fragment intended for CRISPR-enhanced targeted integration into the alpha Gal locus was engineered for targeting of the $Neo^r$ selectable marker gene imbedded at the modified native alpha Gal locus within this line of GTKO.CD46 transgenic pigs (see Dai et. al. 2002. Nature Biotechnology). This "landing pad" fragment was 100 bp, and contained two sites for recombinase/integrase-mediated site-specific recombination, namely phi-C31 and BxbI attP sites, and was flanked by 50 bp homology arms specific for targeted integration at the modified alpha Gal. The multiple transgenes harbored within a particular MCV (flanked by such att sites), and subsequently integrated into the alpha Gal locus, co-segregate during breeding not only with the other transgenes within the MCV, but also with the alpha Gal knockout genotype.

This landing pad oligonucleotide was transfected into GTKO.CD46 fibroblasts, in combination with a CRISPR/Cas9 DNA vector designed to introduce a double stranded break within the modified Gal locus.

Two GTKO.CD46 fetal fibroblast clones with CRISPR-assisted targeted integration of this recombinase/integrase "landing pad" fragment at alpha Gal were identified by long range PCR analysis, and confirmed to harbor bi-allelic targeted integrations. Nuclear transfer into six recipients was done with one of these clones for fetus collection and confirmation of precise integration of this ~200 bp fragment.

Two fetuses derived from one pregnancy were produced using a cell line in which this small landing pad fragment was inserted into the Gal locus. DNA was isolated from both fetuses and long range PCR, which produced an amplimer representing the inserted fragment and flanking sequence on both sides, confirmed that both fetuses carried bi-allelic integration of the landing pad (homozygous knockin of the phiC31 and BxbI attP sites) at the Gal locus.

Example 6: GTKO.CD46hom+TBM.CD39.EPCR.DAF with Gal Homology Arms (941HDR)

Figure 7:
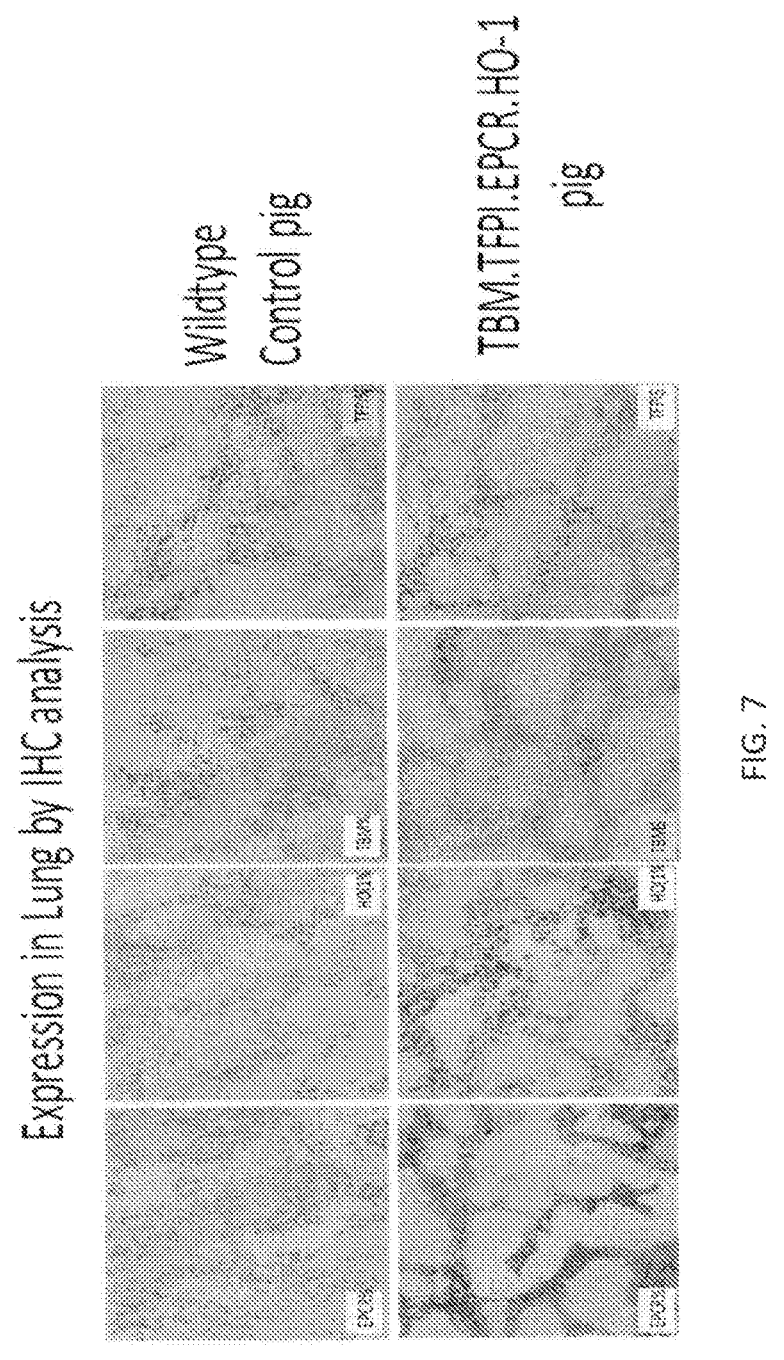

The neo gene located within the modified alpha Gal locus was used as a landing pad. The alpha Gal locus is known to have strong expression in most cell lineages and all organs and tissues within pigs. Toward stable and consistent expression of 4 transgenes, a 4-gene MCV vector was successfully targeted into the Gal locus using CRISPR-assisted homologous recombination. Such recombination is also known as homology-driven recombination (HDR). This fragment consists of pREV941 MCV flanked by ~500 bp $Neo^r$ gene homology arms (located within the modified Gal locus), and where ϕC31 and Bxb1 attP sites were also included in this vector to allow recombinase-mediated swap-out of MCV's for future modifications (see FIG. 7). This 941hdr vector was transfected along with a Neo-Gal CRISPR guide DNA vector into GTKO.CD46 fetal fibroblasts. Two cell clones were identified by 5' and 3' junction PCR, and DNA sequencing of the junctions with confirmed precise integration of the MCV941 fragment. One gene edited cell line had monoallelic, and a second cell clone had biallelic targeted insertion of the 14 kb pREV941 MCV into the alpha Gal locus. Both cell clones were mixed and used for SCNT, and nine embryo transfers performed. 9 live pigs were produced from 3 pregnancies, with DNA-sequence-confirmed biallelic integration of the pREV941 MCV at the alpha Gal locus. Targeted pigs derived from monoallelic integrations were not produced.

Figure 9:
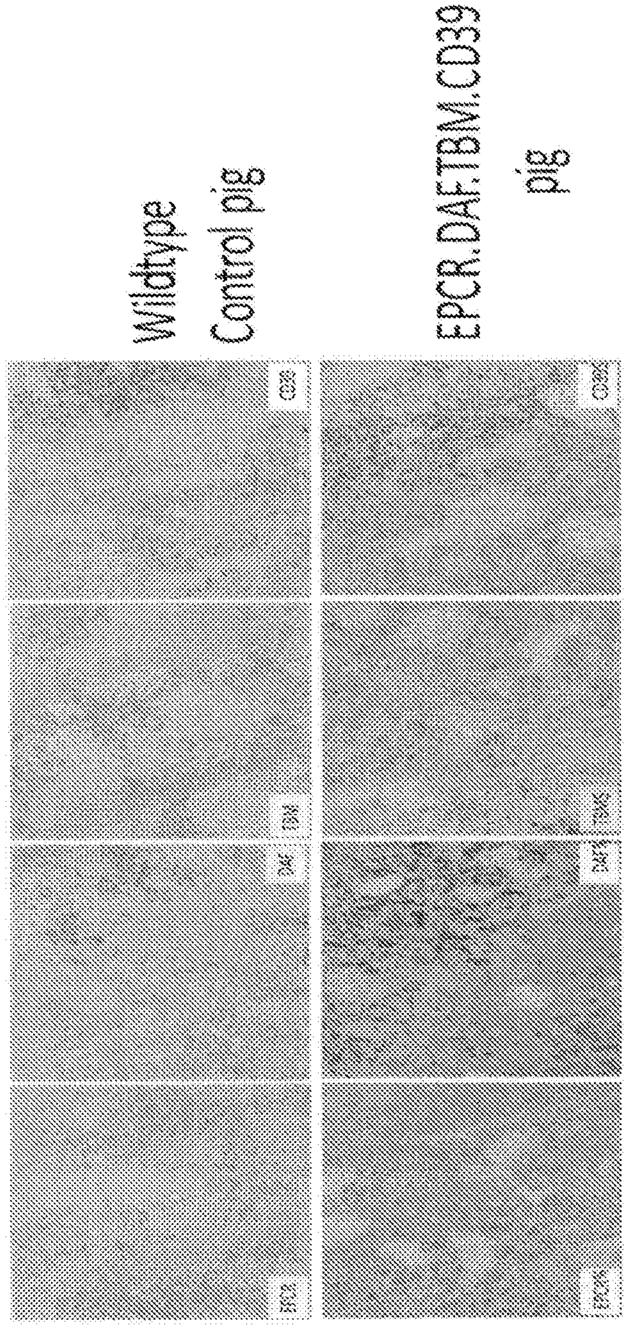
FIG. 9 depicts immunohistochemistry staining of EPCR, DAF, TBM, and CD39 transgenes in lung sections from negative control wild type pig and a 941HDR targeted pig. Expression was observed for all 4 human transgenes. Expression of transgenes in this MCV from the strong constitutive CAG promoter (EPCR and DAF) was stronger than that observed for transgenes under control of the endothelial-specific pICAM-2 promoter (TBM and CD39).
Figure 10:
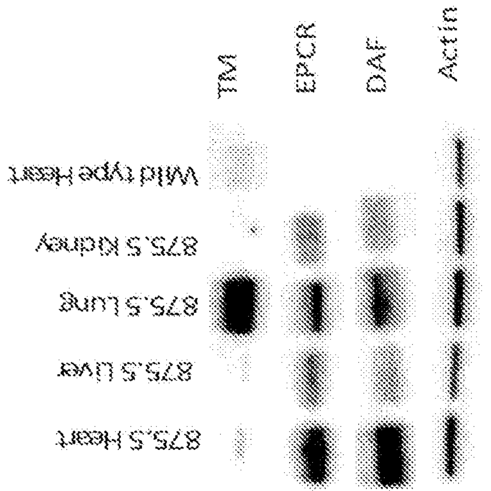
FIG. 10 depicts western blot analysis of heart, liver, lung, and kidney tissue lysates from 941HDR targeted pig. Anti-human monoclonal antibodies specific for TBM (under control of the endo-specific pICAM2 promoter), and EPCR and DAF (sharing CAG promoter) were optimized for detection of transgene expression in tissues from MCV-transgenic pigs (specifically 941HDR in this case). Expression in the milieu of alpha Gal locus integration was observed in all tissues for EPCR and DAF, and weaker for TBM (except high in lung), demonstrating good expression of multiple transgenes at this predetermined site in the genome, and importantly in live pigs.

A pig was euthanized and samples from this pig used for characterization of transgene expression by immunohistochemistry (IHC) in lung (FIG. 9), and in multiple organs by Western blot analysis (FIG. 10). The remaining 8 pigs with targeted integration of this pREV941 MCV at the alpha Gal locus were thriving.

Example 7: GTKO.CD46hom+EPCR.HO-1.TBM.CD47 with Gal Homology Arms (pREV971HDR)

Multiple MCV vectors were modified to harbor flanking homology arms to allow utilization with gene editing tools, including pREV958, pREV 941, pREV971, and pREV954. Two cell clones were identified that carried targeted insertion of pREV971, as indicated by LR-PCR, junction PCR (into the alpha Gal locus), and DNA sequencing. A pool of targeted 971 HDR colonies (Icam-TBM.2A.CD47-CAG.EPCR.2A.HO1), were used for SCNT, and reconstructed embryos were introduced into 12 recipients. Six pregnancies were produced from this effort, one of which was used for fetus isolation. All eight fetuses from one pregnancy were analyzed by long range PCR and determined to be mono-allelic targeted knockins for the pREV971 MCV vector.

Figures 11A, 11B:
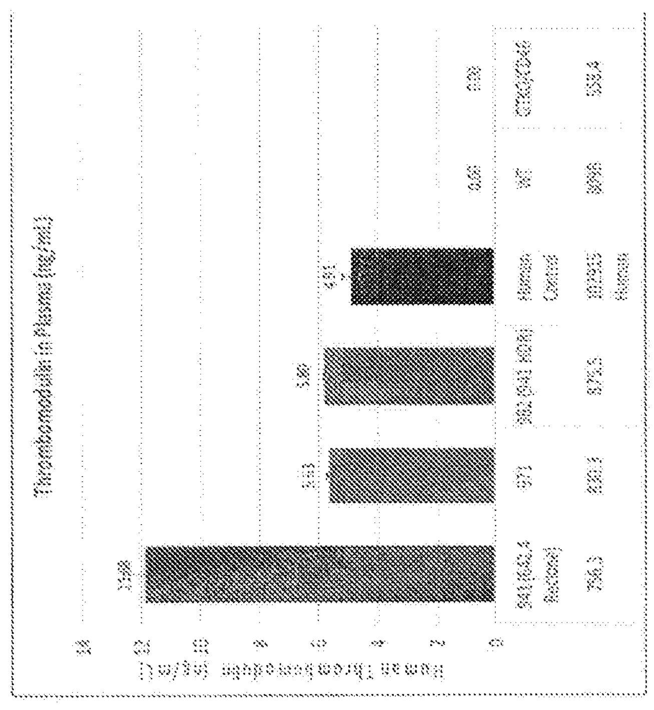
FIG. 11 A depicts ELISA detection of human thrombomodulin expression in multiple lines of TBM transgenic MCV pigs, including 941 HDR targeted to the alpha Gal locus (pig 875-5).

In addition, fetal collection was adopted for such putative knockin events, based on the potential to look at fetal expression of the MCV genes in pre-term pigs, as predictive for expression in live born pigs. Expression in lung microvascular endothelial cells (MVECs) by flow cytometry was confirmed in pREV971-HDR targeted fetuses for TBM and CD47, and at higher levels of HO1 and EPCR as compared to negative controls (FIG. 11B). An ELISA assay was also performed to compare TBM expression in random integration MCV pigs (pig 756.1 with pREV941 and pig 830-3 with pREV971) versus pREV941-HDR (pig 875-5), where all except 756-1 were equivalent to expression of these genes in human endothelial cells (HUVEC).

Example 8: vWF Modification

Figure 17:
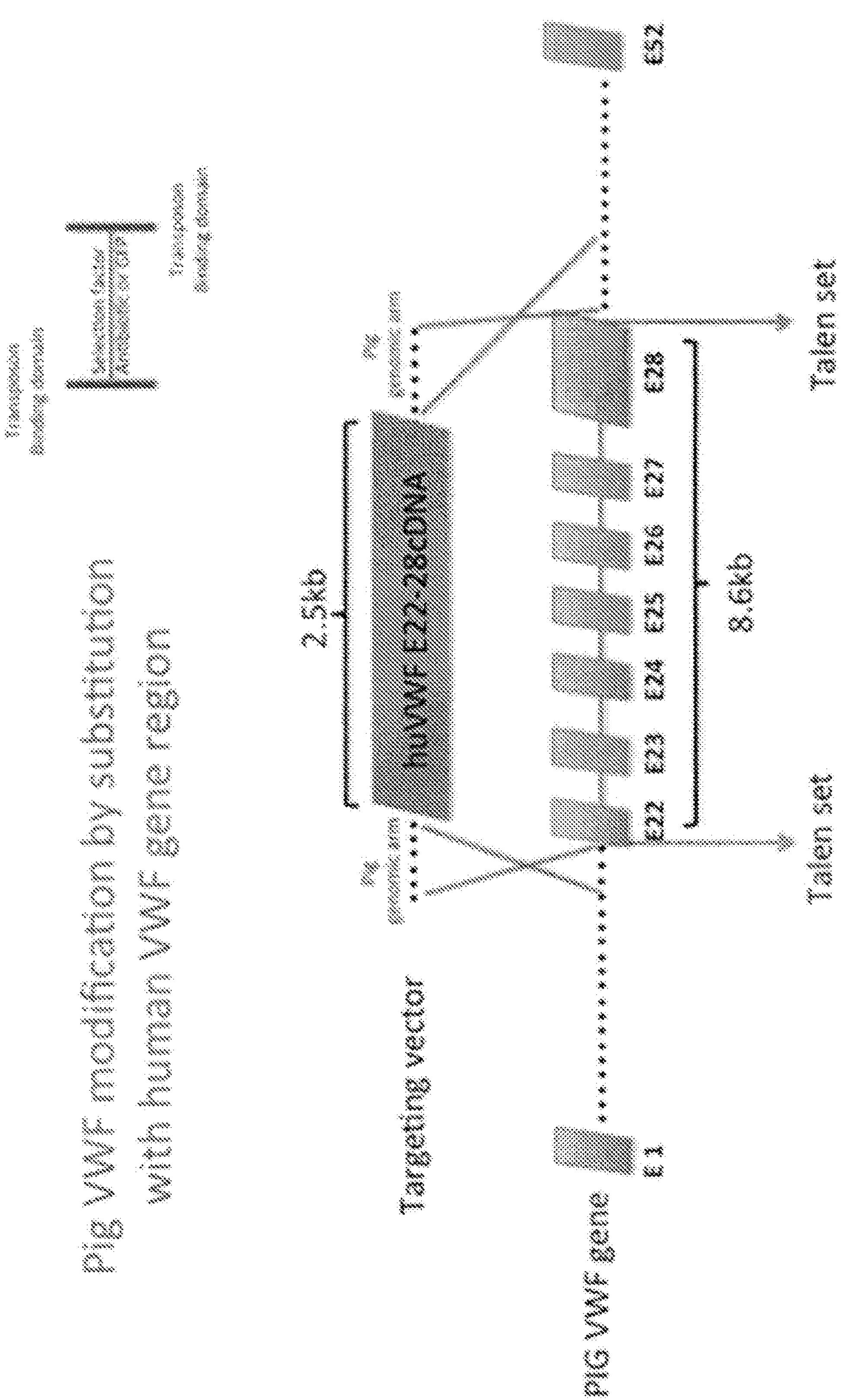
FIG. 17 depicts porcine vWF modification by substitution with human vWF.
Figure 18:
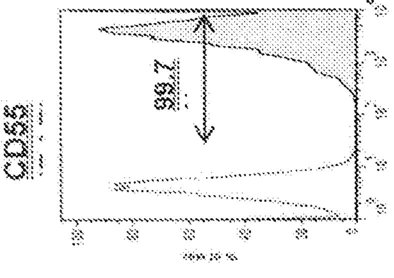
FIG. 18 shows high levels of expression of multiple transgenes for a transgenic pig according to the present invention and more specifically, six genetic modifications (GTKO.CD46.EPCR.CD55.TBM.CD39) and incorporation expression of five transgenes CD46.EPCR.CD55.TBM.CD39).
Figure 18:
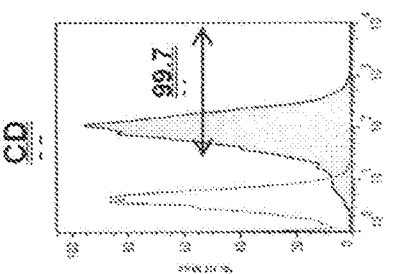
Figure 18:
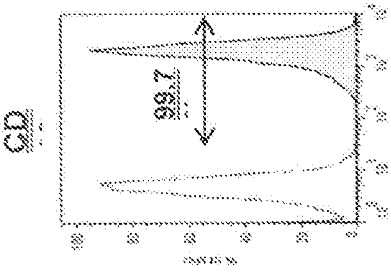
Figure 18:
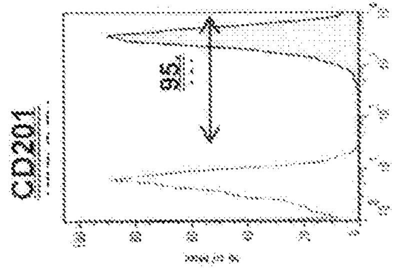
Figure 18:
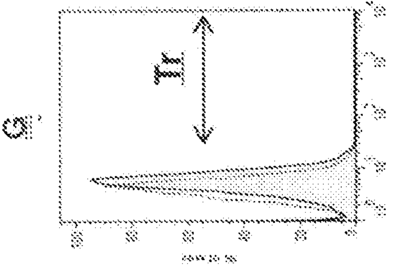
Figure 18:
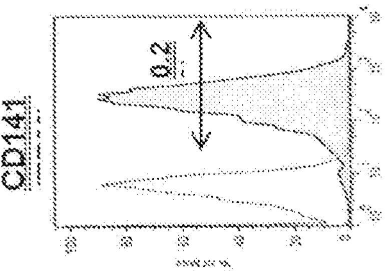

Modification of the porcine vWF was conducted to provide "humanization" to specific regions involved in spontaneous human platelet activation by porcine vWF. Regions within the D3 (partial), A1, A2, A3 (partial) domains were chosen to modify a porcine vWF region associated with folding and sequestration of the GPlb binding site in hvWF (D3 domain), as well as regions associated with collagen binding (one of two regions), with the GPlb receptor (A1 domain), and the ADAMTS13 cleavage site (A2 domain). Exons 22-28 encompass these regions, and thus these seven human exons were provided as a cDNA fragment (without the human introns), to simultaneously remove the equivalent porcine genomic region by gene targeting. The resulting gene replacement strategy created a chimeric human-pig exon 22-28 region of vWF, without otherwise modifying the porcine vWF gene locus. (see FIG. 17)

Figure 12:
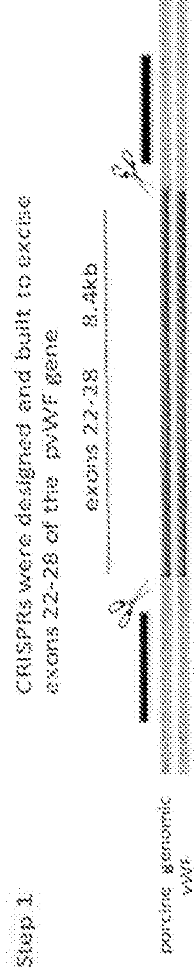
FIG. 12 depicts humanization of the porcine vWF locus via CRISPR-enhanced knockin and replacement of porcine exons 22-28 with human equivalent exons 22-28 as a cDNA. In step 1, following transfection of pig fibroblasts with both two CRISPR and a targeting vector containing both pig homology arms, flanking human exons 22-28, and with an internal selection cassette of GFP-Puro. The CRISPR-induced double stand breaks initiate stand exchange and homology dependent repair at the junction of porcine exon 22 and exon 28; with insertion of the human vWF sequences in step 2. Fetal cells with confirmed biallelic gene replacement, are then treated with a site-specific transposon (step 3) to remove the selection cassette, leaving behind an in-frame fusion of porcine-human sequences.
Figure 12:
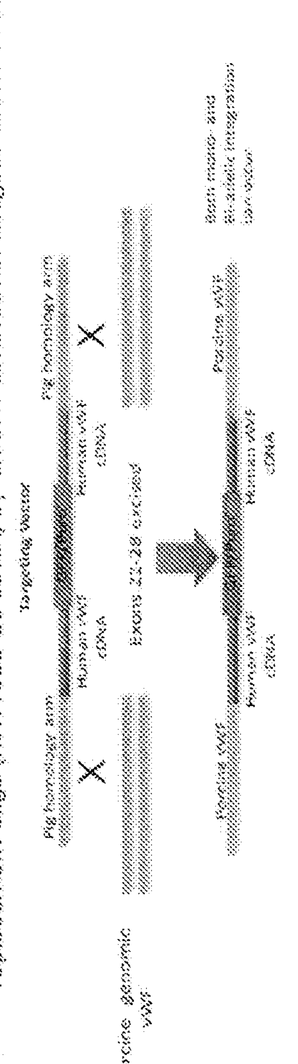
Figure 12:
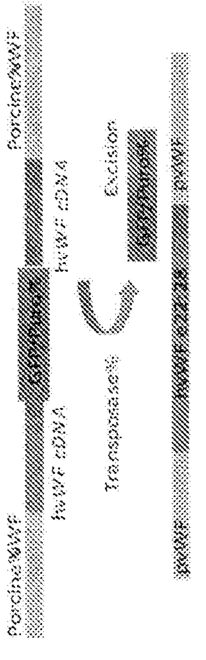
Figure 13:
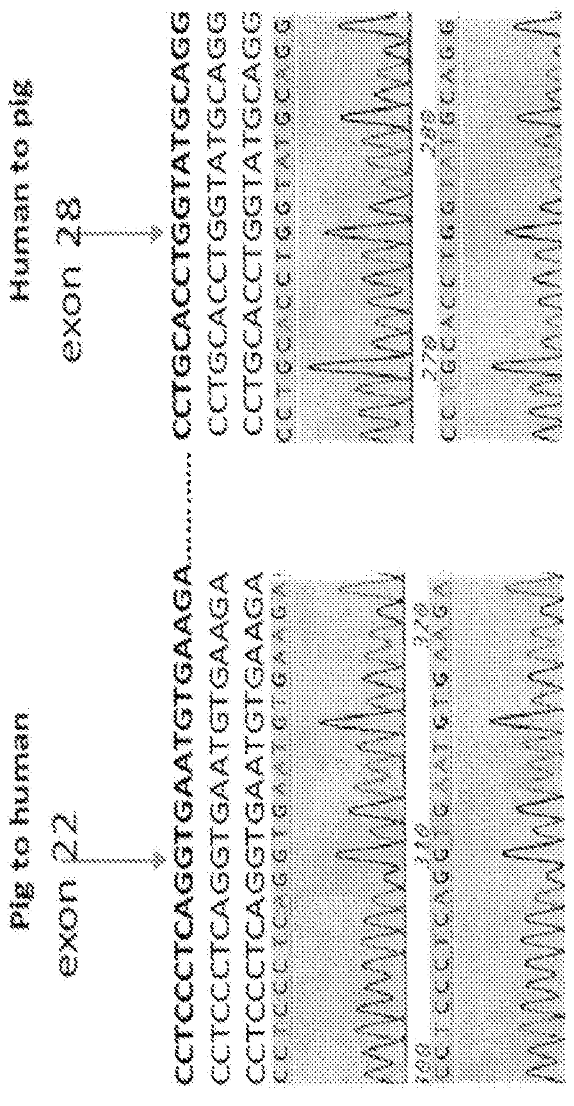
FIG. 13 depicts sequence analysis at junctions (5' and 3') showing perfect alignment of porcine and human VWF sequences upon knockin and insertion of human exons 22-28.

A DNA fragment encoding human exons 22-28 was synthesized, and flanked by genomic DNA homology arms homologous to porcine vWF intron 21 on the 5' end and porcine vWF intron 28 on the 3' end. This targeting vector also contained both GFP and puromycin-resistance genes to select and enrich for integration of the targeting vector. CRISPR/Cas9 plasmids were designed to bind and cut the porcine genomic sequence immediately adjacent to both ends of the fragment to be swapped out and replaced to create double stranded breaks. CRISPR-assisted homologous recombination was used to integrate the human exon 22-28 vWF fragment into the porcine vWF locus by cotransfection in porcine GTKO.CD46 fibroblasts with the two CRISPR vectors along with the vWF targeting vector (see FIG. 12). Puro-resistant colonies were screened by junction PCR, long-range PCR, and the 5' and 3' targeted junction regions were sequenced to confirm proper targeting. Monoallelic knockin of the human vWF region into only one of the porcine vWF in the diploid fibroblasts was the anticipated result, however, we were surprised to obtain one cell line that had biallelic replacement of the 22-28 region (deletion of porcine genomic DNA and replacement with the human region. This human fragment replaced regions that are implicated in the spontaneous platelet aggregation as described above, and the humanized exons were in the form of a cDNA rather than a genomic fragment. The biallelic knockin cell line (homozygous for the exon 22-28 gene replacement) was used for SCNT, pregnancies were obtained, and d35 fetuses collected to obtain fetal cells. Proper biallelic targeted replacement was confirmed in the fetal cell lines which were banked for subsequent steps. In order to precisely fuse the human-pig DNA in frame, the hvWF knockin cells were treated with a transposase that precisely excised the selection factors (GFP and puro) imbedded in the targeting vector. Excision and proper in-frame fusion of the porcine-human chimeric vWF region was monitored by loss of the GFP gene through florescence activated cell sorting. A pool of excised fibroblast cells was used for SCNT resulting in five pregnancies. Two pregnancies were aborted and used to prepare fetal cells for further genotyping analysis and recloning. Of eight fetuses obtained, four were monoallelic for the excision event, and four were biallelic, where all excision events sequenced indicated perfect in-frame alignment of the human sequence with the flanking porcine vWF genomic sequence (see FIG. 13), as well as complete excision of the selection factors. Two pregnancies went to full term resulting in the birth of three live healthy pigs. Genotyping indicated that two of the pigs were monoallelic excision and one of the pigs had biallelic excision with both alleles being human pig fusions at exons 22-28.

Genotypically the humanized, chimeric vWF was as designed. For the monomeric excised pigs, one allele was null due to interruption of the porcine vWF gene with the GFP-puro election cassette still integrated at exon 22 (of a gene with 52 exons), while the other allele had the modified chimeric vWF allele. Western blot analysis with an antibody that cross reacts with both human and porcine vWF showed that a full length vWF protein was made in blood of both monoallelic and biallelic excised pigs, but where the monoallelic excised only made 50% levels of vWF due to inactivation of the non-excised allele.

Figure 14:
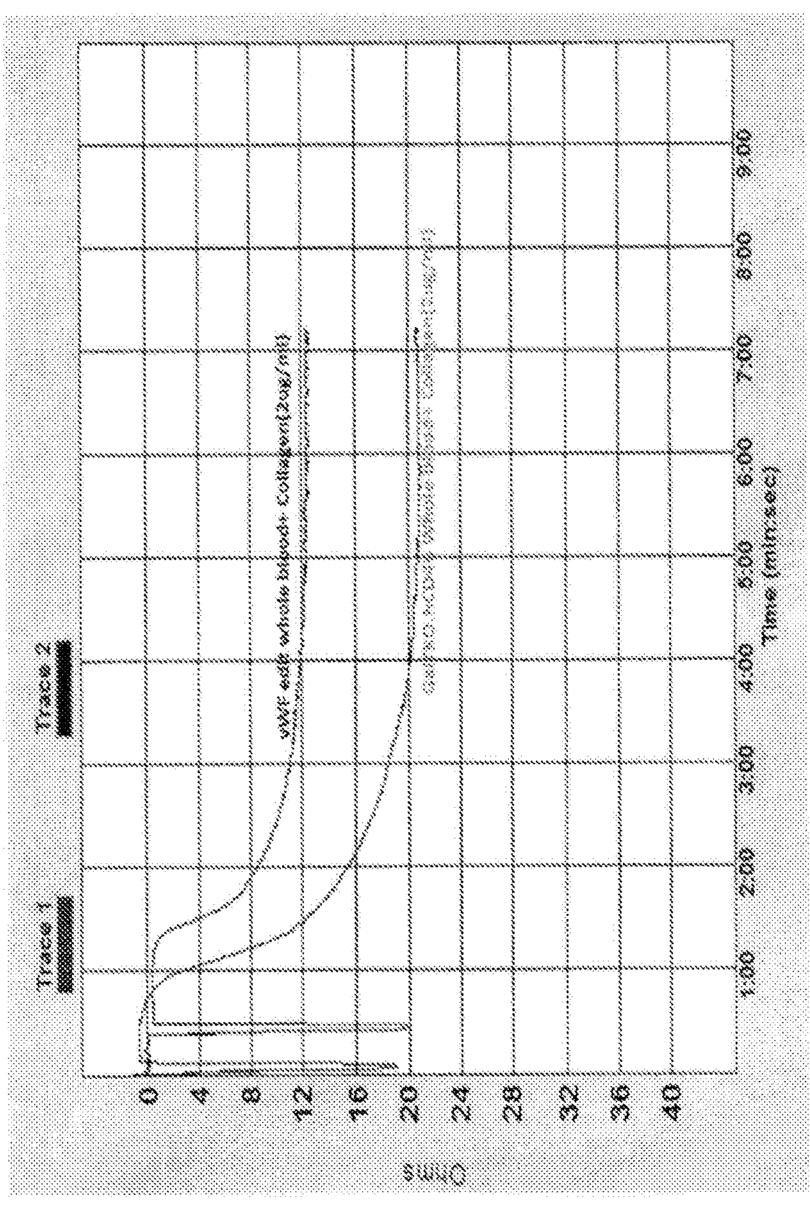
FIG. 14 depicts normal function of porcine vWF edit whole blood when tested by platelet aggregometry.
Figure 15:
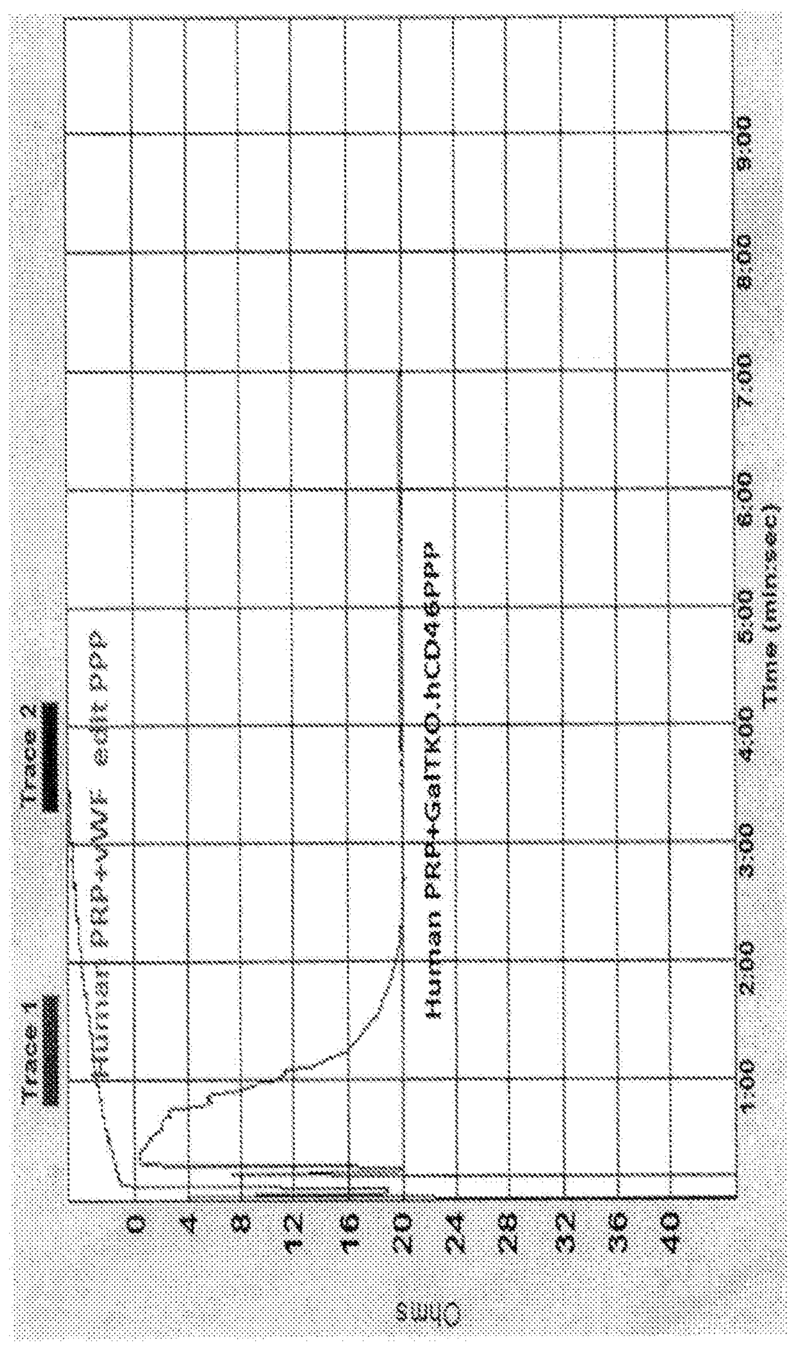
FIG. 15 depicts No Spontaneous Aggregation of Human Platelets Exposed vWF Edit Porcine Platelet Poor Plasma. Porcine platelet poor plasma (PPP) was prepared from citrate anticoagulated porcine blood samples using a two-step centrifugation protocol. Human platelet rich plasma (PRP) was prepared from a freshly drawn human blood sample (citrate anticoagulated). The human PRP was mixed 1:1 with porcine PPP in a tube, and aggregation of platelets was immediately recorded using a Chrono-log Whole Blood Aggregometer.
Figure 16:
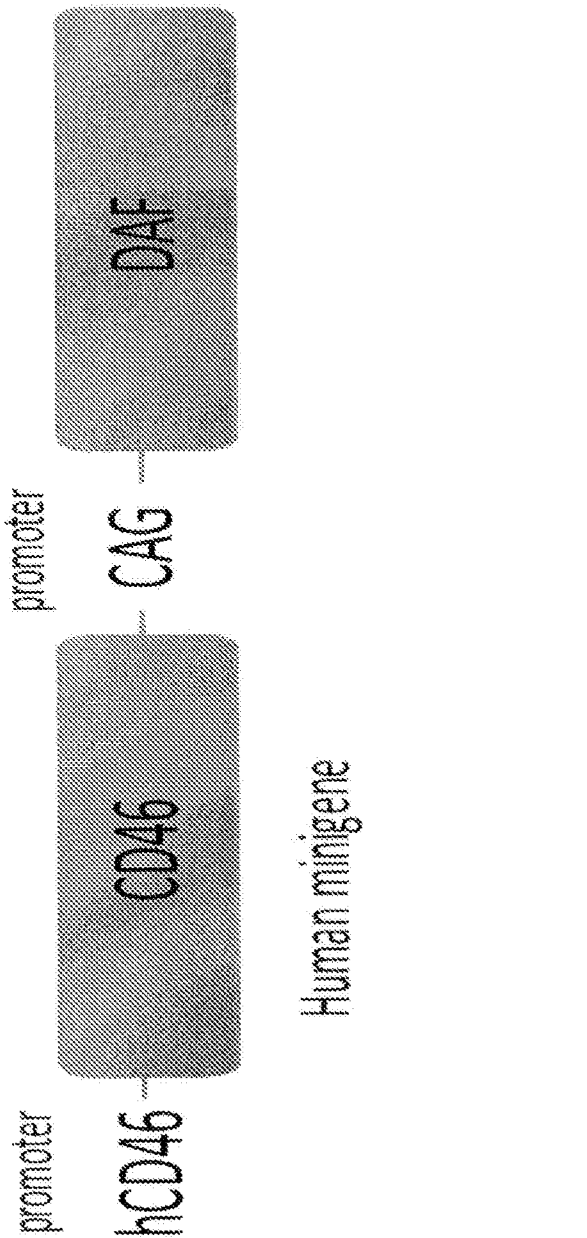
FIG. 16 depicts a bicistronic CD46/CD55 (DAF) vector according to the present invention.

Fresh drawn citrated porcine whole blood from VWF edit (humanized, chimeric vWF) and control GTKO.hCD46 animals was tested using a Chrono-log Whole Blood Aggregometer. Treatment with collagen agonist (2 ug/mL) caused aggregation of vWF edit blood, confirming that the VWF edit genotype was functional in its ability to produce a vWF protein that would bind collagen and stimulate platelet aggregation (n=3). Concurrently, GTKO.hCD46 whole blood (normal vWF) was tested and showed 50% more aggregation than the monoallelic VWF edit blood (n=2). See FIG. 14.

In addition, no spontaneous aggregation of human platelets was identified. Exposed vWF Edit Porcine Platelet Poor Plasma Porcine platelet poor plasma (PPP) was prepared from citrate anticoagulated porcine blood samples using a two-step centrifugation protocol. Human platelet rich plasma (PRP) was prepared from a freshly drawn human blood sample (citrate anticoagulated). The human PRP was mixed 1:1 with porcine PPP in a tube, and aggregation of platelets was immediately recorded using a Chrono-log Whole Blood Aggregometer. When PPP from animal 871.2, a vWF edit genotype, was mixed with human PRP, there was no spontaneous platelet aggregation (n=1). In contrast, when PPP from animals having a GKO.hCD46 genotype (unmodified porcine vWF) was mixed with human PRP, there was spontaneous aggregation of human platelets (n=2). The distinct lack of spontaneous aggregation of human platelets when used with plasma from the humanized, chimeric vWF edit pigs provided direct functional evidence of the intended phenotype. The humanized, chimeric vWF edit pigs can be tested using organs (lungs and other organs) from the pigs in both in ex vivo lung perfusions (with human blood), and in non-human primate transplants in vivo in baboons.

When PPP from animal 871.2, a VvWF edit genotype, was mixed with human PRP, there was no spontaneous platelet aggregation (n=1). In contrast, when PPP from animals having a GKO.hCD46 genotype (unmodified porcine vWF) was mixed with human PRP, there was spontaneous aggregation of human platelets (n=2). Such a distinct lack of spontaneous aggregation of human platelets when used with plasma from the humanized, chimeric vWF edit pigs provided direct functional evidence of the intended phenotype, and can be tested using organs (lungs and other organs) from such humanized pigs both in ex vivo lung perfusions (with human blood), and in non-human primate transplants in vivo in baboons to determine efficacy of the modification in preclinical models.

Re-clones of high expressing six (6)GE lines with random integration of pREV971 on a GTKO.CD46 background can be used to repeat humanization of the vWF locus in these more advanced genetics, and using the same method for targeted knockin of human exons 22-28. In addition, for the three (3)GE vWF knockin lines exemplified above (GTKO.CD46.vWF knockin), with demonstration of the chimeric human-pig vWF genotype (and desired phenotype), different MCV vectors (e.g. pREV954, pREV971 or pREV999) can be utilized to perform targeted insertion into the modified Gal locus in these lines as another means to insert 4 transgenes by crispr-enhanced to the Gal landing pad and in an existing vWF modified line.

Example 9. ß4galNT2 KO (on the GTKO.CD46.HLA-E background)

Three gene pigs (3GE) were generated with GTKO.CD46 and a genomic transgene for expression of human HLA-E (in combination with human beta-2-microglobulin as a trimer to prevent the natural killer (NK) cell response to xenotransplantation. HLA-E 3-gene pigs showed efficacy in the ex vivo lung transplant model with prevention of activation of NK cells. The HLAE pigs with the additional knockout of the porcine ß4galNT2 gene can be tested to provide additional protection from the xeno-antibody response generated in the host NHP during xenolung transplant. A CRISPR/Cas9 vector was generated to knockout the ß4galNT2 gene in GTKO.CD46.HLAE transgenic fibroblasts cells. A pool of cell clones that appeared to harbor bi-allelic ß4galNT2 KO's (B4KO) on the HLAE background was used for nuclear transfer. Eight fetuses were derived from one of the seven pregnancies produced and four of these have not only biallelic insertions or deletions (INDELs) at the ß4galNT2 loci, but functional knockout of ß4galNT2 (B4KO) as confirmed by complete lack of DBA lectin (FL-1031, Vector Labs) staining. The 3-gene HLAE lines with B4KO can be tested in ex vivo and in vivo Tx models.

In addition, MCV vectors have been constructed with homology arms (500 bp on each end) specific for the alpha Gal locus, such that these GTKO.CD46.HLAE.B4KO cell lines are further modified via CRISPR-assisted targeted insertion of an MCV such as EPCR.HO-1.TBM.CD47 (971HDR, see example 7).

Example 10: pREV999: GTKO.CD46.cagEPCR.DAFcagTFPI.CD47

Another MCV construct, shown to express all genes in immortal porcine endothelial cells, provides ubiquitous and robust expression of a set of genes that provided excellent life support in the in vivo lung Tx model but in which the transgenes were randomly integrated as two bicistronics at independent locations in the genome. Vectors have been generated with the pREV999 MCV (see FIG. 2) with either alpha Gal or porcine ß4galNT2 homology arms. This MCV with the addition of a B4GALNT2 KO on the background of GTKO and CD46 can be generated to provide enhanced life support in lung Tx. The pREV999 vector with Gal locus targeting arms was transfected into GTKO fibroblasts, and targeted colonies were identified by LRPCR and sequencing of the integration site junctions. Targeted cells were used for SCNT into six (6) recipients and pregnancies resulted.

Example 11

Targeted knockin of the pREV954 MCV (EPCR.DAF.TBM.A20) with alpha Gal homology arms has been achieved in GTKO fibroblasts, and cell lines with monoallelic knockin of the 954 MCV at the Gal locus have been used for SCNT.

Vectors have also been generated for pREV954 with B4GALNT2 arms. These arms can be substituted for homology arms targeted to the CMAH locus, the porcine ROSA26 or AAVS1. Insertion of this MCV into a second landing pad (as opposed to the Gal locus) with knockin of MCVs combined with a B4GALNT2 KO on the background of GTKO and CD46 can provide greatly enhanced life support in lung Tx.

Example 12. Generation of GTKO Pigs with Targeted Insertion of Two Complement Inhibitor Genes (CD46+DAF/CD55) at the Alpha Gal Locus A vector has been constructed to test additional genomic landing pads for transgene expression capacity. The additional genomic landing pads are CMAH and ß4GalNT2, thus accomplishing a simultaneous gene knockout and transgene integration.

A bi-cistronic CD46/CD55(DAF) vector has been constructed with elements to facilitate crispr-mediated knockin at the Gal locus of these two complement inhibitor transgenes toward reducing the number of targeting/integration events (ie. alpha Gal knockout cosegregating with the CD46/DAF transgenes) to facilitate breeding of such multitransgenic pig lines for production and clinical use. This vector incorporates two transgenes driven by two different promoters, the endogenous promoter for hCD46 and the constitutive CAG promoter for the complement inhibitor DAF. Alternatively, it is envisioned to also construct a bicistronic vector with both the CD46 and DAF genes under control of a single CAG promoter (also with homology arms for targeting to the modified Gal locus).

This bicistron is targeted to the Gal site in GTKO pigs, to provide robust protection from non-gal antibody associated complement fixation during Tx.

A cell line with this modification (CD46/DAF bicistron integrated at the alpha Gal landing pad) is further modified by insertion of an MCV, such as GTKO.CD46.EPCR.DAF.TBM.A20 (pREV954) with B4GALNT2 or CMAH arms at another landing pad (e.g. porcine I34galNT2 or CMAH locus, respectively), thus utilizing two landing pads for multigene editing in the same cell line to create a 7-gene pig (7GE), or if using two 4-gene MCVs targeted to two landing pads, on a GTKO background, to create a 9-gene modified pig (9GE).

We claim:

1. A transgenic pig comprising at least four transgenes, wherein:

(i) the at least four transgenes are incorporated and expressed at a single locus under the control of at least two promoters;

(ii) the single locus is a native or a modified locus selected from the group consisting of CMAH, β4GalNT2, and GGTA1, wherein the GGTA1 locus is a modified GGTA1 locus comprising a selectable marker gene or a large genomic insert;

(iii) the transgenic pig lacks expression of alpha 1, 3 galactosyltransferase;

(iv) two of the at least four transgenes are expressed as a first polycistron controlled by a first promoter and two of the four transgenes are expressed as a second polycistron controlled by a second promoter that is different from the first promoter; and the first polycistron comprises an endothelial cell-specific promoter driving the expression of TBM and CD47; and the second polycistron comprises a constitutive promoter driving the expression of EPCR and HO-1.

2. The transgenic pig of claim 1, wherein the single locus is a modified locus comprising an insertion, a deletion or a substitution, and wherein the single locus is modified using a gene-editing tool.

3. A transgenic alpha 1, 3 galactosyltransferase knockout pig comprising a human CD46 transgene and at least four transgenes incorporated and expressed at a single GGTAl locus under the control of a constitutive promoter and an endothelial cell specific promoter, or a constitutive promoter comprising an endothelium-specific enhancer element, wherein:

(i) the single GGTA1 locus is a modified GGTAl locus comprising a selectable marker gene or a large genomic insert;

(ii) two of the at least four transgenes are expressed as a first polycistron controlled by the endothelial cell-specific promoter and two of the four transgenes are expressed as a second polycistron controlled by the constitutive promoter ; and (iii) the first polycistron comprises TBM and CD47; and the second polycistron comprises EPCR and HO-1.

4. The transgenic pig of claim 1 further comprising at least two additional transgenes incorporated and expressed at a second single locus, wherein the at least two additional transgenes are selected from the group consisting of CD39, TFPI, CTLA4Ig, A20, HLA-E, CD55 (DAF), CD59, CD46, and CIITA-DN.

5. The transgenic pig of claim 4, wherein the at least two additional transgenes are (a) CD46 and DAF;
(b) CD46 and CD59;
(c) CD39 and DAF;
(d) A20 and DAF;
(e) CD39 and A20;
(f) CD59 and DAF; or
(g) TFPI and DAF.

6. The transgenic pig of claim 1, wherein the transgenic pig further expresses a human CD46 transgene.

7. The transgenic pig of claim 1, wherein the transgenic pig further lacks expression of cytidine monophosphate-N-acetylneuraminic acid hydroxylase (CMAH), and/or beta-1,4 N-acetyl-galactosaminyl transferase 2 (β4GalNT2).

8. An organ derived from the transgenic pig of claim 1.

9. A lung or lung fragment derived from the transgenic pig of claim 1.

10. A tissue derived from the transgenic pig of claim 1.

11. A cell derived from the transgenic pig of claim 1.

12. A method of making the transgenic pig of claim 1, the method comprising:

(i) incorporating the at least four transgenes under the control of at least two promoters at the single locus within a somatic cell pig genome to generate a somatic cell comprising a polygene pig genome, wherein the pig genome is selected from the group consisting of a gamete pig genome, a zygote pig genome, an embryo pig genome, or a blastocyst pig genome;

(ii) generating a pig zygote comprising the polygene pig genome, wherein the pig zygote is generated by microinjection, electroporation, or somatic cell nuclear transfer (SCNT); and (iii) maturing the pig zygote comprising the polygene pig genome into a transgenic pig.

13. The method of claim 12, wherein the pig zygote is generated by transferring the polygene pig genome by microinjection into a reconstructed SCNT zygote.

14. The method of claim 12, wherein the somatic cell pig genome comprises at least one additional genetic modification.

15. The method of claim 14, wherein the at least one additional genetic modification is selected from the group consisting of consisting of gene knock-outs, gene knock-ins, gene replacements, point mutations, deletions, insertions or substitutions of genes, gene fragments or nucleotides, large genomic insertions, or combinations thereof.

16. A method for treating a subject in need thereof, comprising implanting into the subject at least one organ, organ fragment, tissue or cell derived from the transgenic pig of claim 1.

17. The method of claim 16, wherein:

(a) the at least one organ is selected from the group consisting of lung, heart, kidney, liver, pancreas, or combinations thereof; or (b) the subject has advanced lung disease and a lung or lung fragment is implanted.

18. The method of claim 17, wherein the advanced lung disease is associated with chronic obstructive pulmonary disease (COPD), idiopathic pulmonary fibrosis (IPD), cystic fibrosis (CF), alpha 1-antitrypsin disease, or primary pulmonary hypertension.

19. The transgenic pig of claim 1, wherein the endothelial cell-specific promoter is ICAM-2 and/or the constitutive promoter is CAG.

* * * * *